(12) United States Patent
Spohn et al.

(10) Patent No.: US 11,938,093 B2
(45) Date of Patent: Mar. 26, 2024

(54) FLUID PATH CONNECTORS FOR MEDICAL FLUID DELIVERY

(71) Applicant: BAYER HEALTHCARE LLC, Whippany, NJ (US)

(72) Inventors: Michael Spohn, Fenelton, PA (US); Kevin Cowan, Allison Park, PA (US); James Dedig, Pittsburgh, PA (US); John Haury, Sewickley, PA (US)

(73) Assignee: BAYER HEALTHCARE LLC, Whippany, NY (US)

( * ) Notice: Subject to any disclaimer, the term of this patent is extended or adjusted under 35 U.S.C. 154(b) by 0 days.

(21) Appl. No.: 17/800,733

(22) PCT Filed: Feb. 18, 2021

(86) PCT No.: PCT/US2021/018523
§ 371 (c)(1),
(2) Date: Aug. 18, 2022

(87) PCT Pub. No.: WO2021/168076
PCT Pub. Date: Aug. 26, 2021

(65) Prior Publication Data
US 2023/0149263 A1    May 18, 2023

Related U.S. Application Data

(60) Provisional application No. 62/705,251, filed on Jun. 18, 2020, provisional application No. 62/979,584, filed on Feb. 21, 2020.

(51) Int. Cl.
*A61J 1/20*      (2006.01)
*A61M 5/178*   (2006.01)
*A61M 39/10*   (2006.01)

(52) U.S. Cl.
CPC .......... *A61J 1/2096* (2013.01); *A61M 5/1782* (2013.01); *A61M 39/1011* (2013.01)

(58) Field of Classification Search
CPC ................ A61J 1/2096; A61M 5/1782; A61M 39/1011; A61M 2039/1027; A61M 2039/1077
See application file for complete search history.

(56) References Cited

U.S. PATENT DOCUMENTS 352,715 A    11/1886   Sandmark
508,584 A    11/1893   Stevens
(Continued)

FOREIGN PATENT DOCUMENTS

CN    103917269 A    7/2014
CN    105521533 A    4/2016
(Continued)

OTHER PUBLICATIONS

International Preliminary Report on Patentability and Written Opinion dated Sep. 24, 2015 from corresponding PCT Application No. PCT/US2014/022629.
(Continued)

*Primary Examiner* — Theodore J Stigell
(74) *Attorney, Agent, or Firm* — Joseph L. Kent; James R. Stevenson; David Schramm

(57) ABSTRACT

A fluid path connector for a medical fluid delivery system, the fluid path connector including a first connector element comprising a body, a first lumen, a first flexible leg, and a second flexible leg, and a second connector element comprising a body defining an undercut, a second lumen, a channel defined in the body, and at least one sealing element positioned within the channel, in which the first flexible leg comprises a first flange and the second flexible leg comprises a second flange, and in which, upon engagement of the first connector element with the second connector ele- (Continued)

ment, the first flange and the second flange engage with the undercut of the body of the second connector element to prevent disengagement of the first connector element and the second connector element.

19 Claims, 33 Drawing Sheets

(56) References Cited

U.S. PATENT DOCUMENTS

| | | | |
|---|---|---|---|
| 798,093 A | 8/1905 | Edward |
| 817,054 A | 4/1906 | Daniel |
| 937,029 A | 10/1909 | Blessing et al. |
| 945,143 A | 1/1910 | Iacques |
| 1,388,946 A | 8/1921 | Goold |
| 1,930,929 A | 10/1933 | Joel et al. |
| 2,062,285 A | 12/1936 | Sam et al. |
| 2,511,291 A | 6/1950 | Mueller |
| 2,514,575 A | 7/1950 | Hein et al. |
| 2,583,206 A | 1/1952 | Borck et al. |
| 2,592,381 A | 4/1952 | Blackman |
| 2,616,422 A | 11/1952 | Jones |
| 2,667,163 A | 1/1954 | Smith |
| 2,667,164 A | 1/1954 | Smith |
| 2,667,165 A | 1/1954 | Smith |
| 2,667,872 A | 2/1954 | Smith |
| 2,672,866 A | 3/1954 | Kater |
| 2,673,561 A | 3/1954 | Peterson, Jr. |
| 2,688,963 A | 9/1954 | Smith |
| 2,688,964 A | 9/1954 | Smith |
| 2,690,179 A | 9/1954 | Fox |
| 2,717,598 A | 9/1955 | Krasno |
| 2,805,662 A | 9/1957 | Lawshe et al. |
| 2,911,972 A | 11/1959 | Elinger |
| 2,915,986 A | 12/1959 | Sisson |
| 2,935,067 A | 5/1960 | Bouet |
| 2,950,717 A | 8/1960 | Bonet |
| 3,101,712 A | 8/1963 | Strazdins et al. |
| 3,155,281 A | 11/1964 | Stracey |
| 3,159,312 A | 12/1964 | Van Sciver, II |
| 3,161,194 A | 12/1964 | Chapman |
| 3,161,195 A | 12/1964 | Taylor et al. |
| 3,166,070 A | 1/1965 | Everett |
| 3,172,577 A | 3/1965 | Hartung |
| 3,190,619 A | 6/1965 | Penney et al. |
| 3,199,511 A | 8/1965 | Kulick |
| 3,231,139 A | 1/1966 | Bouet |
| 3,276,472 A | 10/1966 | Jinkens et al. |
| 3,301,293 A | 1/1967 | Santelli |
| 3,340,869 A | 9/1967 | Bane |
| 3,353,537 A | 11/1967 | Knox et al. |
| 3,390,821 A | 7/1968 | Mullan |
| 3,411,503 A | 11/1968 | Santomieri |
| 3,412,906 A | 11/1968 | Dinger |
| 3,442,424 A | 5/1969 | Sam et al. |
| 3,471,058 A | 10/1969 | Peter et al. |
| 3,473,524 A | 10/1969 | John |
| 3,474,844 A | 10/1969 | Rudolph et al. |
| 3,506,163 A | 4/1970 | James et al. |
| 3,507,278 A | 4/1970 | Winfried |
| 3,527,215 A | 9/1970 | Harry |
| 3,557,788 A | 1/1971 | Swartz |
| 3,613,963 A | 10/1971 | Berkmuller |
| 3,618,846 A | 11/1971 | Poli |
| 3,635,444 A | 1/1972 | Potter |
| 3,671,208 A | 6/1972 | Medsker |
| 3,699,961 A | 10/1972 | Szpur |
| 3,719,207 A | 3/1973 | Takeda |
| 3,736,932 A | 6/1973 | Satchell |
| 3,785,367 A | 1/1974 | Fortin et al. |
| 3,826,409 A | 7/1974 | Chilcoate |
| 3,868,967 A | 3/1975 | Harding |
| 3,873,003 A | 3/1975 | Seiferth et al. |
| 3,938,514 A | 2/1976 | Boucher |
| 3,998,223 A | 12/1976 | Dawe |
| 4,035,461 A | 7/1977 | Korth |
| 4,041,944 A | 8/1977 | Rhodes |
| 4,044,836 A | 8/1977 | Martin et al. |
| 4,064,879 A | 12/1977 | Leibinsohn |
| 4,066,080 A | 1/1978 | Sneider |
| 4,131,217 A | 12/1978 | Sandegren |
| 4,136,802 A | 1/1979 | Mascia et al. |
| 4,140,117 A | 2/1979 | Buckles et al. |
| 4,171,698 A | 10/1979 | Genese |
| 4,204,775 A | 5/1980 | Speer |
| 4,208,136 A | 6/1980 | King et al. |
| 4,236,516 A | 12/1980 | Nilson |
| 4,245,655 A | 1/1981 | Patel |
| 4,312,344 A | 1/1982 | Nilson |
| 4,318,400 A | 3/1982 | Peery et al. |
| 4,325,369 A | 4/1982 | Nilson |
| 4,329,067 A | 5/1982 | Goudy, Jr. |
| 4,349,129 A | 9/1982 | Amneus |
| 4,392,491 A | 7/1983 | Takasugi et al. |
| 4,411,656 A | 10/1983 | Cornett, III |
| 4,419,096 A | 12/1983 | Leeper et al. |
| 4,438,845 A | 3/1984 | Mochow |
| 4,441,823 A | 4/1984 | Power et al. |
| 4,444,310 A | 4/1984 | Odell |
| 4,526,296 A | 7/1985 | Berger et al. |
| 4,610,665 A | 9/1986 | Matsumoto et al. |
| 4,741,733 A | 5/1988 | Winchell et al. |
| 4,747,839 A | 5/1988 | Tarello et al. |
| 4,753,638 A | 6/1988 | Peters |
| 4,773,458 A | 9/1988 | Touzani |
| 4,824,145 A | 4/1989 | Carlsson |
| 4,850,807 A | 7/1989 | Frantz |
| 4,895,570 A | 1/1990 | Larkin |
| 4,904,239 A | 2/1990 | Winchell et al. |
| 4,952,068 A | 8/1990 | Flint |
| 4,969,879 A * | 11/1990 | Lichte ............... F16L 37/0985 604/905 |
| 5,000,739 A | 3/1991 | Kulisz et al. |
| 5,011,477 A | 4/1991 | Winchell et al. |
| 5,026,348 A | 6/1991 | Venegas |
| 5,033,631 A | 7/1991 | Nightingale |
| 5,048,684 A | 9/1991 | Scott |
| 5,120,315 A | 6/1992 | Hessel |
| 5,147,311 A | 9/1992 | Pickhard |
| 5,163,928 A | 11/1992 | Hobbs et al. |
| 5,178,610 A | 1/1993 | Tsujikawa et al. |
| 5,192,272 A | 3/1993 | Faure |
| 5,199,567 A | 4/1993 | Discko, Jr. |
| 5,201,438 A | 4/1993 | Norwood |
| 5,209,372 A | 5/1993 | Norwood |
| 5,236,204 A | 8/1993 | Hempel |
| 5,237,309 A | 8/1993 | Frantz et al. |
| 5,238,003 A | 8/1993 | Baidwan et al. |
| 5,240,130 A | 8/1993 | Osbakk |
| 5,242,422 A | 9/1993 | Schneberger et al. |
| 5,263,940 A | 11/1993 | Kriesel |
| 5,269,428 A | 12/1993 | Gilbert |
| 5,312,018 A | 5/1994 | Evezich |
| 5,316,452 A | 5/1994 | Bogen et al. |
| 5,318,520 A | 6/1994 | Nakao |
| 5,318,540 A | 6/1994 | Athayde et al. |
| 5,333,761 A | 8/1994 | Davis et al. |
| 5,342,313 A | 8/1994 | Campbell et al. |
| 5,353,961 A | 10/1994 | Debush |
| 5,370,250 A | 12/1994 | Gilbert |
| 5,383,858 A | 1/1995 | Reilly et al. |
| 5,397,157 A | 3/1995 | Hempel et al. |
| 5,399,173 A | 3/1995 | Parks et al. |
| 5,431,185 A | 7/1995 | Shannon et al. |
| 5,492,147 A | 2/1996 | Challender et al. |
| 5,507,535 A * | 4/1996 | McKamey ......... F16L 27/0816 604/533 |
| 5,520,653 A | 5/1996 | Reilly et al. |
| 5,573,129 A | 11/1996 | Nagata et al. |
| 5,578,005 A | 11/1996 | Sancoff et al. |
| 5,584,413 A | 12/1996 | Jung |
| 5,592,948 A | 1/1997 | Gatten |
| 5,609,580 A | 3/1997 | Kwiatkowski et al. |

(56) References Cited

U.S. PATENT DOCUMENTS

| | | |
|---|---|---|
| 5,615,791 A | 4/1997 | Vatelot et al. |
| 5,638,995 A | 6/1997 | Mazda |
| 5,651,776 A | 7/1997 | Appling et al. |
| 5,683,369 A | 11/1997 | Tsukada |
| 5,725,500 A | 3/1998 | Micheler |
| 5,758,789 A | 6/1998 | Shin et al. |
| 5,794,107 A | 8/1998 | Russell |
| 5,827,233 A | 10/1998 | Futagawa et al. |
| 5,836,922 A | 11/1998 | Hansen et al. |
| 5,873,861 A | 2/1999 | Hitchins et al. |
| 5,893,843 A | 4/1999 | Rodrigues Claro |
| 5,899,889 A | 5/1999 | Futagawa et al. |
| 5,935,105 A | 8/1999 | Manning et al. |
| 5,957,898 A | 9/1999 | Jepson et al. |
| RE36,377 E | 11/1999 | Gilbert |
| 5,976,112 A | 11/1999 | Lyza, Jr. |
| 5,979,326 A | 11/1999 | Ohinata |
| 5,980,489 A | 11/1999 | Kriesel |
| 5,984,378 A * | 11/1999 | Ostrander ........... F16L 37/0985 285/423 |
| 6,054,194 A | 4/2000 | Kane |
| 6,056,724 A | 5/2000 | Lacroix |
| 6,062,437 A | 5/2000 | Mascitelli |
| 6,063,058 A | 5/2000 | Sakamoto |
| 6,077,252 A | 6/2000 | Siegel |
| 6,105,815 A | 8/2000 | Mazda |
| 6,132,396 A | 10/2000 | Antanavich et al. |
| 6,142,976 A | 11/2000 | Kubo |
| 6,159,183 A | 12/2000 | Neer et al. |
| 6,177,049 B1 | 1/2001 | Schnell et al. |
| 6,216,915 B1 | 4/2001 | Harman et al. |
| 6,224,577 B1 | 5/2001 | Dedola et al. |
| 6,250,505 B1 | 6/2001 | Petit |
| 6,270,482 B1 | 8/2001 | Rosoff et al. |
| 6,306,191 B1 | 10/2001 | McInerney et al. |
| 6,315,761 B1 | 11/2001 | Shcherbina et al. |
| 6,319,235 B1 | 11/2001 | Yoshino |
| 6,322,542 B1 | 11/2001 | Nilson et al. |
| 6,328,715 B1 | 12/2001 | Dragan et al. |
| 6,332,876 B1 | 12/2001 | Poynter et al. |
| 6,442,418 B1 | 8/2002 | Evans, III et al. |
| 6,450,993 B1 | 9/2002 | Lin |
| 6,465,024 B1 | 10/2002 | Di et al. |
| 6,485,471 B1 | 11/2002 | Zivitz et al. |
| 6,497,684 B2 | 12/2002 | Witowski et al. |
| 6,558,358 B2 | 5/2003 | Rosoff et al. |
| 6,575,930 B1 | 6/2003 | Trombley, III et al. |
| 6,578,738 B1 | 6/2003 | Keller |
| 6,616,000 B1 | 9/2003 | Renz |
| 6,620,134 B1 | 9/2003 | Trombley, III et al. |
| 6,634,524 B1 | 10/2003 | Helmenstein |
| 6,643,537 B1 | 11/2003 | Zatezalo et al. |
| 6,652,489 B2 | 11/2003 | Trocki et al. |
| 6,702,143 B2 | 3/2004 | Wang |
| 6,716,195 B2 | 4/2004 | Nolan, Jr. et al. |
| 6,723,074 B1 | 4/2004 | Halseth |
| 6,726,657 B1 | 4/2004 | Dedig et al. |
| 6,731,971 B2 | 5/2004 | Evans et al. |
| 6,773,417 B2 | 8/2004 | Fitzgibbons et al. |
| 6,840,164 B2 | 1/2005 | Eastman |
| 6,855,130 B2 | 2/2005 | Saulenas et al. |
| 6,866,039 B1 | 3/2005 | Wright et al. |
| 6,866,654 B2 | 3/2005 | Callan et al. |
| 6,869,419 B2 | 3/2005 | Dragan et al. |
| 6,921,384 B2 | 7/2005 | Reilly et al. |
| RE38,770 E | 8/2005 | Gilbert |
| 6,974,443 B2 | 12/2005 | Reilly et al. |
| 6,984,222 B1 | 1/2006 | Hitchins et al. |
| 7,004,213 B2 | 2/2006 | Hansen |
| 7,011,650 B2 | 3/2006 | Rosoff et al. |
| 7,094,216 B2 | 8/2006 | Trombley, III et al. |
| 7,101,352 B2 | 9/2006 | Dochon et al. |
| 7,192,416 B1 | 3/2007 | Lazzaro et al. |
| 7,192,549 B2 | 3/2007 | Hansen |
| 7,240,926 B2 | 7/2007 | Dalle et al. |
| 7,250,039 B2 | 7/2007 | Fitzgerald |
| 7,309,463 B2 | 12/2007 | Hansen |
| 7,351,221 B2 | 4/2008 | Trombley, III et al. |
| 7,419,478 B1 | 9/2008 | Reilly et al. |
| 7,427,281 B2 | 9/2008 | Uber et al. |
| 7,457,804 B2 | 11/2008 | Uber, III et al. |
| 7,462,166 B2 | 12/2008 | Kowan et al. |
| 7,497,843 B1 | 3/2009 | Castillo et al. |
| 7,513,378 B2 | 4/2009 | Mori et al. |
| 7,540,856 B2 | 6/2009 | Hitchins |
| 7,553,294 B2 | 6/2009 | Lazzaro et al. |
| 7,556,619 B2 | 7/2009 | Spohn et al. |
| 7,563,249 B2 | 7/2009 | Schriver et al. |
| 7,581,559 B2 | 9/2009 | Bausmith et al. |
| 7,597,683 B2 | 10/2009 | Myhrberg et al. |
| 7,604,623 B2 | 10/2009 | Brunner et al. |
| 7,611,503 B2 | 11/2009 | Spohn et al. |
| 7,621,395 B2 | 11/2009 | Mogensen et al. |
| 7,666,169 B2 | 2/2010 | Cowan et al. |
| 7,686,788 B2 | 3/2010 | Freyman et al. |
| 7,766,883 B2 | 8/2010 | Rellly et al. |
| 7,802,691 B2 | 9/2010 | Musalek et al. |
| 7,818,992 B2 | 10/2010 | Riley et al. |
| 7,861,893 B2 | 1/2011 | Voegele et al. |
| 7,996,381 B2 | 8/2011 | Uber, III et al. |
| 8,057,406 B2 | 11/2011 | Mohiuddin |
| 8,147,464 B2 | 4/2012 | Spohn et al. |
| 8,162,903 B2 | 4/2012 | Reilly et al. |
| 8,337,456 B2 | 12/2012 | Schriver et al. |
| 8,388,580 B2 | 3/2013 | Schriver et al. |
| 8,419,676 B2 | 4/2013 | Evans et al. |
| 8,439,863 B2 | 5/2013 | Fago et al. |
| 8,521,716 B2 | 8/2013 | Uber, III et al. |
| 8,540,698 B2 | 9/2013 | Spohn et al. |
| 8,740,877 B2 | 6/2014 | Borlaug et al. |
| 8,795,240 B2 | 8/2014 | Chelak |
| 8,872,708 B2 | 10/2014 | Hill et al. |
| 8,882,702 B2 | 11/2014 | Suchecki et al. |
| 8,882,708 B2 | 11/2014 | Hieb et al. |
| 8,919,384 B2 | 12/2014 | Spohn et al. |
| 8,945,051 B2 | 2/2015 | Schriver et al. |
| 8,992,489 B2 | 3/2015 | Spohn et al. |
| 9,173,995 B1 | 11/2015 | Tucker et al. |
| 9,180,252 B2 | 11/2015 | Gelblum et al. |
| 9,180,260 B2 | 11/2015 | Huang et al. |
| 9,199,033 B1 | 12/2015 | Cowan et al. |
| 9,474,857 B2 | 10/2016 | Riley et al. |
| 9,498,570 B2 | 11/2016 | Cowan et al. |
| 9,555,379 B2 | 1/2017 | Schriver et al. |
| 9,566,381 B2 | 2/2017 | Barron et al. |
| 9,649,436 B2 | 5/2017 | Capone et al. |
| 9,901,671 B2 | 2/2018 | Toews et al. |
| 10,022,493 B2 | 7/2018 | Shearer, Jr. et al. |
| 10,046,106 B2 | 8/2018 | Cowan et al. |
| 10,105,491 B2 | 10/2018 | Gelblum et al. |
| 10,124,110 B2 | 11/2018 | Dedig et al. |
| 10,188,849 B2 | 1/2019 | Fangrow |
| 10,201,666 B2 | 2/2019 | Cowan et al. |
| 10,398,353 B2 | 9/2019 | Addison et al. |
| 10,420,902 B2 | 9/2019 | Cowan et al. |
| 10,507,319 B2 | 12/2019 | Haury et al. |
| 10,549,084 B2 | 2/2020 | Sokolov et al. |
| 10,857,345 B2 | 12/2020 | Uber, III et al. |
| 10,933,190 B2 | 3/2021 | Berry et al. |
| 11,007,118 B2 | 5/2021 | Cowan et al. |
| 11,083,882 B2 | 8/2021 | Schrauder et al. |
| 11,207,462 B2 | 12/2021 | Cowan et al. |
| 11,389,585 B2 | 7/2022 | Spohn et al. |
| 11,413,403 B2 | 8/2022 | Yoshioka et al. |
| 11,547,793 B2 | 1/2023 | Cowan et al. |
| 11,642,464 B2 | 5/2023 | McDermott et al. |
| 11,738,152 B2 | 8/2023 | Haury et al. |
| 2001/0004466 A1 | 6/2001 | Heinz et al. |
| 2001/0018575 A1 | 8/2001 | Lyza |
| 2002/0010596 A1 | 1/2002 | Matory |
| 2002/0147429 A1 | 10/2002 | Cowan et al. |
| 2003/0216695 A1 | 11/2003 | Yang |
| 2003/0226539 A1 | 12/2003 | Kim et al. |
| 2004/0064041 A1 | 4/2004 | Lazzaro et al. |

(56) References Cited

U.S. PATENT DOCUMENTS

| | | |
|---|---|---|
| 2004/0068224 A1 | 4/2004 | Couvillon et al. |
| 2004/0092905 A1 | 5/2004 | Azzolini |
| 2004/0116893 A1 | 6/2004 | Spohn et al. |
| 2004/0154788 A1 | 8/2004 | Symonds |
| 2004/0186457 A1 | 9/2004 | Truitt et al. |
| 2004/0249344 A1 | 12/2004 | Nemoto et al. |
| 2004/0254541 A1 | 12/2004 | Wong et al. |
| 2005/0082828 A1 | 4/2005 | Wicks et al. |
| 2005/0113754 A1 | 5/2005 | Cowan |
| 2005/0225082 A1 | 10/2005 | Dalle et al. |
| 2006/0052794 A1 | 3/2006 | Mcgill et al. |
| 2006/0149213 A1 | 7/2006 | Raybuck |
| 2006/0200083 A1 | 9/2006 | Freyman et al. |
| 2007/0068964 A1 | 3/2007 | Tanaami et al. |
| 2007/0129705 A1 | 6/2007 | Trombley et al. |
| 2008/0045925 A1 | 2/2008 | Stepovich et al. |
| 2008/0086087 A1 | 4/2008 | Spohn et al. |
| 2008/0146996 A1 | 6/2008 | Smisson et al. |
| 2009/0069792 A1 | 3/2009 | Frey et al. |
| 2009/0112087 A1 | 4/2009 | Fago |
| 2009/0216192 A1 | 8/2009 | Schriver et al. |
| 2009/0218243 A1 | 9/2009 | Gyrn et al. |
| 2010/0063445 A1 | 3/2010 | Sternberg et al. |
| 2010/0089475 A1 | 4/2010 | Tracey |
| 2010/0091361 A1 | 4/2010 | Yuuki |
| 2010/0114064 A1 | 5/2010 | Kalafut et al. |
| 2010/0286650 A1 | 11/2010 | Fitzgerald |
| 2011/0009826 A1 | 1/2011 | Lewis |
| 2011/0218434 A1 | 9/2011 | Ziemba et al. |
| 2011/0275988 A1 | 11/2011 | Davis et al. |
| 2011/0282196 A1 | 11/2011 | Martz |
| 2012/0020911 A1 | 1/2012 | Seliktar et al. |
| 2012/0101472 A1 | 4/2012 | Schroeder et al. |
| 2012/0123257 A1 | 5/2012 | Stokes, Jr. et al. |
| 2012/0178629 A1 | 7/2012 | Hudson et al. |
| 2012/0209111 A1 | 8/2012 | Cowan et al. |
| 2012/0217231 A1 | 8/2012 | Moore et al. |
| 2012/0245560 A1 | 9/2012 | Hochman |
| 2012/0253291 A1 | 10/2012 | Ivosevic et al. |
| 2013/0023048 A1 | 1/2013 | Kim et al. |
| 2013/0030291 A1 | 1/2013 | Lewis |
| 2013/0043273 A1 | 2/2013 | Lee et al. |
| 2013/0053774 A1 | 2/2013 | Kirkpatrick |
| 2013/0067416 A1 | 3/2013 | Barron et al. |
| 2013/0204130 A1 | 8/2013 | McArthur et al. |
| 2013/0211248 A1 | 8/2013 | Cowan et al. |
| 2013/0281940 A1 | 10/2013 | Gelblum et al. |
| 2013/0310756 A1 | 11/2013 | Whalley et al. |
| 2014/0124087 A1 | 5/2014 | Anderson et al. |
| 2014/0261713 A1 | 9/2014 | Schriver et al. |
| 2014/0276652 A1 | 9/2014 | Gittard |
| 2014/0374353 A1 | 12/2014 | Wright et al. |
| 2015/0260325 A1* | 9/2015 | Quick .................. F16L 37/252 285/326 |
| 2016/0030662 A1 | 2/2016 | Uber, III et al. |
| 2016/0250409 A1 | 9/2016 | Dedig et al. |
| 2017/0035974 A1 | 2/2017 | Berry et al. |
| 2017/0100534 A1 | 4/2017 | Fukikoshi et al. |
| 2017/0165427 A1 | 6/2017 | Uber, III et al. |
| 2017/0232173 A1 | 8/2017 | Perry et al. |
| 2018/0015274 A1 | 1/2018 | Haury et al. |
| 2018/0161496 A1 | 6/2018 | Berry et al. |
| 2018/0280630 A1 | 10/2018 | Jiang et al. |
| 2018/0296755 A1 | 10/2018 | Dahlin et al. |
| 2018/0339146 A1* | 11/2018 | Schrauder ............. A61M 5/281 |
| 2019/0240424 A1 | 8/2019 | Yoshioka et al. |
| 2020/0164141 A1 | 5/2020 | Biermann et al. |
| 2020/0206490 A1 | 7/2020 | Bae |
| 2020/0246541 A1 | 8/2020 | Neftel et al. |
| 2021/0023298 A1 | 1/2021 | McDermott et al. |
| 2021/0146064 A1 | 5/2021 | Knutsson |
| 2021/0193289 A1 | 6/2021 | Cowan et al. |
| 2021/0220561 A1 | 7/2021 | Spohn et al. |
| 2021/0316065 A1 | 10/2021 | Berry et al. |
| 2021/0353870 A1 | 11/2021 | Volkar et al. |
| 2023/0181816 A1 | 6/2023 | Lee |

FOREIGN PATENT DOCUMENTS

| | | |
|---|---|---|
| EP | 0446898 A2 | 9/1991 |
| EP | 1086661 A2 | 3/2001 |
| EP | 1572266 A2 | 9/2005 |
| EP | 1769849 A1 | 4/2007 |
| EP | 1800704 A1 | 6/2007 |
| EP | 1572266 B1 | 4/2008 |
| EP | 2005934 A2 | 12/2008 |
| EP | 2098258 A1 | 9/2009 |
| EP | 2692375 A1 | 2/2014 |
| EP | 2719420 A1 | 4/2014 |
| EP | 2754459 A1 | 7/2014 |
| EP | 2767299 A1 | 8/2014 |
| EP | 3057648 A1 | 8/2016 |
| EP | 2962770 B1 | 3/2017 |
| EP | 3248635 A1 | 11/2017 |
| FR | 1288915 A | 3/1962 |
| GB | 2214819 A | 9/1989 |
| GB | 2374143 A | 10/2002 |
| JP | H02-88664 | 7/1990 |
| JP | H0849598 A | 2/1996 |
| JP | H0999034 A | 4/1997 |
| JP | 5485885 B2 | 5/2014 |
| JP | 5511409 B2 | 6/2014 |
| JP | 5882595 B2 | 3/2016 |
| JP | 5897798 B2 | 3/2016 |
| JP | 6552258 B2 | 7/2019 |
| JP | 6839853 B2 | 3/2021 |
| WO | 9221391 A1 | 12/1992 |
| WO | 9528195 A1 | 10/1995 |
| WO | 9707841 A2 | 3/1997 |
| WO | 0204049 A1 | 1/2002 |
| WO | 02066100 A2 | 8/2002 |
| WO | 2004033023 A1 | 4/2004 |
| WO | 2005035995 A1 | 4/2005 |
| WO | 2007133942 A2 | 11/2007 |
| WO | 2008050218 A2 | 5/2008 |
| WO | 2008153831 A2 | 12/2008 |
| WO | 2009038955 A1 | 3/2009 |
| WO | 2010004206 A2 | 1/2010 |
| WO | 2010014654 A1 | 2/2010 |
| WO | 2011011346 A1 | 1/2011 |
| WO | 2011125303 A1 | 10/2011 |
| WO | 2011129175 A1 | 10/2011 |
| WO | 2012061140 A1 | 5/2012 |
| WO | 2012155035 A1 | 11/2012 |
| WO | 2013043868 A1 | 3/2013 |
| WO | 2013043881 A1 | 3/2013 |
| WO | 2013043889 A1 | 3/2013 |
| WO | 2014027009 A1 | 2/2014 |
| WO | 2014055283 A1 | 4/2014 |
| WO | 2014160326 A1 | 10/2014 |
| WO | 2015058088 A1 | 4/2015 |
| WO | 2015066506 A2 | 5/2015 |
| WO | 2015164783 A1 | 10/2015 |
| WO | 2016058946 A1 | 4/2016 |
| WO | 2016069711 A1 | 5/2016 |
| WO | 2016069714 A1 | 5/2016 |
| WO | 2016112163 A1 | 7/2016 |
| WO | 2016157886 A1 | 10/2016 |
| WO | 2016172467 A1 | 10/2016 |
| WO | 2016190904 A1 | 12/2016 |
| WO | 2016191485 A1 | 12/2016 |
| WO | 2017040154 A1 | 3/2017 |
| WO | 2017091635 A1 | 6/2017 |
| WO | 2017091636 A1 | 6/2017 |
| WO | 2017091643 A1 | 6/2017 |
| WO | 2018053074 A1 | 3/2018 |
| WO | 2018057386 A1 | 3/2018 |
| WO | 2018218132 A1 | 11/2018 |
| WO | 2019046259 A1 | 3/2019 |
| WO | 2019046260 A1 | 3/2019 |
| WO | 2019046299 A1 | 3/2019 |
| WO | 2019152978 A1 | 8/2019 |

(56) References Cited

FOREIGN PATENT DOCUMENTS

| | | |
|---|---|---|
| WO | 2019204605 A1 | 10/2019 |
| WO | 2019204617 A1 | 10/2019 |
| WO | 2020055785 A1 | 3/2020 |
| WO | 2020055818 A1 | 3/2020 |
| WO | 2021050507 A1 | 3/2021 |
| WO | 2021168076 A1 | 8/2021 |
| WO | 2021173743 A1 | 9/2021 |
| WO | 2021188416 A1 | 9/2021 |
| WO | 2021188460 A1 | 9/2021 |
| WO | 2021222619 A1 | 11/2021 |
| WO | 2021247595 A1 | 12/2021 |
| WO | 2021257667 A1 | 12/2021 |
| WO | 2021257699 A1 | 12/2021 |
| WO | 2022035791 A1 | 2/2022 |
| WO | 2022036058 A1 | 2/2022 |
| WO | 2022265695 A1 | 12/2022 |

OTHER PUBLICATIONS

International Search Report and Written Opinion dated Jul. 30, 2014 from corresponding PCT Application No. PCT/US2014/022629.
"International Search Report and Written Opinion from PCT Application No. PCT/US2016/063448", dated Feb. 24, 2017.
"Supplementary European Search Report from EP 14770001", dated Nov. 25, 2016.
International Preliminary Report on Patentability and Written Opinion dated Sep. 24, 2015 from corresponding PCT Application No. PCT/US2014/026324.
International Search Report and Written Opinion dated Jul. 18, 2014 from corresponding PCT Application No. PCT/US2014/026324, which was filed on Mar. 13, 2014.
International Preliminary Report on Patentability from PCT Application No. PCT/US2020/049885, dated Mar. 24, 2022.
International Preliminary Report on Patentability from PCT Application No. PCT/US2021/022321, dated Sep. 29, 2022.
International Preliminary Report on Patentability from PCT Application No. PCT/US2021/022421, dated Sep. 29, 2022.
International Preliminary Report on Patentability from PCT Application No. PCT/US2021/029963, dated Nov. 10, 2022.
International Preliminary Report on Patentability from PCT Application No. PCT/US2021/030210, dated Nov. 10, 2022.
International Preliminary Report on Patentability from PCT Application No. PCT/US2021/035273, dated Dec. 15, 2022.
International Preliminary Report on Patentability from PCT Application No. PCT/US2021/037623, dated Dec. 29, 2022.
International Preliminary Report on Patentability from PCT Application No. PCT/US2021/045298, dated Feb. 23, 2023.
International Preliminary Report on Patentability from PCT Application No. PCT/US2021/045689, dated Feb. 23, 2023.
International Preliminary Report on Patentability from PCT Application No. PCT/US2021/061201, dated Jun. 15, 2023.
ISR dated Aug. 19, 2022 from PCT/US2022/017812.
PCT Application No. PCT/US2023/025159 entitled "Disinfecting Cap For Fluid Path Element", filed Jun. 13, 2023.
UN Haluk, A New Device Preventing Air Embolism During The Angiography, Air Trap Device: An In-Vitro Experimental Air Emboli Study, Proceedings of the 2019 Design of Medical Devices Conference, 2019.

* cited by examiner

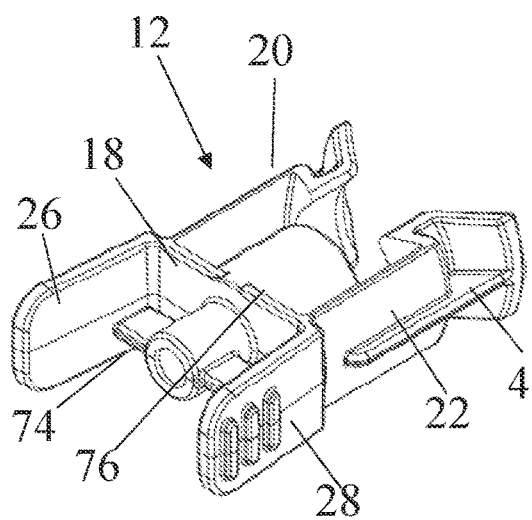
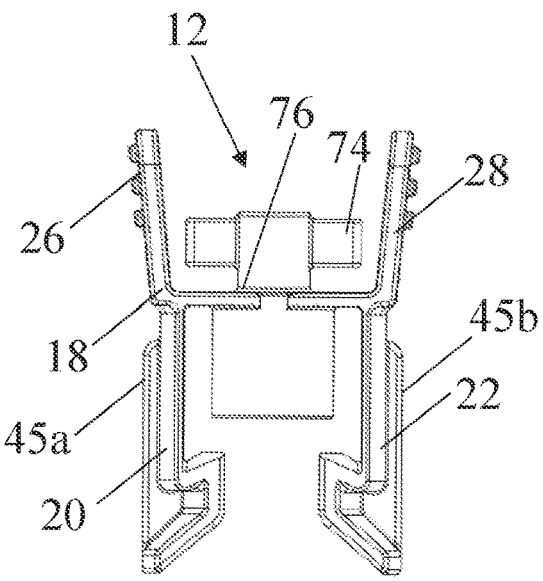
Fig. 13    Fig. 14
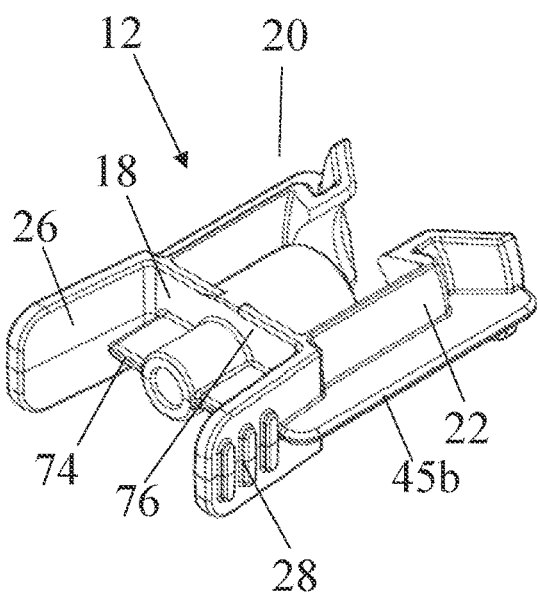
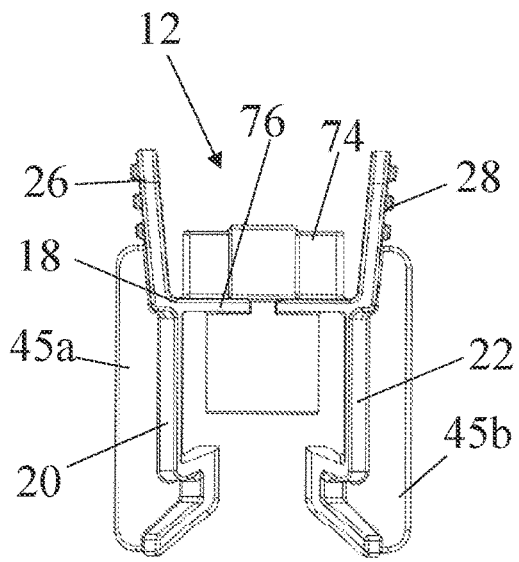
Fig. 15    Fig. 16

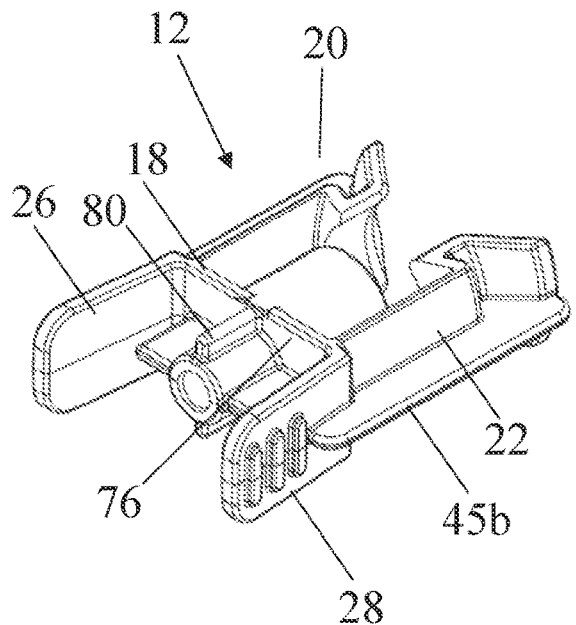
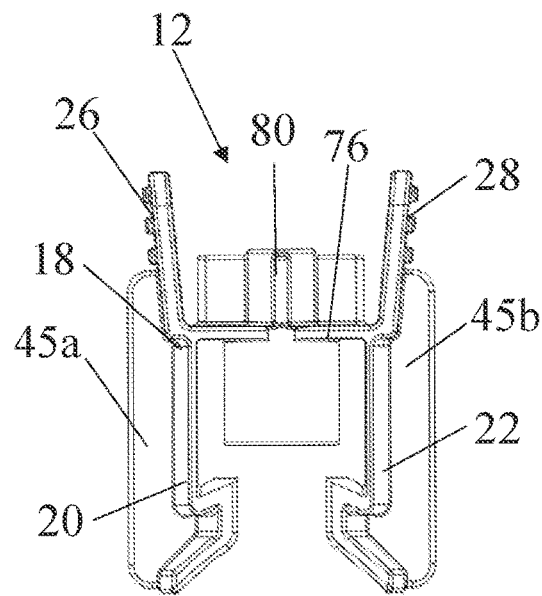
Fig. 17          Fig. 18
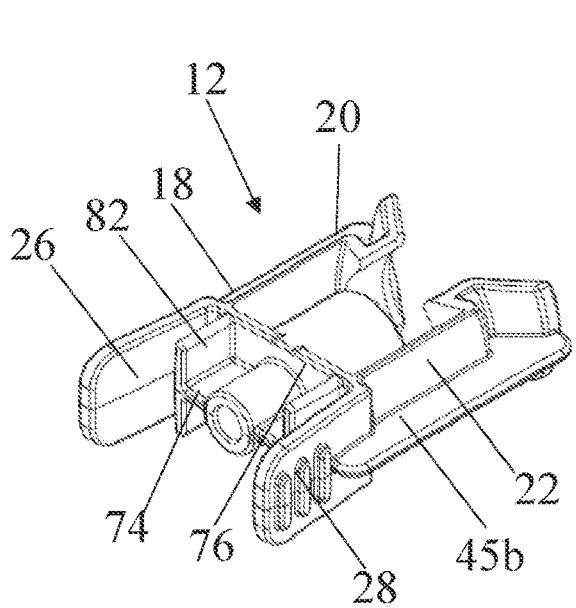
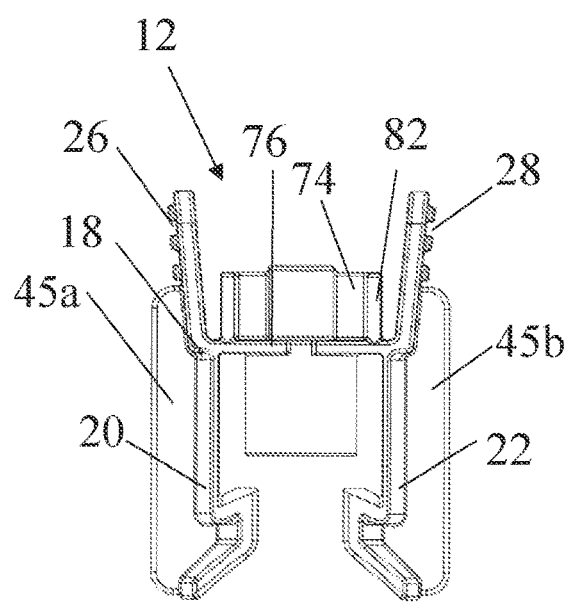
Fig. 19          Fig. 20

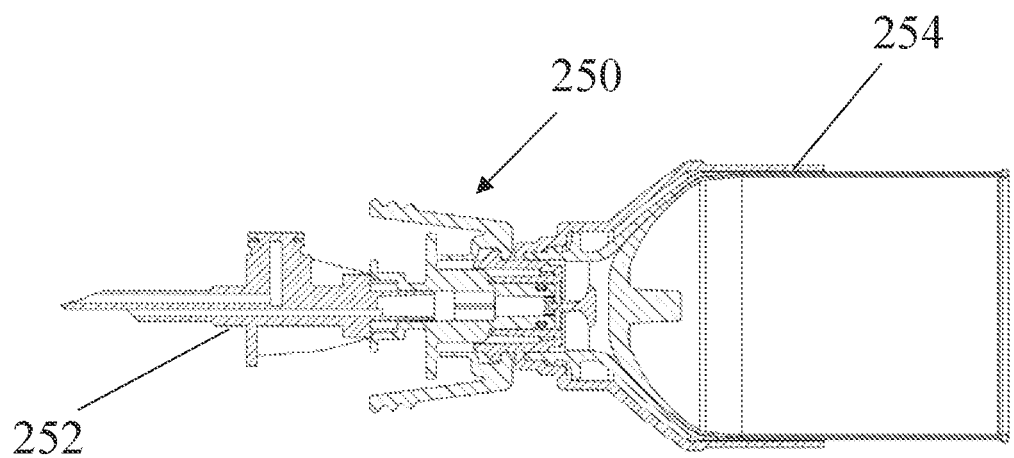
Fig. 44
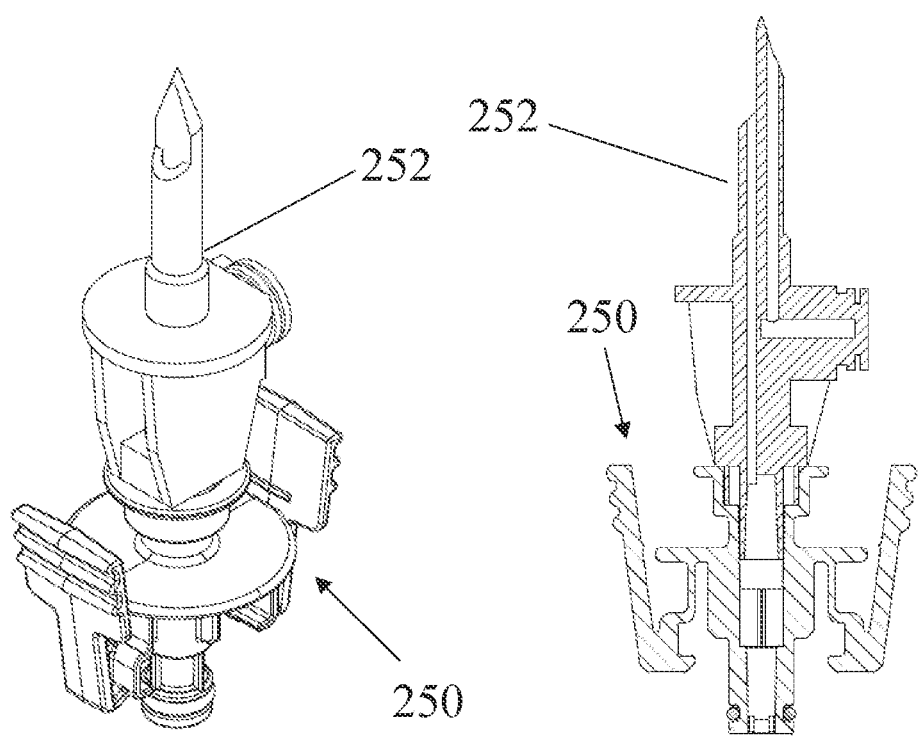
Fig. 45
Fig. 46

FLUID PATH CONNECTORS FOR MEDICAL FLUID DELIVERY

CROSS REFERENCE TO RELATED APPLICATIONS

This application is a U.S. national phase application under 35 U.S.C. § 371 of PCT International Application No. PCT/US2021/018523, filed Feb. 18, 2021, and claims the benefit of U.S. Provisional Patent Application No. 62/705,251, filed Jun. 18, 2020, and U.S. Provisional Patent Application No. 62/979,584, filed Feb. 21, 2020, the disclosures of each of which are incorporated by reference in their entirety.

BACKGROUND OF THE INVENTION

Field of the Invention

The present disclosure relates connectors, syringes, and syringe and connector systems for use in fluid delivery systems, and, especially, to connectors, syringes, and syringe and connector systems for use in medical fluid delivery systems in which one or more fluids are delivered to a patient under time constraints.

Description of Related Art

In many medical procedures, such as drug delivery, it is desirable to inject a liquid into a patient. Numerous types of liquids, such as contrast media (often referred to simply as "contrast") and/or saline, may be injected into a patient during diagnostic and therapeutic procedures. In some medical procedures, for example, angiography, computed tomography (CT), ultrasound, magnetic resonance imaging (MRI), nuclear medicine, and positron emission tomography (PET), it is necessary to deliver a liquid, such as contrast, in a timed fashion under high pressure. Injectors suitable for these applications typically use a relatively large volume syringe and are capable of producing relatively large flow rates.

Medical personnel work under increasingly difficult time and physical constraints. Thus, it is desirable to fill syringes or other liquid containers and to connect and disconnect fluid delivery system components as quickly as possible. However, filling a large syringe with liquid, such as a contrast medium or saline, is typically a time consuming process. Conventional syringes have a distal opening that is typically used for filling the interior of the syringe with liquid. The size of this distal opening places significant constraints on the filling rate. Further, since conventional syringes are typically shipped with the plunger in the fully retracted position, filling a syringe first requires moving the plunger to a distal end of the syringe to eject air from the syringe and start the liquid filling process. Since the cost of many medical processes, such as diagnostic imaging, increases in relation to duration, any delays can significantly increase cost.

Furthermore, in many such fluid delivery systems, it is necessary to form a fluid connection between separate fluid path components. For example, it may be necessary to connect an injector-powered syringe to flexible plastic tubing that, in turn, is connected to a spike connected to a bulk fluid source or catheter inserted into a patient. A common connector used in the medical arts is the luer connector or luer lock. The luer connector includes a male connector or member and a female connector or member. The male member and female member are typically connected via a friction fit or a radially inwardly projecting threading attached to the female member, which cooperates with one or more radially outwardly extending flanges on the male luer member to create a leak-free connection.

Many fluid connectors for use in medical procedures, including luer connectors, exhibit drawbacks, not the least of which include fragility, breakability (for example, from over tightening), and difficulty in forming a connection, for example by taking the time to rotate one or both connectors. Because medical personnel are under increasingly difficult time and physical constraints during various medical procedures, quite often, many fluid path elements must be connected and/or disconnected in a relatively short time under stressed and/or emergency conditions. This may lead to over-tightening of the luer connector which can compromise the structural integrity of the connector and even crack the connector components, leading to leakage and potential ingress of air. With many conventional connector configurations, there is no indication (audible or visual) that indicates to the user that the connectors are suitably assembled and further tightening is unnecessary. Additionally, the seal between the male member and the female member of the luer connector may be compromised due to tolerance stacking between the male member and the female member due to variances in the manufacturing process. Further, in certain procedures such as angiography, very high fluid pressures (up to 1200 psi) are used to inject fluid. The high pressure may lead to disconnection of conventional luer connectors, for example, unscrewing of the luer, such as when the male and/or female connector is wet resulting in reduced friction between the connector components.

Medical personnel must connect and/or disconnect fluid delivery systems in a relatively short time and under stressed and/or emergency conditions. It is thus desirable to develop syringe adapters that are configured for filling a syringe and/or deliver a medical fluid to a patient that have durable syringe and connector interfaces capable of connecting or disconnecting simply and quickly without leaking, breaking, or inadvertently disconnecting.

SUMMARY OF THE DISCLOSURE

In one example of the present disclosure, a fluid path connector for a medical fluid delivery system may include a first connector element including a body, a first lumen, a first flexible leg, and a second flexible leg; and a second connector element including a body defining an undercut, a second lumen, a channel defined in the body, and at least one sealing element positioned within the channel, wherein the first flexible leg includes a first flange and the second flexible leg includes a second flange, wherein, upon engagement of the first connector element with the second connector element, the first flange and the second flange engage with the undercut of the body of the second connector element to prevent disengagement of the first connector element and the second connector element, and wherein the sealing element is configured to define a fluid tight seal between the second lumen of the second connector element and the first lumen of the first connector element to form a fluid path when the first connector element and second connector element are engaged with one another.

In another example of the present disclosure, the first connector element and the second connector element are each in fluid communication with a fluid element selected from the group consisting of a syringe, a spike member, a fluid tube set, and a bulk fluid container. The first flange and the second flange are each angled inwardly towards a longitudinal axis of the first connector element. The first flange and the second flange are each angled at 45-75 degrees relative to a longitudinal axis of the first connector element. The first connector element includes a first actuating arm associated with the first flexible leg and a second actuating arm associated with the second flexible leg, and wherein, upon applying an inwardly-directed pressure to the first actuating arm and the second actuating arm, the first flexible leg and the second flexible leg move in an outward direction relative to the body of the second connector element to disengage the first flange and the second flange from the undercut to allow the first connector element and the second connector element to be disengaged. At least one of the first flexible leg and the second flexible leg includes at least one reinforcing rib. When the first connector element and the second connector element are connected to one another, the first connector element and the second connector element are configured to withstand a fluid pressure in the fluid path of at least 800 psi. The first connector element further includes a support base that extends from the body between the first flexible leg and the second flexible leg, and wherein the support base is configured to reduce deflection of the body due to a fluid pressure exerted by a fluid moving through the fluid path. The support base includes at least one reinforcing rib to reduce deflection of the body due to the fluid pressure exerted by the fluid moving through the fluid path. The sealing element is one of the following: an elastomeric O-ring, an overmolded sealing surface, and a quad ring. The channel is dimensioned such that the at least one sealing element moves along a longitudinal axis of the second connector element in opposite directions within the channel when the first connector element and the second connector element are engaged and disengaged from one another. The at least sealing element moves between a first position in which the at least one sealing member seals a fluid channel defined in the second connector element to prevent the fluid from flowing through the second connector element and a second position in which the at least one sealing member is moved out of the fluid channel to permit the fluid to flow through the second connector element. At least one of the first connector element and the second connector element further includes a skirt that surrounds the body of the first connector element and the body of the second connector element. The skirt extends beyond a distal end of the body of at least one of the first connector element and the second connector element. At least one aperture is defined in the skirt for the second connector element. At least one of the first connector element and the second connector element further includes a fluid path adaptor configured for connecting the at least one of the first connector element and the second connector element to a fluid delivery element. The first connector element includes a slidable sleeve configured to lock the first and second flexible arms when the first connector element is engaged with the second connector element.

In another example of the present disclosure, a medical fluid delivery system includes a syringe including a proximal end, a distal end, and a sidewall extending from the proximal end to the distal end, a fluid delivery member, and a fluid path connector, including a first connector element including a body, a first lumen, a first flexible leg, and a second flexible leg; and a second connector element including a body defining an undercut, a second lumen, a channel defined in the body, and at least one sealing element positioned within the channel, wherein the first connector element is fluidly connected to the fluid delivery member, wherein the second connector element is fluidly connected to the distal end of the syringe, wherein the first flexible leg includes a first flange and the second flexible leg includes a second flange, wherein, upon engagement of the first connector element with the second connector element, the first flange and the second flange engage with the undercut of the body of the second connector element to prevent disengagement of the first connector element and the second connector element, and wherein the sealing element is configured to define a fluid tight seal between the second lumen of the second connector element and the first lumen of the first connector element to form a fluid path when the first connector element and the second connector element are engaged with one another.

In another example of the present disclosure, the first connector element and the second connector element are each in fluid communication with a fluid element selected from the group consisting of a syringe, a spike member, a fluid tube set, and a bulk fluid container. The first flange and the second flange are each angled inwardly towards a longitudinal axis of the first connector element. The first flange and the second flange are each angled at 45-75 degrees relative to a longitudinal axis of the first connector element. The first connector element including a first actuating arm associated with the first flexible leg and a second actuating arm associated with the second flexible leg, and wherein, upon applying an inwardly-directed pressure to the first actuating arm and the second actuating arm, the first flexible leg and the second flexible leg move in an outward direction relative to the body of the second connector element to disengage the first flange and the second flange from the undercut to allow the first connector element and the second connector element to be disengaged. At least one of the first flexible leg and the second flexible leg include at least one reinforcing rib. When the first connector element and the second connector element are connected to one another, the first connector element and the second connector element are configured to withstand up a fluid pressure in the fluid path of at least 800 psi. The first connector element further includes a support base that extends from the body between the first flexible leg and the second flexible leg, and wherein the support base is configured to reduce deflection of the body due to a fluid pressure exerted by a fluid moving through the fluid path. The support base includes at least one reinforcing rib to reduce deflection of the body due to the fluid pressure exerted by the fluid moving through the fluid path. The channel is dimensioned such that the sealing element moves along a longitudinal axis of the second connector element in opposite directions within the channel when the first connector element and the second connector element are engaged and disengaged from one another. At least one of the first connector element and the second connector element further includes a skirt that surrounds the body of the first connector element and the body of the second connector element. The skirt extends beyond a distal end of the body of at least one of the first connector element and the second connector element. At least one aperture is defined in the skirt for the second connector element. At least one of the first connector element and the second connector element further includes a fluid path adaptor configured for connecting the at least one of the first connector element and the second connector element to a fluid delivery element. The first connector element includes a slidable sleeve configured to lock the first and second flexible arms when the first connector element is engaged with the second connector element.

In another example of the present disclosure, a fluid path connector for a medical fluid delivery system, the fluid path connector including a first connector element including a body defining a first undercut, a first flexible leg, and a second flexible leg; and a second connector element including a body defining a second undercut, a third flexible leg, and a fourth flexible leg, wherein the first flexible leg includes a first flange, the second flexible leg defines a second flange, the third flexible leg includes a third flange, and the fourth flexible leg defines a fourth flange, and wherein, upon engagement of the first connector element with the second connector element, the first flange and the second flange link into the second undercut of the body of the second connector element and the third flange and the fourth flange link into the first undercut of the body of the first connector element to ensure the first connector element and the second connector element are prevented from disengaging with one another.

In another example of the present disclosure, the first flange and the second flange are each angled inwardly towards a longitudinal axis of the first connector element, and wherein the third flange and the fourth flange are each angled inwardly towards a longitudinal axis of the second connector element. The first flange and the second flange are each angled at 45-75 degrees relative to a longitudinal axis of the first connector element, and wherein the third flange and the fourth flange are each angled at 45-75 degrees relative to a longitudinal axis of the second connector element. The first connector element further includes a first actuating arm and a second actuating arm, wherein the second connector element further includes a third actuating arm and a fourth actuating arm, wherein, upon applying an inwardly-directed pressure to the first actuating arm and the second actuating arm, the first flexible leg and the second flexible leg move in an outward direction relative to the body of the second connector element to allow the first connector element and the second connector element to be disengaged, and wherein, upon applying an inwardly-directed pressure to the third actuating arm and the fourth actuating arm, the third flexible leg and the fourth flexible leg move in an outward direction relative to the body of the second connector element to allow the first connector element and the second connector element to be disengaged. At least one of the first actuating arm, the second actuating arm, the third actuating arm, and the fourth actuating arm include at least one reinforcing rib. When the first connector element and the second connector element are connected to one another, the first connector element and the second connector element are configured to withstand up a fluid pressure of at least 800 psi.

The following clauses also recite further features of the present disclosure:

Clause 1: A fluid path connector for a medical fluid delivery system, the fluid path connector comprising a first connector element comprising a body, a first lumen, a first flexible leg, and a second flexible leg; and a second connector element comprising a body defining an undercut, a second lumen, a channel defined in the body, and at least one sealing element positioned within the channel, wherein the first flexible leg includes a first flange and the second flexible leg includes a second flange, wherein, upon engagement of the first connector element with the second connector element, the first flange and the second flange engage with the undercut of the body of the second connector element to prevent disengagement of the first connector element and the second connector element, and wherein the sealing element is configured to define a fluid tight seal between the second lumen of the second connector element and the first lumen of the first connector element to form a fluid path when the first connector element and the second connector element are engaged with one another.

Clause 2: The fluid path connector of Clause 1, wherein the first connector element and the second connector element are each in fluid communication with a fluid element selected from the group consisting of a syringe, a spike member, a fluid tube set, and a bulk fluid container.

Clause 3: The fluid path connector of Clause 1 or 2, wherein the first flange and the second flange are each angled inwardly towards a longitudinal axis of the first connector element.

Clause 4: The fluid path connector of any of Clauses 1-3, wherein the first flange and the second flange are each angled at 45-75 degrees relative to a longitudinal axis of the first connector element.

Clause 5: The fluid path connector of any of Clauses 1-4, the first connector element comprising a first actuating arm associated with the first flexible leg and a second actuating arm associated with the second flexible leg, and wherein, upon applying an inwardly-directed pressure to the first actuating arm and the second actuating arm, the first flexible leg and the second flexible leg move in an outward direction relative to the body of the second connector element to disengage the first flange and the second flange from the undercut to allow the first connector element and the second connector element to be disengaged.

Clause 6: The fluid path connector of Clause 5, wherein at least one of the first flexible leg and the second flexible leg include at least one reinforcing rib.

Clause 7: The fluid path connector of any of Clauses 1-6, wherein, when the first connector element and the second connector element are connected to one another, the first connector element and the second connector element are configured to withstand a fluid pressure in the fluid path of at least 800 psi.

Clause 8: The fluid path connector of any of Clauses 1-7, wherein the first connector element further comprises a support base that extends from the body between the first flexible leg and the second flexible leg, and wherein the support base is configured to reduce deflection of the body due to a fluid pressure exerted by a fluid moving through the fluid path.

Clause 9: The fluid path connector of Clause 8, wherein the support base comprises at least one reinforcing rib to reduce deflection of the body due to the fluid pressure exerted by the fluid moving through the fluid path.

Clause 10: The fluid path connector of any of Clauses 1-9, wherein the sealing element is one of the following: an elastomeric O-ring, an overmolded sealing surface, and a quad ring.

Clause 11: The fluid path connector of any of Clauses 1-10, wherein the channel is dimensioned such that the at least one sealing element moves along a longitudinal axis of the second connector element in opposite directions within the channel when the first connector element and the second connector element are engaged and disengaged from one another.

Clause 12: The fluid path connector of any of Clauses 1-11, wherein the at least sealing element moves between a first position in which the at least one sealing member seals a fluid channel defined in the second connector element to prevent the fluid from flowing through the second connector element and a second position in which the at least one sealing member is moved out of the fluid channel to permit the fluid to flow through the second connector element.

Clause 13: The fluid path connector of any of Clauses 1-12, wherein at least one of the first connector element and the second connector element further comprises a skirt that surrounds the body of the first connector element and the body of the second connector element.

Clause 14: The fluid path connector of Clause 13, wherein the skirt extends beyond a distal end of the body of at least one of the first connector element and the second connector element.

Clause 15: The fluid path connector of Clause 13 or 14, wherein at least one aperture is defined in the skirt for the second connector element.

Clause 16: The fluid path connector of any of Clauses 1-15, wherein at least one of the first connector element and the second connector element further comprises a fluid path adaptor configured for connecting the at least one of the first connector element and the second connector element to a fluid delivery element.

Clause 17: The fluid path connector of any of Clauses 1-16, wherein the first connector element comprises a slidable sleeve configured to lock the first and second flexible arms when the first connector element is engaged with the second connector element.

Clause 18: A medical fluid delivery system, comprising a syringe comprising a proximal end, a distal end, and a sidewall extending from the proximal end to the distal end; a fluid delivery member; and a fluid path connector, comprising a first connector element comprising a body, a first lumen, a first flexible leg, and a second flexible leg; and a second connector element comprising a body defining an undercut, a second lumen, a channel defined in the body, and at least one sealing element positioned within the channel, wherein the first connector element is fluidly connected to the fluid delivery member, wherein the second connector element is fluidly connected to the distal end of the syringe, wherein the first flexible leg comprises a first flange and the second flexible leg comprises a second flange, wherein, upon engagement of the first connector element with the second connector element, the first flange and the second flange engage with the undercut of the body of the second connector element to prevent disengagement of the first connector element and the second connector element, and wherein the sealing element is configured to define a fluid tight seal between the second lumen of the second connector element and the first lumen of the first connector element to form a fluid path when the first connector element and the second connector element are engaged with one another.

Clause 19: The medical fluid delivery system of Clause 18, wherein the first connector element and the second connector element are each in fluid communication with a fluid element selected from the group consisting of a syringe, a spike member, a fluid tube set, and a bulk fluid container.

Clause 20: The medical fluid delivery system of Clause 18 or 19, wherein the first flange and the second flange are each angled inwardly towards a longitudinal axis of the first connector element.

Clause 21: The medical fluid delivery system of any of Clauses 18-20, wherein the first flange and the second flange are each angled at 45-75 degrees relative to a longitudinal axis of the first connector element.

Clause 22: The medical fluid delivery system of any of Clauses 18-21, the first connector element comprising a first actuating arm associated with the first flexible leg and a second actuating arm associated with the second flexible leg, and wherein, upon applying an inwardly-directed pressure to the first actuating arm and the second actuating arm, the first flexible leg and the second flexible leg move in an outward direction relative to the body of the second connector element to disengage the first flange and the second flange from the undercut to allow the first connector element and the second connector element to be disengaged.

Clause 23: The medical fluid delivery system of Clause 22, wherein at least one of the first flexible leg and the second flexible leg include at least one reinforcing rib.

Clause 24: The medical fluid delivery system of any of Clauses 18-23, wherein, when the first connector element and the second connector element are connected to one another, the first connector element and the second connector element are configured to withstand up a fluid pressure in the fluid path of at least 800 psi.

Clause 25: The medical fluid delivery system of any of Clauses 18-24, wherein the first connector element further comprises a support base that extends from the body between the first flexible leg and the second flexible leg, and wherein the support base is configured to reduce deflection of the body due to a fluid pressure exerted by a fluid moving through the fluid path.

Clause 26: The medical fluid delivery system of Clause 25, wherein the support base comprises at least one reinforcing rib to reduce deflection of the body due to the fluid pressure exerted by the fluid moving through the fluid path.

Clause 27: The medical fluid delivery system of any of Clauses 18-26, wherein the channel is dimensioned such that the sealing element moves along a longitudinal axis of the second connector element in opposite directions within the channel when the first connector element and the second connector element are engaged and disengaged from one another.

Clause 28: The medical fluid delivery system of any of Clauses 18-27, wherein at least one of the first connector element and the second connector element further comprises a skirt that surrounds the body of the first connector element and the body of the second connector element.

Clause 29: The medical fluid delivery system of Clause 28, wherein the skirt extends beyond a distal end of the body of at least one of the first connector element and the second connector element.

Clause 30: The medical fluid delivery system of Clause 28 or 29, wherein at least one aperture is defined in the skirt for the second connector element.

Clause 31: The medical fluid delivery system of any of Clauses 18-30, wherein at least one of the first connector element and the second connector element further comprises a fluid path adaptor configured for connecting the at least one of the first connector element and the second connector element to a fluid delivery element.

Clause 32: The medical fluid delivery system of any of Clauses 18-31, wherein the first connector element comprises a slidable sleeve configured to lock the first and second flexible arms when the first connector element is engaged with the second connector element.

Clause 33: A fluid path connector for a medical fluid delivery system, the fluid path connector comprising a first connector element comprising a body defining a first undercut, a first flexible leg, and a second flexible leg; and a second connector element comprising a body defining a second undercut, a third flexible leg, and a fourth flexible leg, wherein the first flexible leg comprises a first flange, the second flexible leg defines a second flange, the third flexible leg comprises a third flange, and the fourth flexible leg defines a fourth flange, and wherein, upon engagement of the first connector element with the second connector element, the first flange and the second flange link into the second undercut of the body of the second connector element and the third flange and the fourth flange link into the first undercut of the body of the first connector element to ensure the first connector element and the second connector element are prevented from disengaging with one another.

Clause 34: The fluid path connector of Clause 33, wherein the first flange and the second flange are each angled inwardly towards a longitudinal axis of the first connector element, and wherein the third flange and the fourth flange are each angled inwardly towards a longitudinal axis of the second connector element.

Clause 35: The fluid path connector of Clause 33 or 34, wherein the first flange and the second flange are each angled at 45-75 degrees relative to a longitudinal axis of the first connector element, and wherein the third flange and the fourth flange are each angled at 45-75 degrees relative to a longitudinal axis of the second connector element.

Clause 36: The fluid path connector of any of Clauses 33-35, wherein the first connector element further comprises a first actuating arm and a second actuating arm, wherein the second connector element further comprises a third actuating arm and a fourth actuating arm, wherein, upon applying an inwardly-directed pressure to the first actuating arm and the second actuating arm, the first flexible leg and the second flexible leg move in an outward direction relative to the body of the second connector element to allow the first connector element and the second connector element to be disengaged, and wherein, upon applying an inwardly-directed pressure to the third actuating arm and the fourth actuating arm, the third flexible leg and the fourth flexible leg move in an outward direction relative to the body of the second connector element to allow the first connector element and the second connector element to be disengaged.

Clause 37: The fluid path connector of Clause 36, wherein at least one of the first actuating arm, the second actuating arm, the third actuating arm, and the fourth actuating arm include at least one reinforcing rib.

Clause 38: The fluid path connector of any of Clauses 33-37, wherein, when the first connector element and the second connector element are connected to one another, the first connector element and the second connector element are configured to withstand up a fluid pressure of at least 800 psi.

BRIEF DESCRIPTION OF THE DRAWINGS

FIG. 13 is a perspective view of a connector element including reinforcing members according to one example of the present disclosure;

FIG. 14 is a side view of the connector element of FIG. 13;

FIG. 15 is a perspective view of a connector element including reinforcing members according to another example of the present disclosure;

FIG. 16 is a side view of the connector element of FIG. 15;

FIG. 17 is a perspective view of a connector element including reinforcing members according to another example of the present disclosure;

FIG. 18 is a side view of the connector element of FIG. 17;

FIG. 19 is a perspective view of a connector element including reinforcing members according to another example of the present disclosure;

FIG. 20 is a side view of the connector element of FIG. 19;

FIG. 44 is a cross-sectional view of the fluid path connector assembly of FIG. 43;

FIG. 45 is a perspective view of the fluid path connector spike assembly of FIG. 43;

FIG. 46 is a cross-sectional view of fluid path connector spike assembly of FIG. 43;

DESCRIPTION OF THE DISCLOSURE

Figure 1:
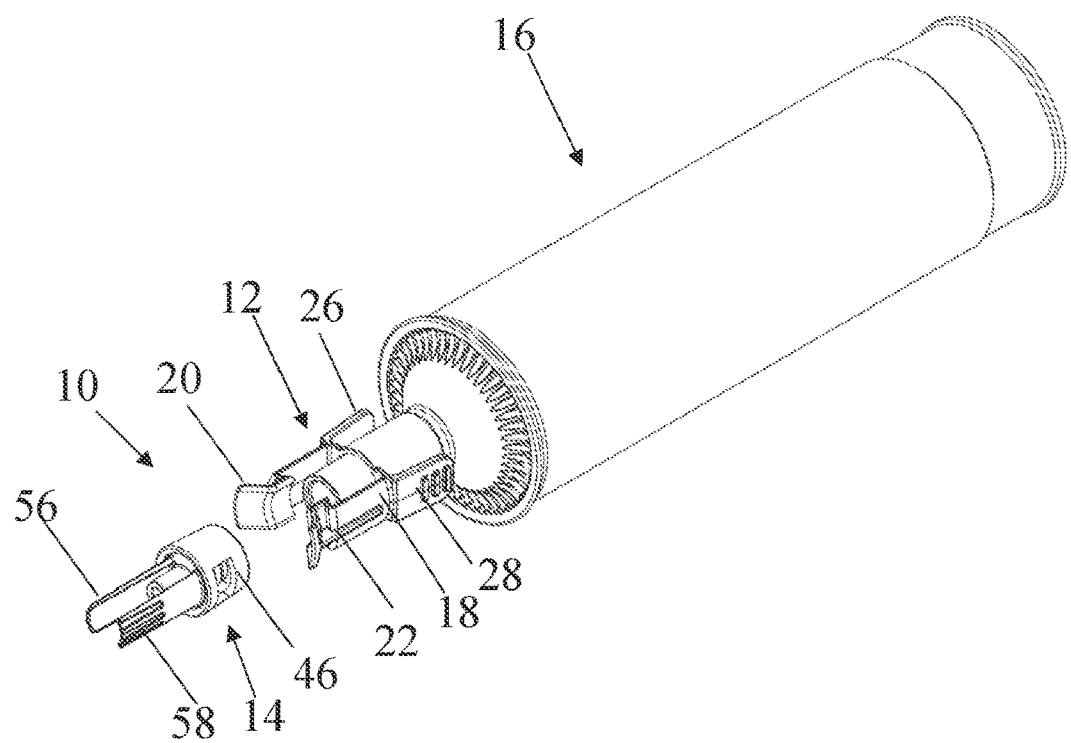
FIG. 1 is a perspective view of a fluid path connector assembly associated with a syringe according to one example of the present disclosure shown in a disconnected position.
Figure 2:
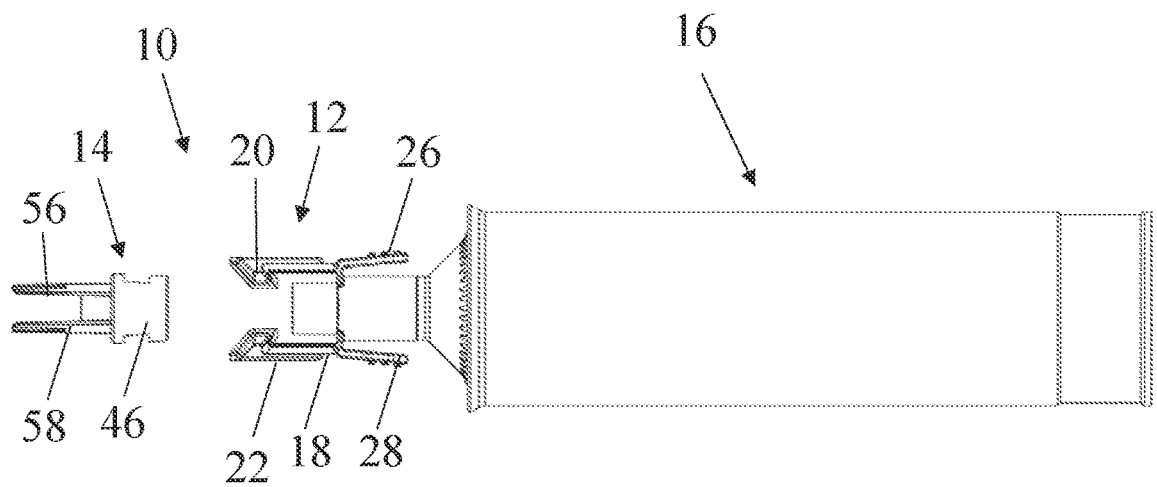
FIG. 2 is a side view of the fluid path connector assembly of FIG. 1 in the disconnected position.
Figure 3:
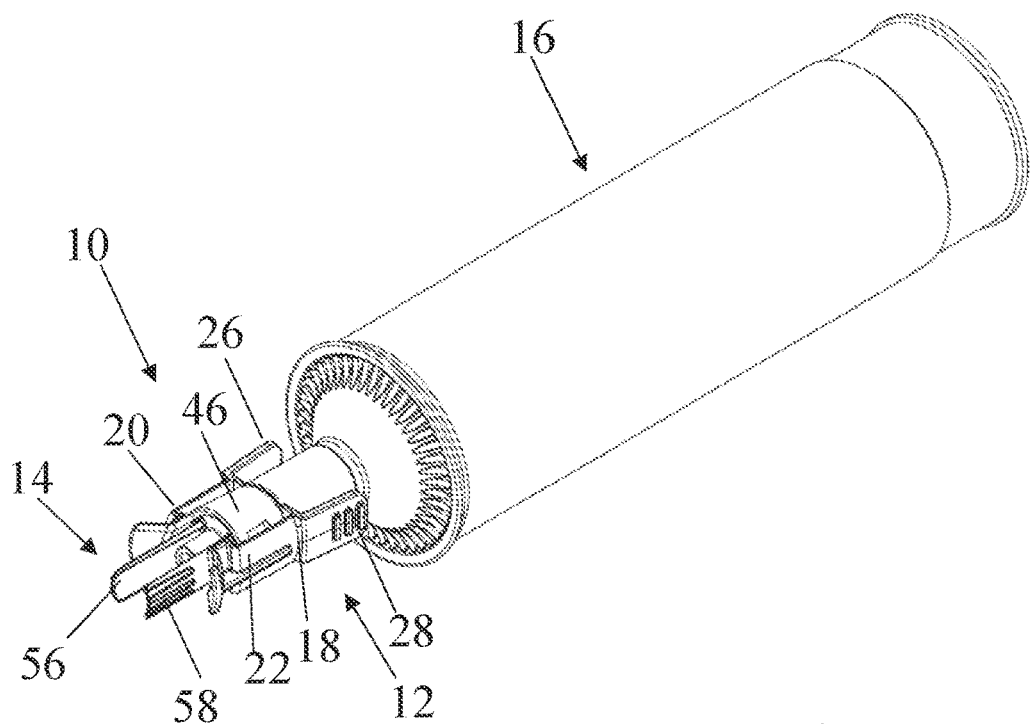
FIG. 3 is a perspective view of the fluid path connector assembly of FIG. 1 in a connected position.
Figure 4:
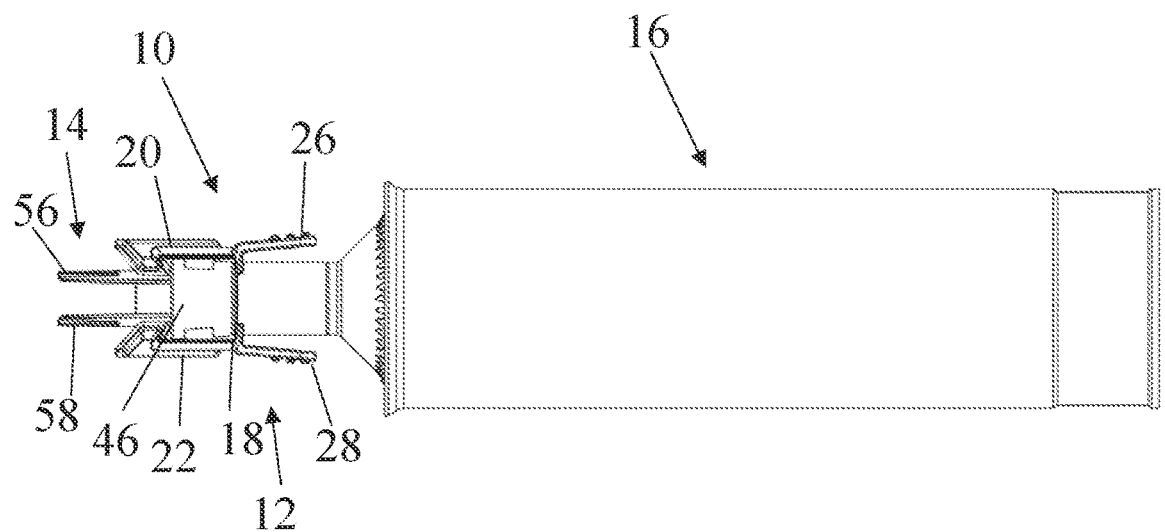
FIG. 4 is a side view of the fluid path connector assembly of FIG. 1 in the connected position.

The illustrations generally show preferred and non-limiting aspects of the systems and methods of the present disclosure. While the description presents various aspects of the devices, it should not be interpreted in any way as limiting the disclosure. Furthermore, modifications, concepts, and applications of the disclosure's aspects are to be interpreted by those skilled in the art as being encompassed, but not limited to, the illustrations and description provided herein.

The following description is provided to enable those skilled in the art to make and use the described aspects contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure. Further, for purposes of the description hereinafter, the terms "end", "upper", "lower", "right", "left", "vertical", "horizontal", "top", "bottom", "lateral", "longitudinal", and derivatives thereof shall relate to the disclosure as it is oriented in the figures. The term "proximal" in relation to a syringe refers generally to an axial or a longitudinal direction toward the end of a syringe nearest the injector and opposite the tubing towards the patient. The term "distal" in relation to a syringe refers generally to an axial or a longitudinal direction away from the injector and towards the patient. The term "proximal" in relation to a tubing set refers generally to an axial or a longitudinal direction toward the end of a tubing set nearest the syringe and opposite the injection member towards the patient. The term "distal" in relation to a tubing set refers generally to an axial or a longitudinal direction away from the syringe and towards the injection member of the patient. The term "radial" and related terms refers generally to a direction normal to a longitudinal axis of a syringe. However, it is to be understood that the disclosure may assume various alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting.

FIGS. 1-6 illustrate a fluid path connector assembly 10 associated with a syringe 16 according to one example of the present disclosure. The fluid path connector assembly 10 may include a first connector element 12 and a second connector element 14 that are configured to connect to one another to create a liquid-tight seal between a first fluid container and a second fluid container or fluid delivery device. In one example of the present disclosure, the first connector element 12 may be operatively connected to a syringe 16. The first connector element 12 may be operatively connected to a distal end of the syringe 16. In one example of the present disclosure, the first connector element 12 may be welded (for example, laser welded) or otherwise adhered to the distal end of the syringe 16. In some examples of the present disclosure, the second connector element 14 may be connected to a catheter tubing set, a fluid delivery line, a fluid spike assembly, or any medical fluid container with an opening. In one example of the present disclosure, an inner surface of a distal tip of the syringe 16 may include a plurality of ribs 17 that create a contour in the syringe 16 that takes advantage of a Coanda effect for the fluid passing through the syringe 16, in combination with a flow diverter 53 as shown in FIGS. 6A-6C. As used herein, the Coanda effect is the tendency for a liquid stream to be attracted to a nearby curved or angled surface as the liquid flows along the surface. Thus, as fluid enters the syringe 16 through the connector element, the fluid contacts the flow diverter 53 and is diverted towards the inner walls of the discharge neck of the syringe 16 to contact the plurality of ribs 17. As liquid flows along the ribbed distal tip of the syringe 16, it is naturally attracted to the inside surface of the conical distal end of the syringe 16, rather than dripping from the edge of the ribbed distal tip of the syringe 16. The liquid then flows down a tubular sidewall of the syringe 16, ultimately accumulating at the bottom of the syringe 16, filling syringe 16 from the bottom up as air escapes the syringe 16 through a flow controller and connector tube. This flow along the inside surface of the syringe 16 helps to reduce turbulence as the liquid fills the syringe 16, which aides in reducing air bubbles from forming as the syringe 16 is filled. Further, the flow diverter 53 and the ribs 17 allow for more rapid filling of the syringe 16, thereby reducing the duration of the fluid injection process. Further features and advantages of this Coanda effect are described in WO2017/091643, the disclosure of which is incorporated by reference in its entirety. It should be noted that, while FIG. 1 and other figures illustrate the syringe 16 having the first connector element 12 with the second connector element 14 connected to a catheter tubing set, a fluid delivery line, a fluid spike assembly, or any medical fluid container with an opening, the position of the first connector element 12 with the second connector element 14 may be interchanged without deviating from the spirit of the present disclosure. Generally, the positions of the first connector element 12 with the second connector element 14 in the various configurations may be interchanged without deviating from the spirit of the present disclosure.

In some examples of the present disclosure, the first connector element 12 may include a body 18, a first lumen 19 extending through the body 18, a first leg 20, and a second leg 22 with a support base 76 connected to the first leg 20 and the second leg 22. The first and second legs 20, 22 may be formed integral with the body 18. The first and second legs 20, 22 may extend from the body 18 in a distal direction relative to the distal end of the syringe 16 as shown in FIGS. 1-6. In one example of the present disclosure, the first and second legs 20, 22 are made of a material such that they can pivot where the legs 20, 22 meet the support base 76 to allow the distal end of the first and second legs 20, 22 to move radially outward in a direction relative to a longitudinal axis 24 of the first connector element 12. In one example of the present disclosure, the first and second legs 20, 22 may be made of a rigid material with a flexible pivot point to allow the first and second legs 20, 22 to move radially outward in a direction relative to a longitudinal axis 24 of the first connector element 12.

In some examples of the present disclosure, the first connector element 12 may also include a first actuating arm 26 and a second actuating arm 28 that extend from the body 18 in a direction opposite to the first and second legs 20, 22. The first and second actuating arms 26, 28 may be formed integral with the body 18 and the first and second legs 20, 22. During operation of the fluid path connector assembly 10, the first and second actuating arms 26, 28 are configured to be pushed radially inwards towards one another by an operator to move the first and second legs 20, 22 radially outwardly away from one another. Pressure on the first and second actuating arms 26, 28 forces the first and second legs 20, 22 to move away from one another. In one embodiment of the present disclosure, at least one of the first and second actuating arms 26, 28 may include a plurality of gripping ribs 30 to assist in gripping the first and second actuating arms 26, 28 when handling the first connector element 12. In some examples of the present disclosure, the first connector element 12 may also include a support portion 32 that extends from the body 18 in the same direction as the first and second actuating arms 26, 28, that is, toward the body of the syringe 16 as shown in FIGS. 1-6. The support portion 32 may be formed integral with the body 18 and may define a channel configured to receive the distal end of the syringe 16. The support portion 32 may be connected to the distal end of the syringe 16, for example by a screw fit, adhesion, or welding. The support portion 32 provides a stabilizing effect to the first connector element 12 when the first connector element 12 is operatively connected to the syringe 16 and, further, when the first and second actuating arms 26, 28 are pressed inwardly towards one another to actuate the first connector element 12.

According to various examples of the present disclosure, each of the first and second legs 20, 22 may include a first flange 34 and a second flange 36, respectively, that are configured to engage with a portion of the second connector element 14, as described herein, to readily connect the first connector element 12 with the second connector element 14 in a manner to withstand pressures associated with a pressurized fluid injection procedure without disconnecting and to create the fluid-tight seal between the first lumen 19 of the first connector element 12 and a second lumen 47 of the second connector elements 14. In some examples of the present disclosure, at least a portion 38, 40 of each flange 34, 36, respectively, may be angled inwardly relative to the longitudinal axis 24 of the first connector element 12. In one example of the present disclosure, the portions 38, 40 of the flanges 34, 36 may be angled 60 degrees from the longitudinal axis 24 of the first connector element 12, where the angled portion is angled toward the proximal end of the syringe 16 as shown in FIGS. 1-6. In other examples of the present disclosure, the portions 38, 40 of the flanges 34, 36 may be angled ranging from 45 degrees and 75 degrees from the longitudinal axis 24 of the first connector element 12. In another example of the present disclosure, the portions 38, 40 of the flanges 34, 36 may be angled ranging from 55 degrees and 65 degrees from the longitudinal axis 24 of the first connector element 12. In one example of the present disclosure, the portions 38, 40 of the flanges 34, 36 may be pointed towards the distal end of the syringe 16 such that the portions 38, 40 of the flanges 34, 36 extend towards a proximal end of the syringe 16. Under fluid injection pressures, the angled portions 38, 40 of the flanges 34, 36 may force the first and second legs 20, 22 in a radially inward direction, thereby increasing the strength of the connection force between the first connector element 12 and the second connector element 14 during a pressurized injection and making disconnection unlikely. The distalmost surface 42, 44 of the flanges 34, 36 may be sloped or beveled to assist in receiving the second connector element 14, as described below. The surfaces 42, 44 may be angled inwardly towards the longitudinal axis 24 of the first connector element 12. In one example of the present disclosure, an outer edge of each surface 42, 44 may slope inwardly to an inner edge of each surface 42, 44 while sloping inwardly and in a direction towards the actuating arms 26, 28. The beveled or sloped surfaces 42, 44 flex the first and second legs 20, 22 radially outward during insertion of the second connector element 14 into the first connector element 12 and then the first and second legs 20, 22 snap back in a radially inward direction once the body 46 of the second connector element 14 passes the flanges 34, 36, thereby engaging the first connector element 12 with the second connector element 14.

According to various examples of the present disclosure, each of the legs 20, 22 may also include at least one reinforcing member 45a, 45b. According to various examples, the reinforcing members 45a, 45b may be provided along at least a portion of an outer surface of the legs 20, 22. In certain examples, the reinforcing members 45a, 45b may extend the entire length of the legs 20, 22. The reinforcing members 45a, 45b may be formed integral with the legs 20, 22, for example on an outer surface of the leg 20 or 22. The reinforcing members 45a, 45b may be made of a similar material as the legs 20, 22 and the first connector element 12, for example, by co-molding the leg 20, 22 with the respective reinforcing member 45a, 45b. In other examples, the reinforcing members 45a, 45b may be made of a different material than the legs 20, 22 and the first connector element 12 to increase the strength of the legs 20, 22. The reinforcing members 45a, 45b may be provided on the legs 20, 22 to add rigidity to the legs 20, 22 while still allowing the legs 20, 22 to retain sufficient flexibility to move inwardly and outwardly during connection and disconnection of the first connector element 12 and the second connector element 14. In one example of the present disclosure, the reinforcing members 45a, 45b may be strips of material that extend along at least a portion of the length of the legs 20, 22 and extend outwardly from an outer surface of the legs 20, 22, for example, substantially perpendicular to the outer surface of the legs 20, 22. After the first and second connector elements 12, 14 have been connected, the reinforcing members 45a, 45b may be configured to assist in maintaining the connection of the legs 20, 22 to the second connector element 14, for example by further reducing outward flexing or stretching of the legs 20, 22 during a pressurized injection procedure. Due to high fluid pressures between the first and second connector elements 12, 14, in certain embodiments, the first and second connector elements 12, 14 may have a tendency to flex radially outward from one another. Therefore, the reinforcing members 45a, 45b assist in ensuring that the legs 20, 22 do not move outwardly under these high fluid pressures, thereby preventing the first connector element 12 from disconnecting from the second connector element 14.

Figure 5A:
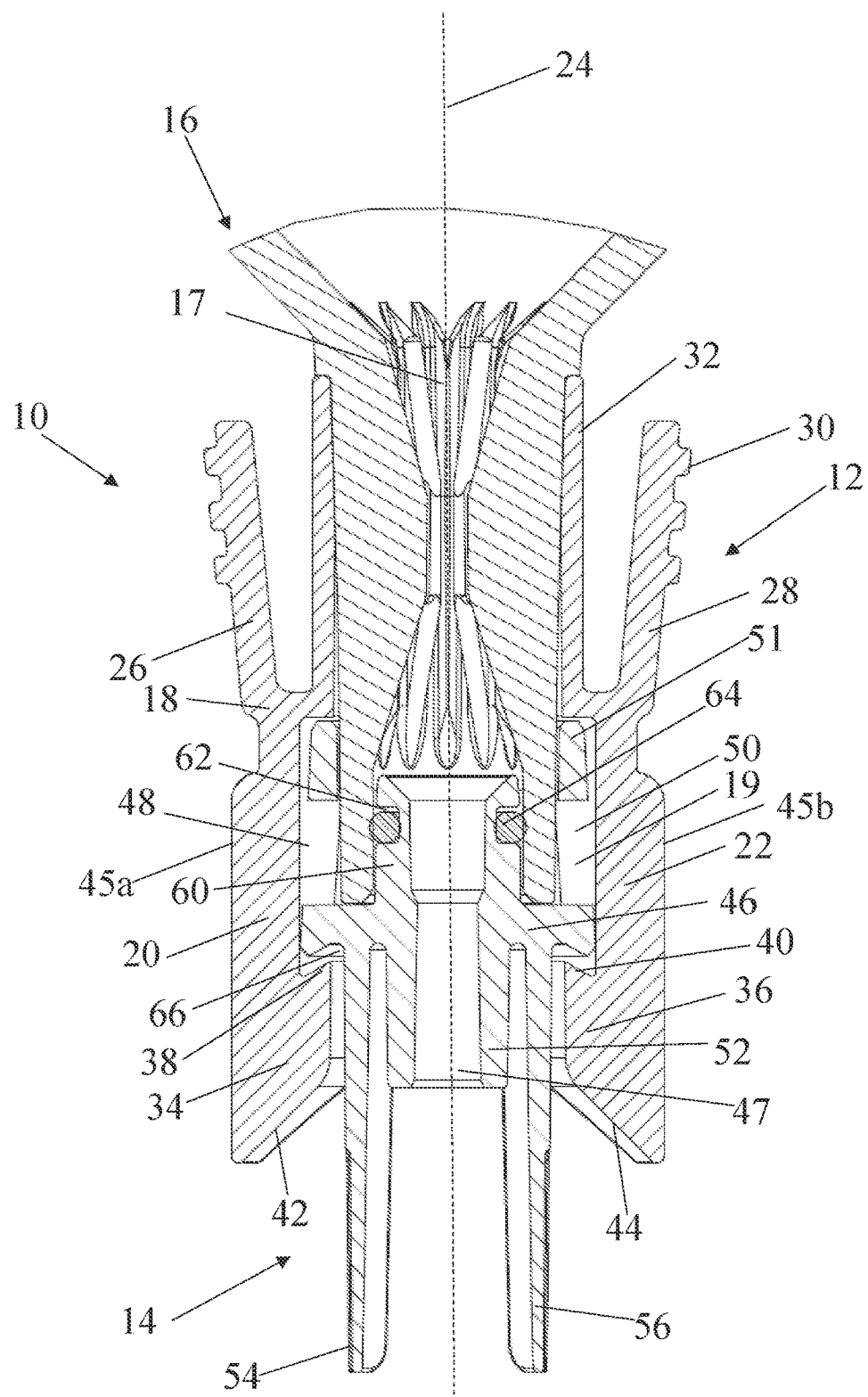
FIG. 5A is a cross-sectional view of the fluid path connector assembly of FIG. 1.
Figure 5B:
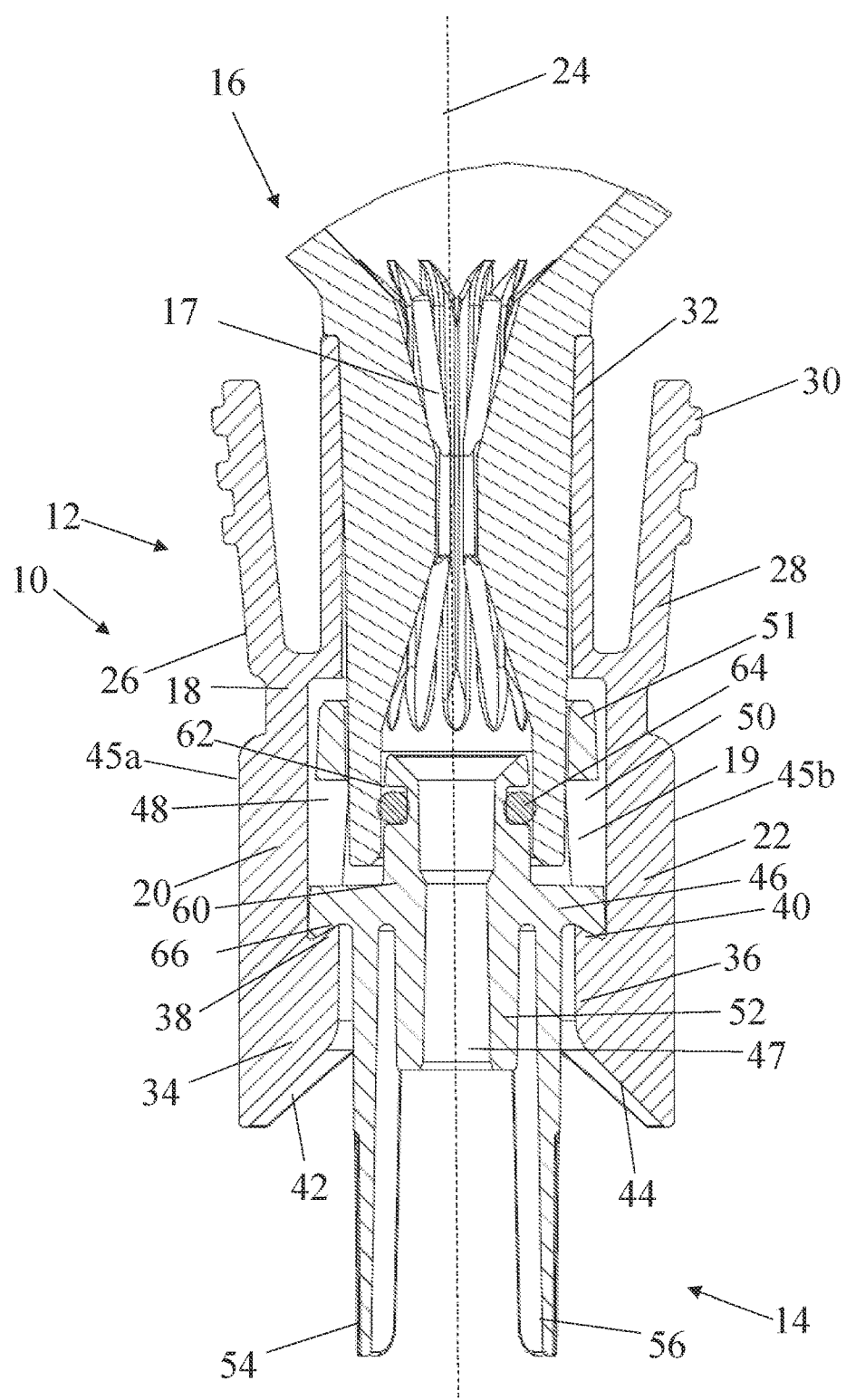
FIG. 5B is a cross-sectional view of the fluid path connector assembly of FIG. 1.
Figure 6A:
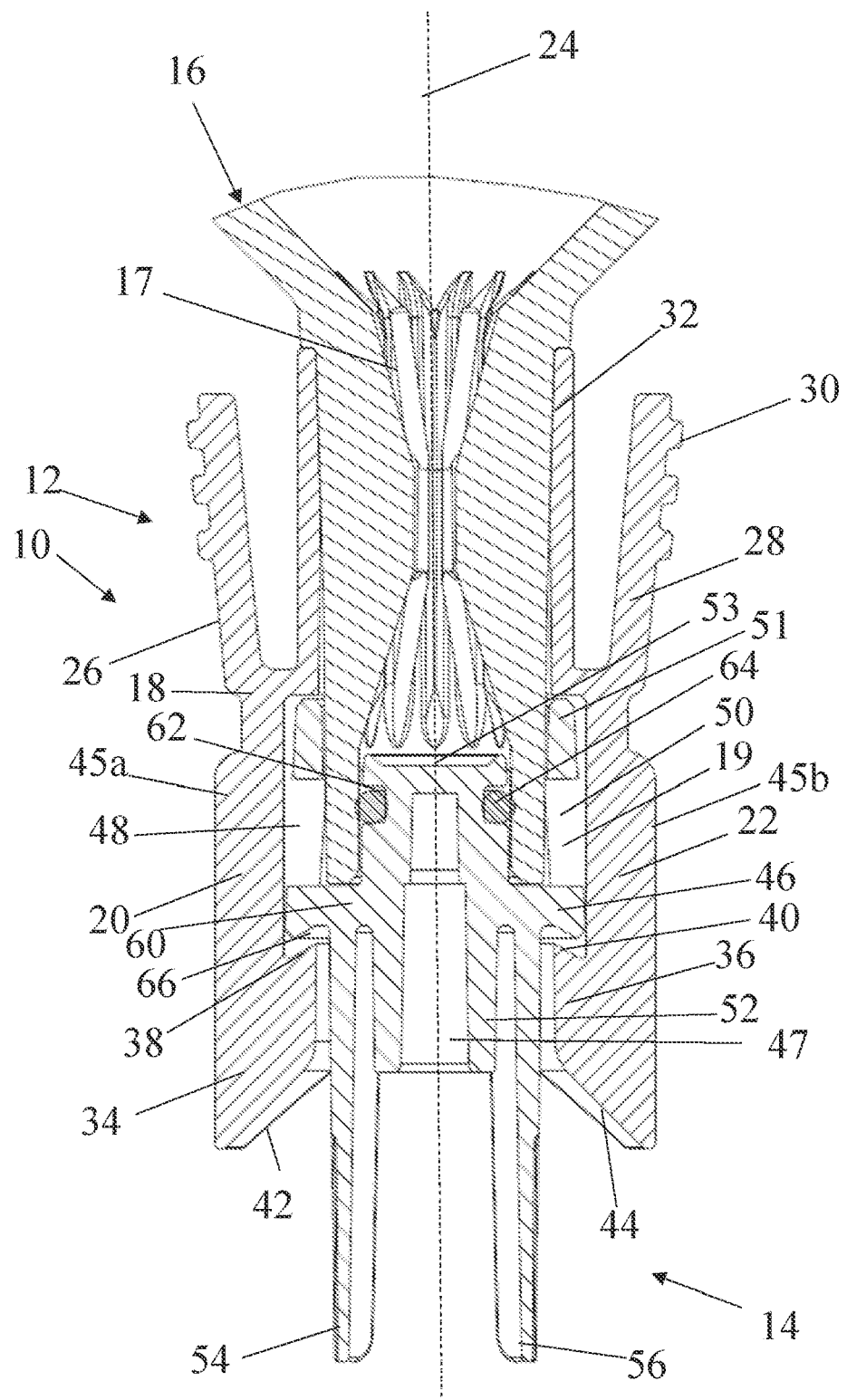
FIG. 6A is a cross-sectional view of the fluid path connector assembly of FIG. 1 showing a flow diverter included in the second connector element.
Figure 6B:
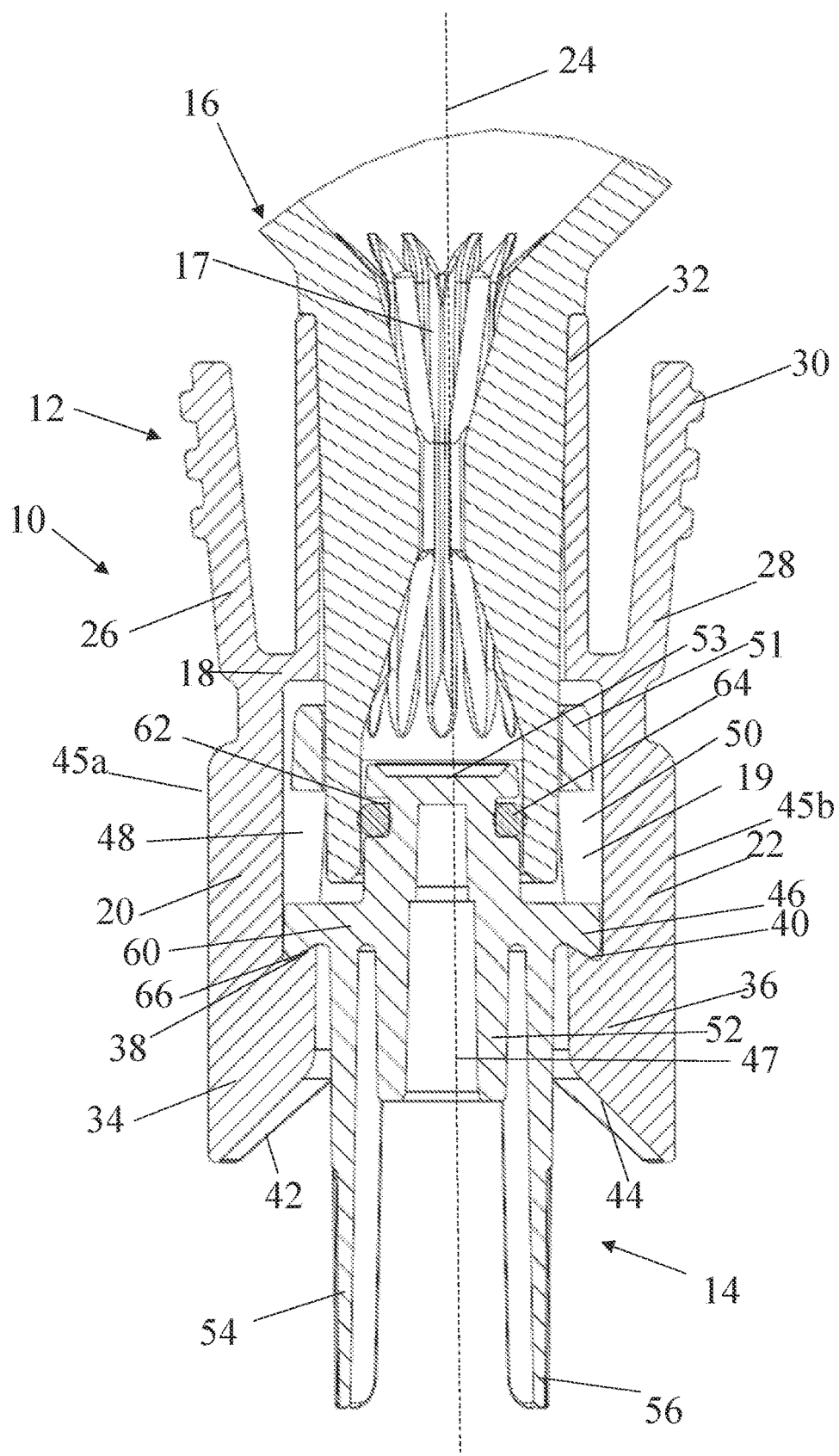
FIG. 6B is a cross-sectional view of the fluid path connector assembly of FIG. 1 showing a flow diverter included in the second connector element.
Figure 6C:
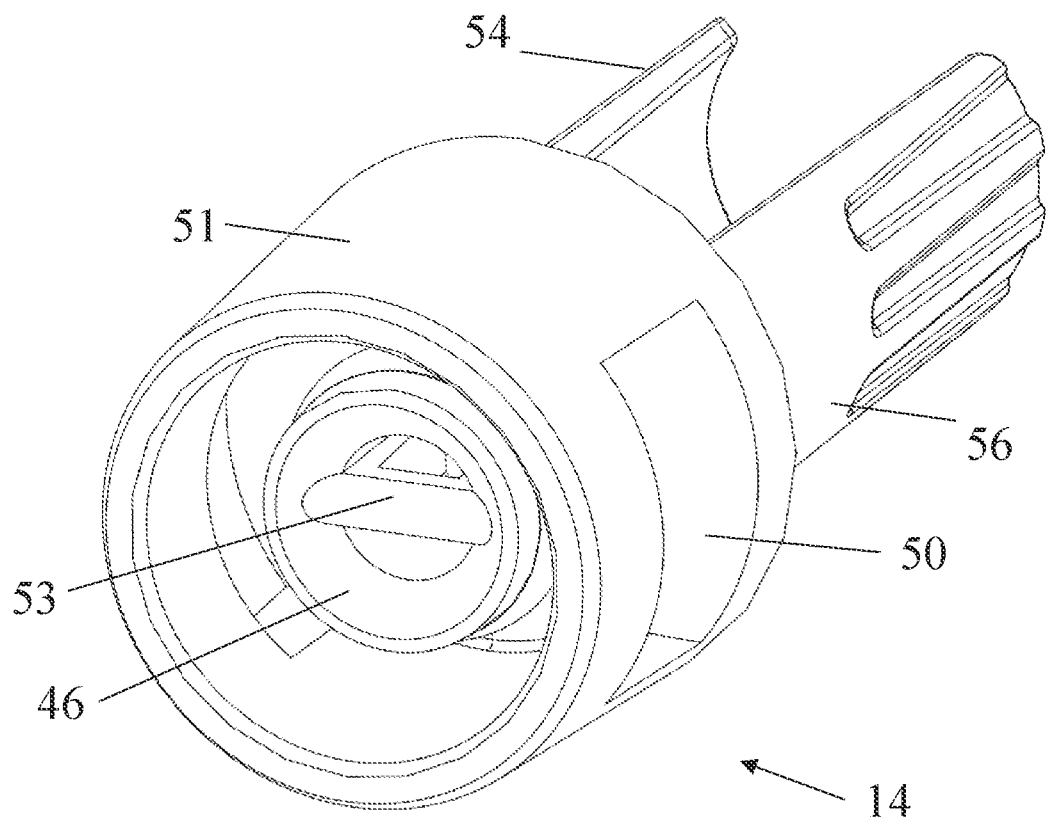
FIG. 6C is a perspective view of the second connector element with the flow diverter of FIG. 6A.
Figure 7:
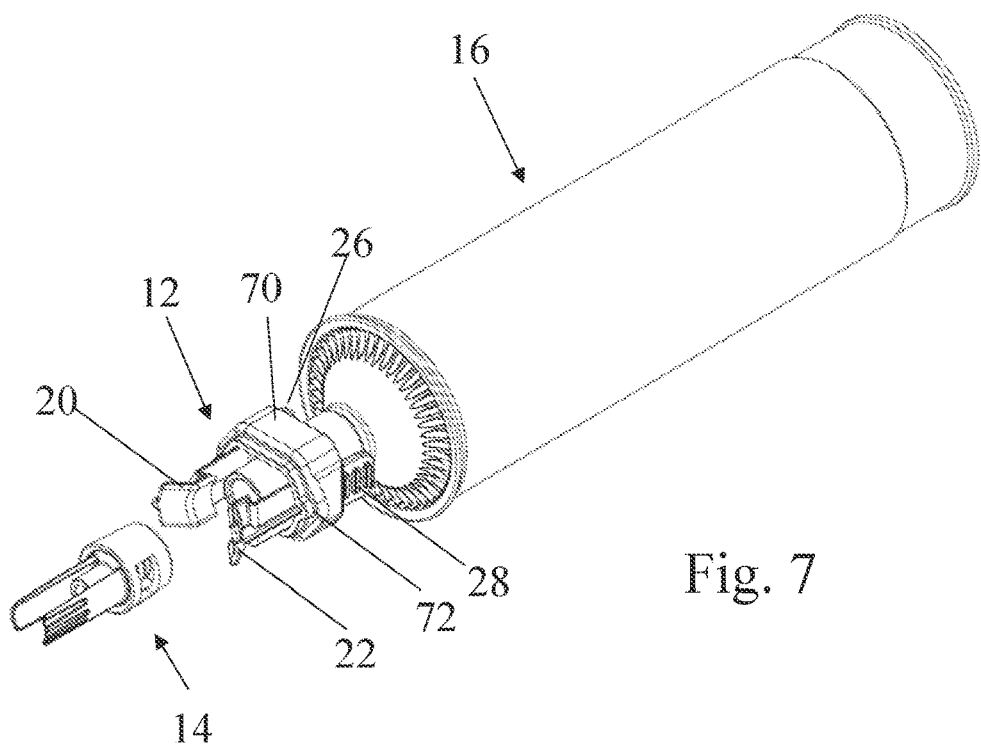
FIG. 7 is a perspective view of a fluid path connector assembly according to another example of the present disclosure shown in a disconnected position.
Figure 8:
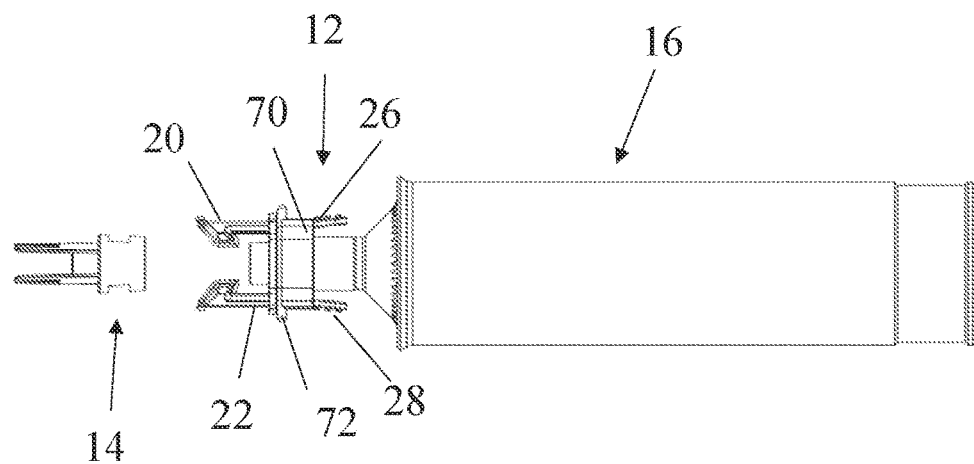
FIG. 8 is a side view of the fluid path connector assembly of FIG. 7 shown in the disconnected position.
Figure 9:
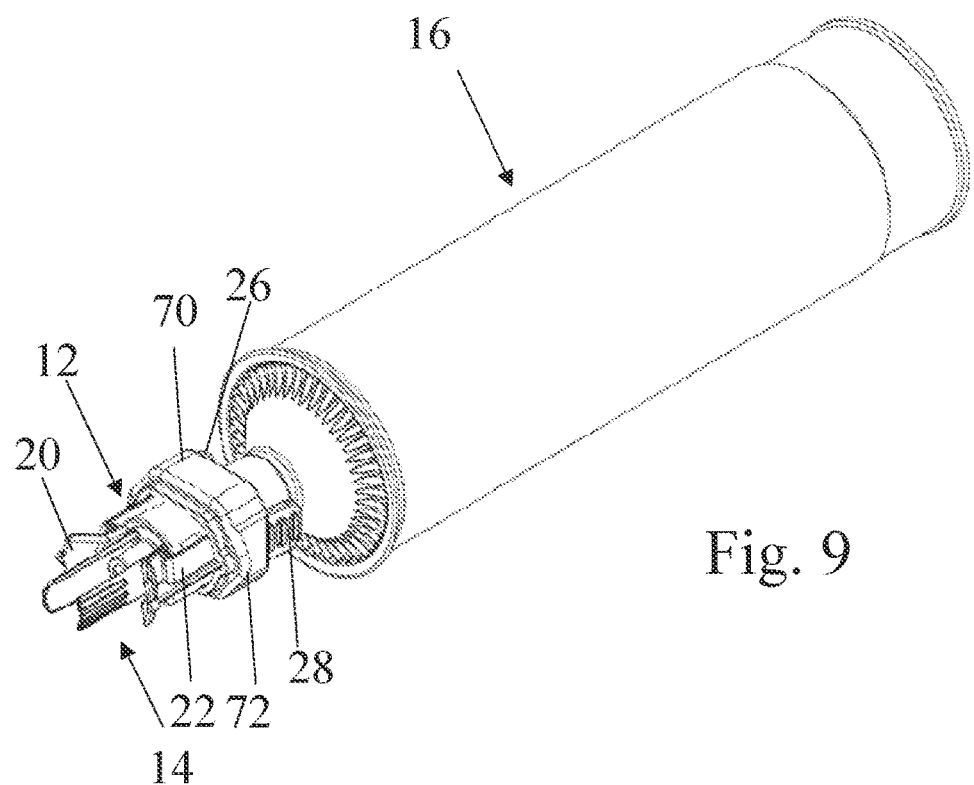
FIG. 9 is a perspective view of the fluid path connector assembly of FIG. 7 shown in the connected position.
Figure 10:
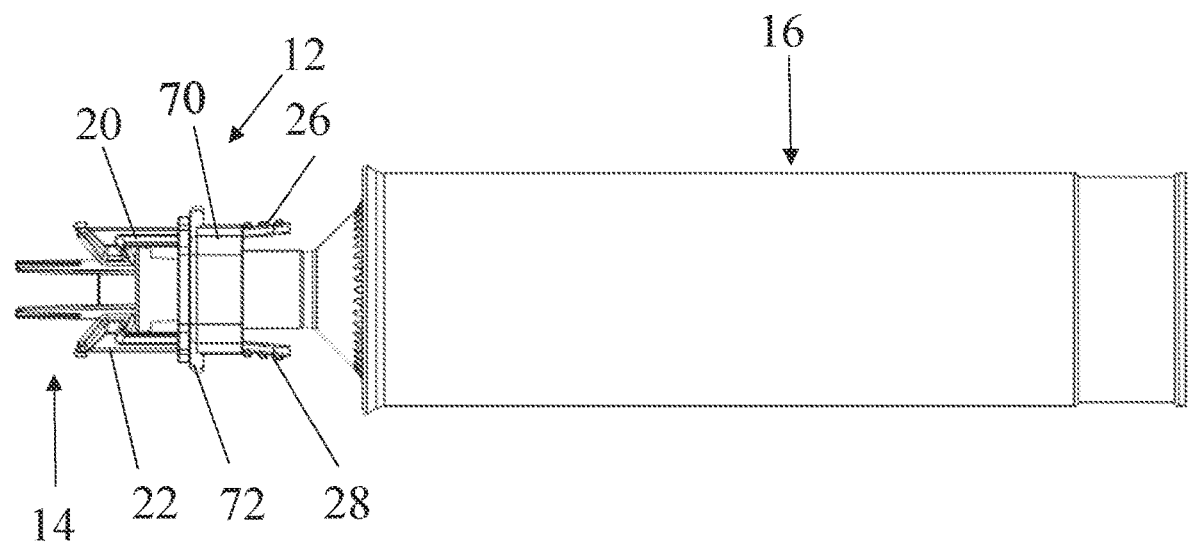
FIG. 10 is a side view of the fluid path connector assembly of FIG. 7 shown in the connected position.

With continued reference to FIGS. 5 and 6, according to some examples of the present disclosure, the second connector element 14 is described in detail. The second connector element 14 may include a body 46 having a second lumen 47 extending therethrough configured for connection to the first connector element 12 and provide fluid communication with the first lumen 19 of the first connector element 12. In one example of the present disclosure, the body 46 is configured to be substantially cylindrical in shape. Upon connection of the first and second connector elements 12, 14, the body 46 may be configured to be held between the legs 20, 22 of the first connector element 12. The body 46 may define at least one aperture 48, 50 that extends through an outer skirt 51 surrounding an outer surface of a proximal end of the body 46. The outer skirt 51 may assist in maintaining sterility of the fluid path, for example by preventing inadvertent touching and contamination of the inner fluid path by a technician during manipulation of the connector assembly. In one example of the present disclosure, the body 46 defines two apertures 48, 50 that extend therethrough. In one example of the present disclosure, the second connector element 12 may also include an attachment member 52 that extends from the body 46. The attachment member 52 may be configured to allow connection of a tubing set, a spike assembly, or a fluid container to the second connector element 12. In one example of the present disclosure, the attachment member 52 may be configured to allow a friction fit with the tubing set, spike assembly, or fluid container. The tubing set, spike assembly, or fluid container may be welded (laser welded) or otherwise adhered to the attachment member 52. It should also be made apparent that the attachment member 52 may be configured for any other type of connection including a threaded connection or a luer lock connection. In one example of the present disclosure, the second connector element 14 may also include at least one support member 54, 56 that extends from the body 46 in the same direction as and at least partially around the attachment member 52. The support members 54, 56 are configured to prevent bending of the bend of the attached fluid path element and further provide a gripping surface for an operator to grip when using the second connector element 14. In one example of the present disclosure, the second connector element 14 includes two support members 54, 56.

In various examples of the present disclosure, the second connector element 14 may also include a support base 60 that extends from the body 46 in a direction opposite to the attachment member 52. The skirt 51 may extend around the support base 60 as described herein. In one example of the present disclosure, the support base 60 may be configured for insertion into an opening of a distal tip of the syringe 16 to connect the syringe 16 attached to the first connector element 12 to the tubing set, spike assembly, or fluid container attached to the second connector element 14. It is also contemplated that the support base 60 may also be configured to receive the distal tip of the syringe 16. In one example of the present disclosure, the support base 60 may define at least one circumferential channel 62 that may be configured to receive at least one sealing element 64. In one example of the present disclosure, the at least one sealing element 64 may be at least one O-ring, an overmolded sealing surface molded onto an outer surface of the support base 60, a quad ring, or any other dynamic seal. In one example of the present disclosure, upon connection of the first and second connector elements 12, 14, the at least one sealing element 64 is configured to establish a fluid-tight seal between the support base 60 and the distal tip of the syringe 16. By using this sealing element 64, as fluid passes between the syringe 16 connected to the first connector element 12 and the tubing set or fluid container connected to the second connector element 14, no fluid is permitted to leak from the fluid path connector assembly 10. As the second connector element 14 is pulled away from the first connector element 12, the support base 60 is pulled out of the distal tip of the syringe 16. As the support base 60 is pulled out of the distal tip of the syringe 16, the sealing member 64 continues to hold the fluid-tight seal between the support base 60 and the distal tip of the syringe 16 until the support base 60 is removed completely from the distal tip of the syringe 16. In one example of the present disclosure, the fluid path connector assembly 10 may include two sealing members provided on the support base 60 of the second connector element 14. By providing a plurality of sealing members, the sterility of the fluid path connector assembly 10 is improved.

In one example of the present disclosure, the body 46 of the second connector element 14 may also define an undercut 66 on a proximal surface thereof, such as in the form of a groove or channel having an outer angled wall with an angle that is complementary to the angled surface of flanges 34, 36. The undercut 66 may be configured to receive the portions 38, 40 of the first and second flanges 34, 36 of the first connector element 12 to ensure the first and second connector elements 12, 14 remain connected during use of the fluid path connector assembly 10. In one example of the present disclosure, the undercut 66 may be formed as a channel in at least a portion of the body 46. The undercut 66 may have a sloped surface that extends towards the second lumen 47 of the second connector element 14 from an outer surface of the body 46 to an inner surface of the body 46. In one example of the present disclosure, the undercut 66 may extend around the entire circumference of the body 46. It is also contemplated that the undercut 66 may also only be provided on a portion of the circumference of the body 46. In one example of the present disclosure, the sloped surface of the undercut 66 may substantially correspond to the sloped surface of the corresponding portions 38, 40 of the first and second flanges 34, 36 of the first connector element 12. The sloped surface of the undercut 66 may extend at an angle relative to a longitudinal axis of the second connector element 14 that corresponds to the longitudinal axis 24 of the first connector element 12. In one example of the present disclosure, the sloped surface of the undercut 66 extends at an angle of 60 degrees relative to the longitudinal axis of the second connector element 14. In other examples of the present disclosure, the sloped surface of the undercut 66 may be angled ranging from 45 degrees and 75 degrees from the longitudinal axis of the second connector element 14. In another example of the present disclosure, the sloped surface of the undercut 66 may be angled ranging from 55 degrees and 65 degrees from the longitudinal axis of the second connector element 14. In one example of the present disclosure, the sloped surface of the undercut 66 slopes inwardly from an end of the body 46 proximate the attachment member 52 towards an end of the body 46 proximate the support base 60.

With continued reference to FIGS. 1-6, a method of connecting and disconnecting the fluid connector system 10 is described in detail. In one example of the present disclosure, the first connector element 12 may be operatively connected to a syringe 16. In one example, the first connector element 12 is welded to a distal end, and more particularly, to a distal tip of the syringe 16. The distal tip of the syringe 16 may be received in the support portion 32 of the first connector element 12. In one example of the present disclosure, the second connector element 14 may be operatively connected to a tubing set, spike assembly, or fluid container. The tubing set, spike assembly, fluid container, or other fluid path component may be connected to the attachment portion 52 of the second connector element 14. According to various examples, the connector assembly 10 may be configured to provide a user with a visual and/or audible signal that the connector assembly 10 is suitably engaged. For example, during connection of first connector element 12 with second connector element 14, as the first and second flanges 34, 36 of the first connector element 12 pass the body of the second connector element 14, an audible click may be heard as the first and second flanges 34, 36 engage the undercut 66 indicating that the two connector elements are engaged. Further, a user may visually check to see that the first and second flanges 34, 36 are engaged with the undercut 66, thus indicating that the connector assembly 10 is ready for use. As noted herein, while the Figures generally illustrate an embodiment where the first connector element 12 is associated with a syringe and the second connector element 14 is associated with some other fluid path component, the relative positions of the first connector element 12 and the second connector element 14 may be interchanged without deviating from the intent of the present disclosure.

In one example of the present disclosure, after the syringe 16 has been connected to the first connector element 12 and the tubing set/spike assembly/fluid container has been connected to the second connector element 14, the first and second connector elements 12, 14 may be moved towards one another for connection. As the second connector element 14 is moved towards the first connector element 12, the body 46 of the second connector element 14 may come into engagement with the sloped surfaces 42, 44 of the first and second flexible legs 20, 22 of the first connector element 12. Since a diameter of the body 46 of the second connector element 14 may be greater than an opening defined by the legs 20, 22 of the first connector element 12, the body 46 of the second connector element 14 may force the legs 20, 22 to move outwardly as the body 46 pushes against the sloped surfaces 42, 44. At a certain point the legs 20, 22 will be forced outwardly enough to permit the body 46 of the second connector element 14 to move past the legs 20, 22 to be received within the first connector element 12. It is also contemplated that the actuating arms 26, 28 may be simultaneously pressed inwardly in order to move the legs 20, 22 outwardly to receive the second connector element 14 within the first connector element 12 while exerting less engagement force on the second connector element 14 or without having to press the body 46 of the second connector element 14 against the sloped surfaces 42, 44 of the legs 20, 22. The actuating arms 26, 28 may then be released after the body 46 of the second connector element 14 has been received within the first connector element 12.

In one example of the present disclosure, after the body 46 of the second connector element 14 moves past the legs 20, 22, the legs 20, 22 may be configured to move inwardly towards one another to an original resting position. As the legs 20, 22 move inwardly, the flanges 34, 36 of the legs 20, 22 are moved into position to engage with the undercut 66 of the body 46 of the second connector element 14. An audible click or other noise may be heard at this time, indicating that the connector assembly 10 is engaged. In one example of the present disclosure, before fluid is transferred through the fluid path connector assembly 10, the first connector element 12 may be movable relative to the second connector element 14 (see FIG. 5). As the body 46 of the second connector element 14 is moved into the first connector element 12, the support base 60 of the second connector element 14 is inserted into the distal tip of the syringe 16 to create a fluid tight seal using the sealing member 64. As fluid is transferred through the fluid path connector assembly 10, due to the fluid pressure exerted by the fluid passing through the fluid path connector assembly 10, the second connector element 14 may be moved away from the syringe 16. In order to prevent disconnection of the second connector element 14 from the first connector element 12, as the second connector element 14 moves away from the syringe 16, the flanges 34, 36 of the first connector element 12 positively engage with the undercut 66 of the second connector element 14 to prevent disconnection of the first and second connector elements 12, 14 (see FIG. 6). Due to the angled surfaces of the flanges 34, 36 and the undercut 66, under pressurized conditions, as the second connector element 14 moves away from the first connector element 12, interaction between the angled surfaces 38, 40 of the flanges 34, 36 of the first connector element 12 and the sloped surface of the undercut 66 of the second connector element 14 cause first and second flexible legs 20, 22 to be drawn radially inward, increasing the engagement force of the fluid connector system 10 and preventing disconnection under relatively high fluid pressures. In one example of the present disclosure, the fluid path connector assembly 10 may withstand a pressure of greater than 800 psi and even up to 1200 psi, which may be used during an angiographic imaging procedure.

In one example of the present disclosure, after the fluid has been transferred through the fluid path connector assembly 10, for example after completion of the imaging procedure, the first and second connector elements 12, 14 are ready for disconnection from one another. In one example of the present disclosure, the actuating arms 26, 28 of the first connector element 12 may be pressed inwardly towards one another by an operator. As the actuating arms 26, 28 are moved inwardly, the legs 20, 22 of the first connector element 12 are moved outwardly away from one another. As the legs 20, 22 move away from one another, the opening defined by the legs 20, 22 is increased in diameter to allow the body 46 of the second connector element 14 to be pulled from the first connector element 12. Once the body 46 of the second connector element 14 has been removed from the first connector element 12, the actuating arms 26, 28 may be released by the operator to permit legs 20, 22 to move back towards one another.

With reference to FIGS. 7-12, in one example of the present disclosure, the first connector element 12 may also include a movable locking sleeve 70 provided on an outer surface of the body 18 of the first connector element 12. In one example of the present disclosure, the locking sleeve 70 may be generally received around the first connector element 12. The locking sleeve 70 is slidable along the outer surface of the body 18 along the longitudinal axis 24 of the first connector element 12. The locking sleeve 70 defines a through channel that has a diameter greater than a diameter of the body 18. An inner surface of the through channel may be contoured to substantially match the outer contour of the first connector element 12 so the locking sleeve 70 may move along the first connector element 12. In one example of the present disclosure, the locking sleeve 70 may include an at least partially circumferential flange 72 that assists in moving the locking sleeve 70 along the first connector element 12.

Figure 11:
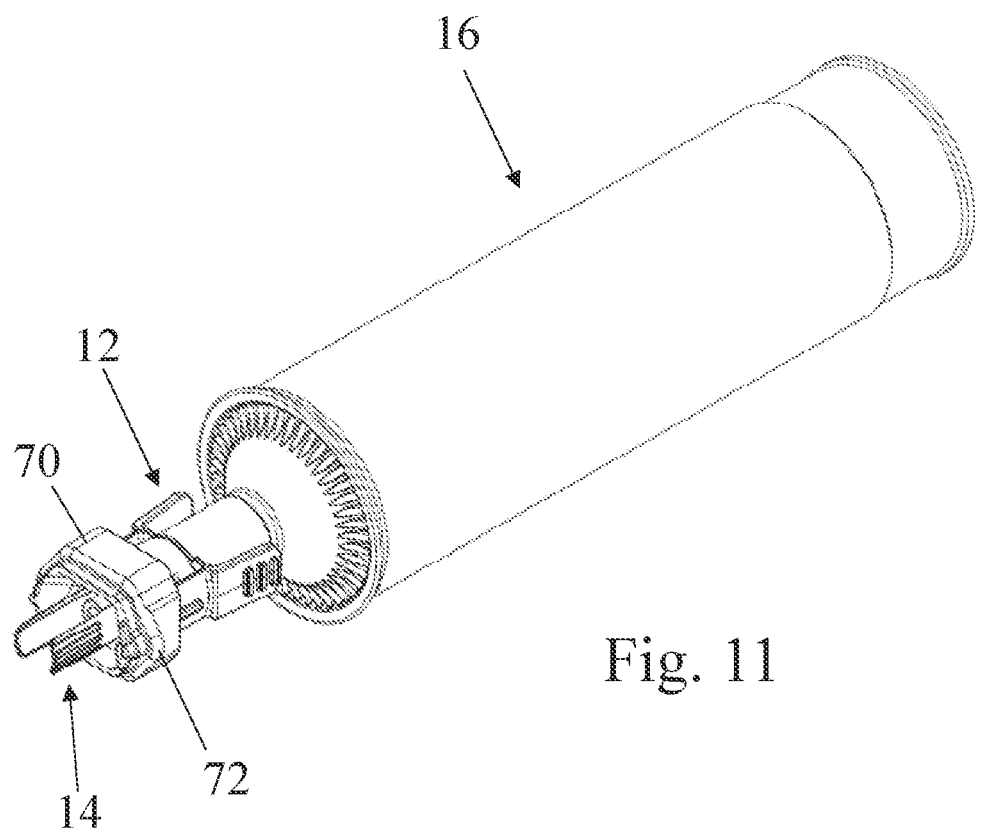
FIG. 11 is a perspective view of the fluid path connector assembly of FIG. 7 in which a locking skirt is fully locked.
Figure 12:
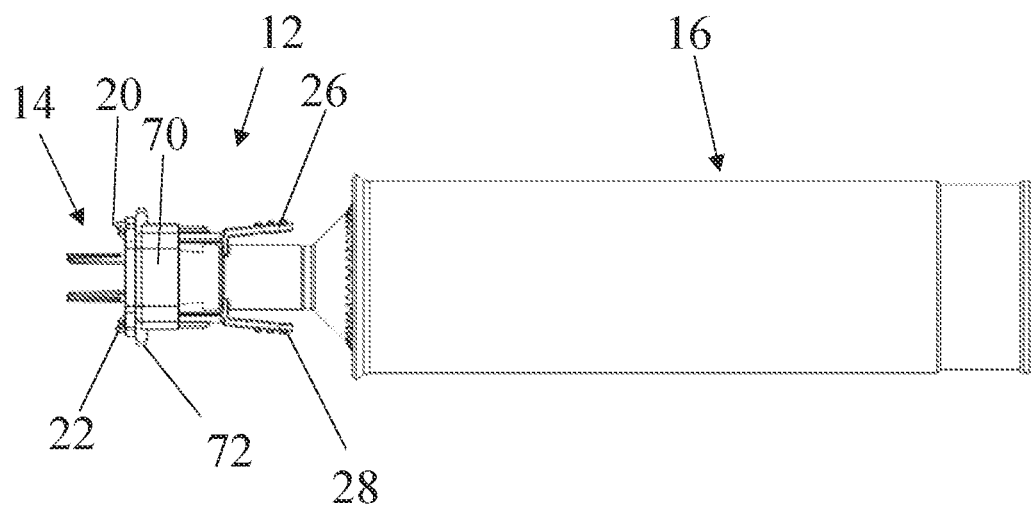
FIG. 12 is a side view of the fluid path connector assembly of FIG. 7 in which the locking skirt is fully locked.

As shown in FIGS. 7-10, in a first unlocked position, the locking sleeve 70 is distally positioned around the outer circumference of the first connector element 12. In certain examples, the locking sleeve 70 may surround actuating arms 26, 28, forcing them radially inward into the open position. After the second connector element 14 has been engaged with the first connector element 12, the locking sleeve 70 may be slid along the first connector element 12 towards the legs 20, 22. The locking sleeve 70 is slid along the legs 20, 22 until the locking sleeve 70 is positioned in a second locked position around the outer circumference of the legs, 20, 22. As shown in FIGS. 11 and 12, when positioned in the second locked position, the locking sleeve 70 assists in preventing the legs 20, 22 from moving outwardly relative to one another under high fluid pressures that are experienced when fluid is transferred through the fluid path connector assembly 10, thereby preventing disconnection of the connector 10. After the fluid has been transferred through the fluid path connector assembly 10, the locking sleeve 70 may be slid back towards the body 18 of the first connector element 12 to permit the legs 20, 22 to move outwardly relative to one another to permit the first and second connector elements 12, 14 to be disconnected from one another. In one example of the present disclosure, it is also contemplated that the locking sleeve 70 may be slid along the first connector element 12 to cover the actuating arms 26, 28, thereby forcing the actuating arms 26, 28 to move inwardly towards one another to move the legs 20, 22 outwardly away from one another. When the locking sleeve 70 is positioned on the actuating arms 26, 28, the locking sleeve 70 may be used to open the legs 20, 22 to permit the second connector element 14 to be inserted into or removed from the first connector element 12.

With reference to FIGS. 13-26, according to several examples of the present disclosure, several different types of reinforcing features for the first connector element 12 are disclosed. In these Figures, the first connector element 12 is shown having a proximal attachment for a tubing set or spike assembly, however, it is noted that these same reinforcing features may be used on first connector element 12 when associated with a syringe 16 (see FIGS. 1-6). It is to be understood that these reinforcing features may be used in conjunction with the reinforcing members 45a, 45b of the first connector element 12. The reinforcing features described below are provided to assist in preventing the legs 20, 22 from moving outwardly relative to one another under high fluid pressures experienced by the fluid path connector assembly 10. As shown in FIGS. 13 and 14, in one example of the present disclosure, at least one reinforcing member 74 may extend from a support base 76 provided on the body 18 of the first connector element 12. The support base 76 may be provided to permit the first connector element 12 to be connected to a tubing set or a syringe 16. The reinforcing feature 74 reinforces the strength of support base 76, for example, when under high pressure during an injection procedure. In certain embodiments, under the high fluid pressures, the support base 76 may bow or deform due to the fluid pressure applied to support base 76. In certain embodiments, the support base 76 may bow outward a distance that allows the sealing member 64, for example O-ring 64, to move and/or deform and lose the fluid tight seal between the first connector member 12 and the second connector member 14. The reinforcing member 74 may extend from the support base 76 towards the actuating arms 26, 28. The reinforcing member 74 may be configured to assist in preventing the actuating arms 26, 28 from moving too far inwardly towards one another. For example, the reinforcing member 74 may be configured to act as a stop member that limits the distance the actuating arms 26, 28 can be pressed inwardly towards one another. In this example of the present disclosure, the first connector element 12 may be configured to withstand a fluid pressure of greater than 652 psi. As shown in FIGS. 15 and 16, according to one example of the present disclosure, the reinforcing member 74 may extend from close to one end of the support base 76 to close to an opposing end of the support base 76 to add further support to the body 18 of the first connector element 12 to prevent deflection or flexing of the support base 76 of the body 16. According to these examples of the present disclosure, the first connector element 12 may be configured to withstand a fluid pressure of greater than 887 psi when the reinforcing member 74, according to various embodiments, is present. With reference to FIGS. 17 and 18, according to one example of the present disclosure, a reinforcing member 80 may also extend along a longitudinal axis of the support base 76, thereby providing further rigidity to the support base 76 and the body 16 of the first connector element 12. With reference to FIGS. 19 and 20, according to one example of the present disclosure, the reinforcing member 74 may also include a further reinforcing member 82 that extends perpendicular to the reinforcing member 74, for example in an "I-beam" like configuration. In this example of the present disclosure, the first connector element 12 may be configured to withstand a fluid pressure of greater than 1,156 psi.

Figure 21:
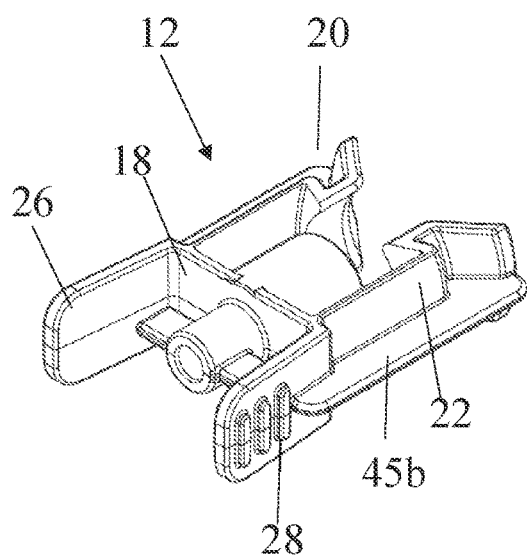
FIG. 21 is a perspective view of a connector element including reinforcing members according to another example of the present disclosure.
Figure 22:
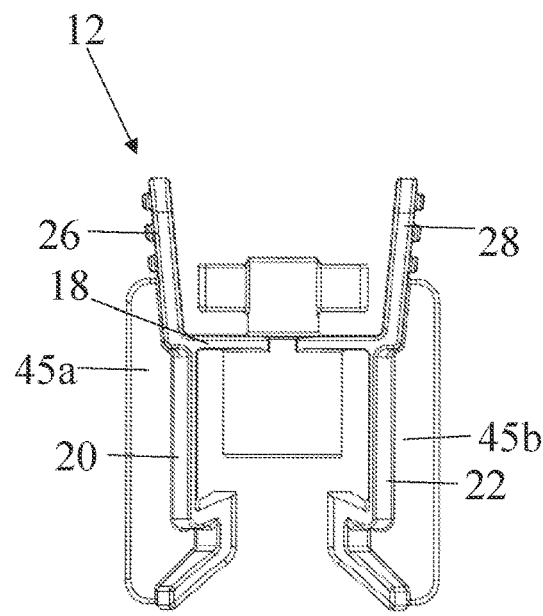
FIG. 22 is a side view of the connector element of FIG. 21.
Figure 23:
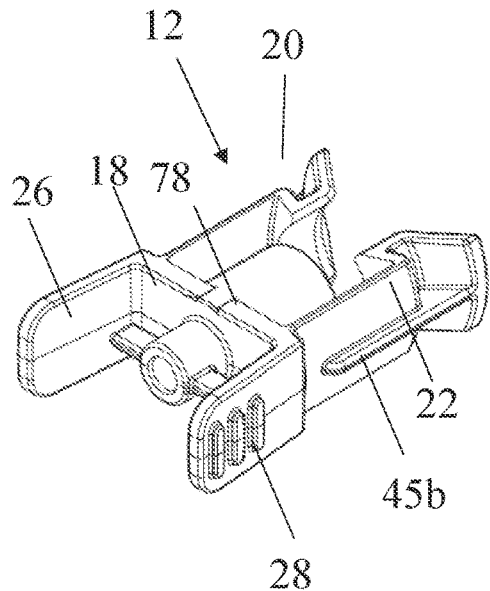
FIG. 23 is a perspective view of a connector element including reinforcing members according to another example of the present disclosure.
Figure 24:
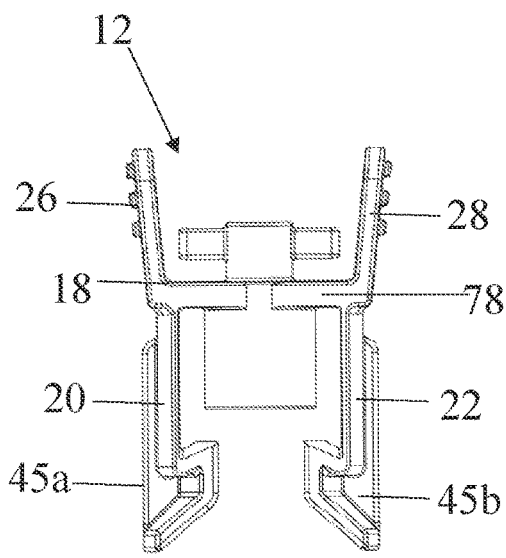
FIG. 24 is a side view of the connector element of FIG. 23.
Figure 25:
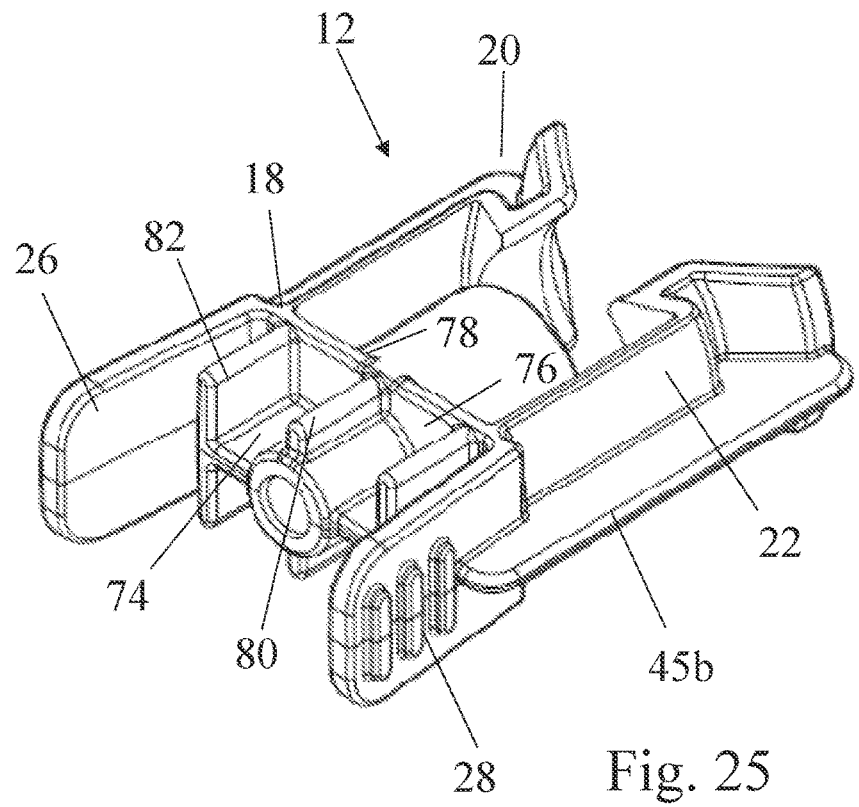
FIG. 25 is a perspective view of a connector element including reinforcing members according to another example of the present disclosure.
Figure 26:
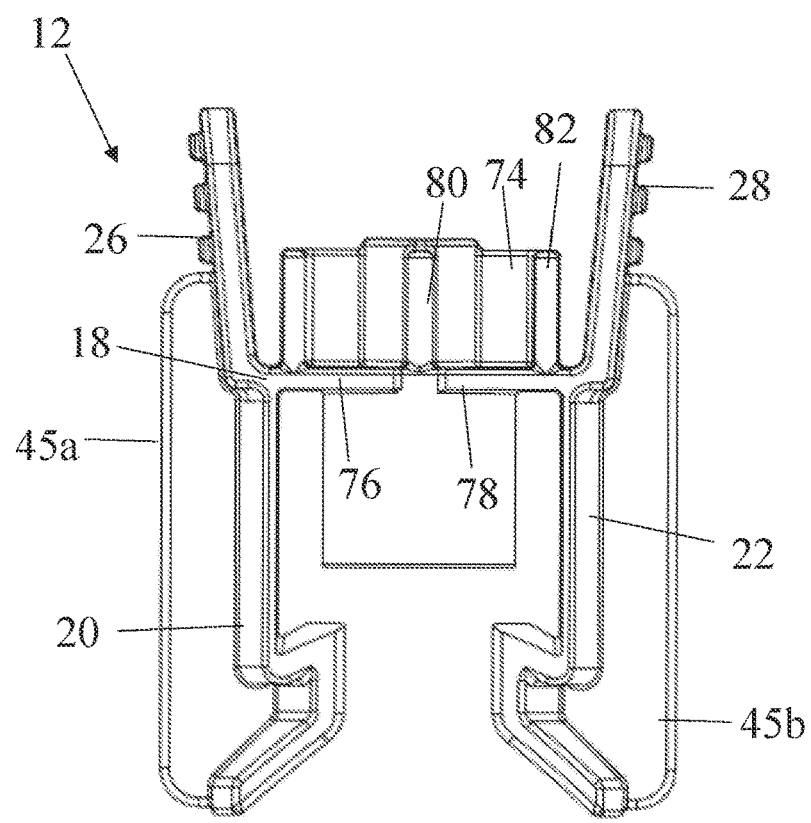
FIG. 26 is a side view of the connector element of FIG. 25.

With reference to FIGS. 21 and 22, according to one example of the present disclosure, the reinforcing members 45a, 45b may be increased in height to add further rigidity or stiffness to the legs 20, 22. By increasing the height of the reinforcing members 45a, 45b, additional material is provided on the legs 20, 22 to assist in preventing the legs 20, 22 from flexing and/or moving outward relative to one another under high fluid pressures. For example, the increase in stiffness of a beam, such as leg 20, 22, may be determined by Equation 1:

$$\text{Stiffness}=(b*h^3)/12 \qquad \text{Eq. 1}$$

where b is the width of the beam and h is the height. In this example of the present disclosure, the first connector element 12 may be configured to withstand a fluid pressure of greater than 933 psi. With reference to FIGS. 23 and 24, according to one example of the present disclosure, one or more reinforcing members 78 may also be provided on the body 18 of the first connector element 12 to assist in preventing deflection or flexing of the body 18 when the first connector element 12 is subjected to high fluid pressures. For example, as illustrated in FIGS. 23 and 24, the support base 76 may be reinforced by thickening the support base 76, for example, by increasing the thickness in the mold or by adhering a separate reinforcing member 78 to the support base 76. As shown in FIGS. 25 and 26, reinforcing member 8 may include a perpendicular feature at the center of reinforcing member 74. According to various embodiments, the first connector element 12 may include one or more of the reinforcing members 74, 78, 80, 82 described herein. FIGS. 25 and 26 illustrate an example of the present disclosure in which all of the reinforcing members 74, 78, 80, 82 may be provided on a single connector element. In this example of the present disclosure, the first connector element 12 may be configured to withstand a fluid pressure of up to or greater than 1,377 psi.

Figure 27:
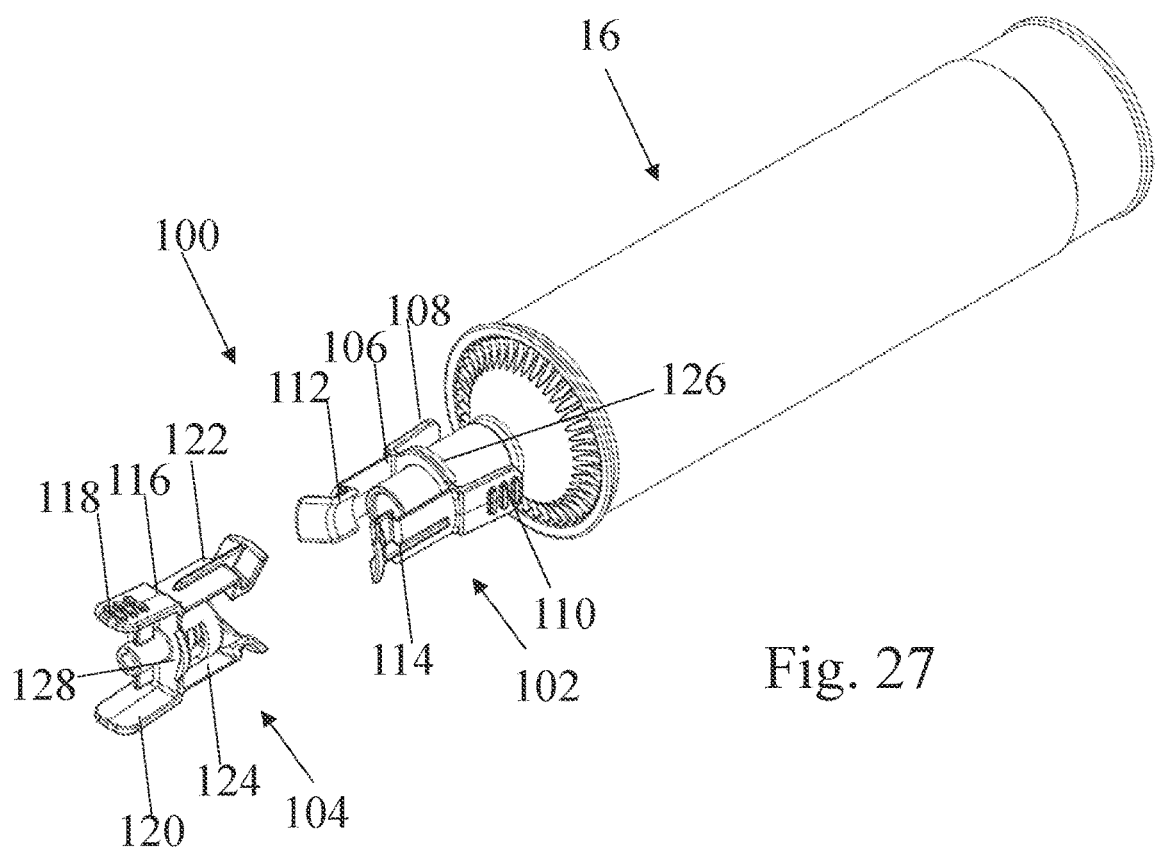
FIG. 27 is a perspective view of a fluid path connector assembly associated with a syringe shown in a disconnected position according to an example of the present disclosure.
Figure 28:
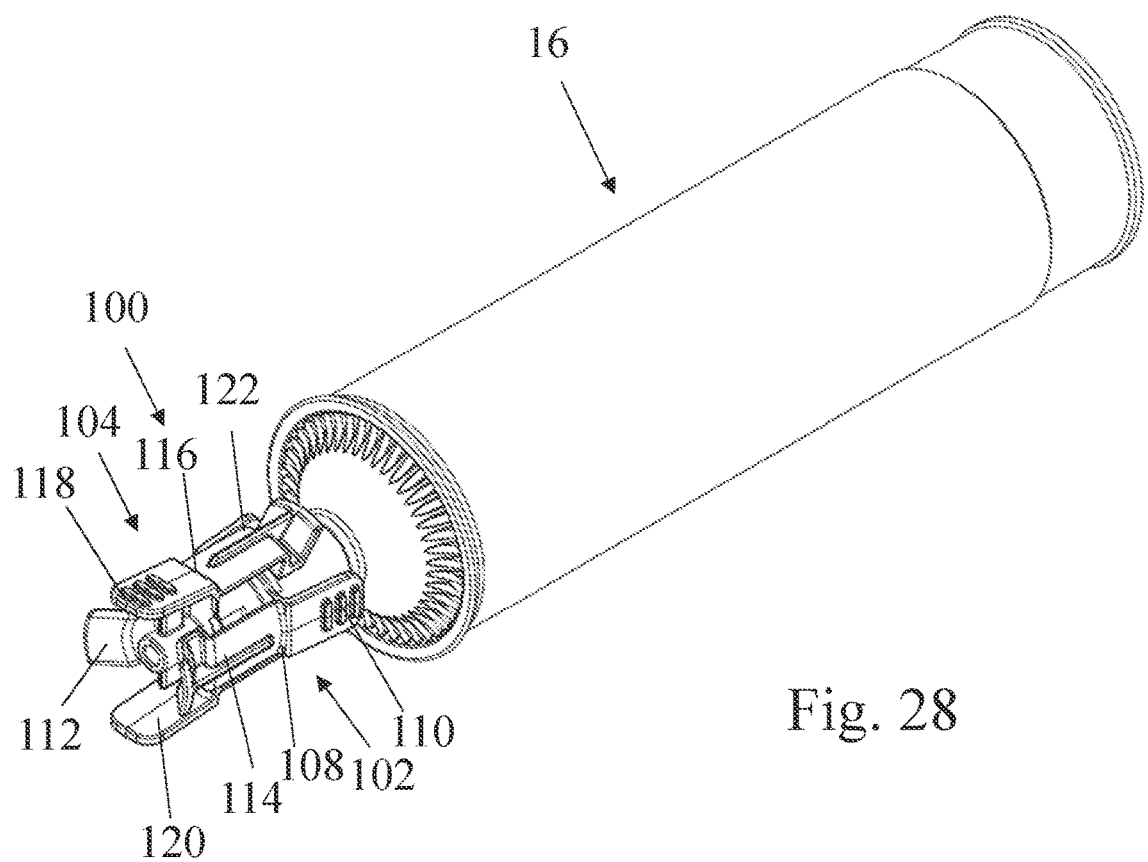
FIG. 28 is a perspective view of the fluid path connector assembly of FIG. 27 shown in a connected position.
Figure 29:
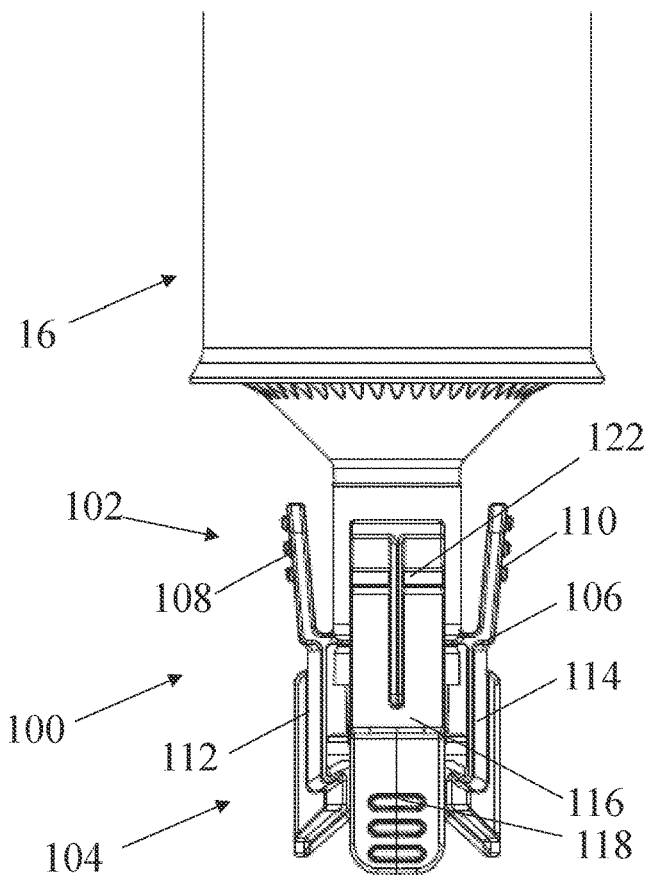
FIG. 29 is a side view of the fluid path connector assembly of FIG. 27 shown in the connected position.

With reference to FIGS. 27-29, in another example of the present disclosure, a fluid path connector assembly 100 is shown and described in detail. The fluid path connector assembly 100 may include a first connector element 102 and a second connector element 104. The first connector element 102 may be operatively connected to a syringe 16, while the second connector element 104 may be operatively connected to a tubing set, spike assembly, or fluid container. In one example of the present disclosure, the first and second connector elements 102, 104 are substantially similar to the first connector element 12 described above in connection with the fluid path connector assembly 10. The first connector element 102 may include a body 106 having a first undercut 126, a first actuating arm 108, a second actuating arm 110, a first leg 112, and a second leg 114. The second connector element 104 may include a body 116 having a second undercut 128, a first actuating arm 118, a second actuating arm 120, a first leg 122, and a second leg 124. The first connector element 102 and the second connector element 104 may be brought together in a perpendicular orientation such that the flexible legs 112, 114 of the first connector element 102 are perpendicular to the flexible legs 122, 124 of the second connector element 104 to interact with the second and first undercuts 128, 126, respectively, to connect the first and second connector members 102, 104. The first and second actuating arms 108, 110 may be pressed inwardly to open the first connector element 102, and the first and second actuating arms 118, 120 may be pressed inwardly to open the second connector element 104.

Figure 30:
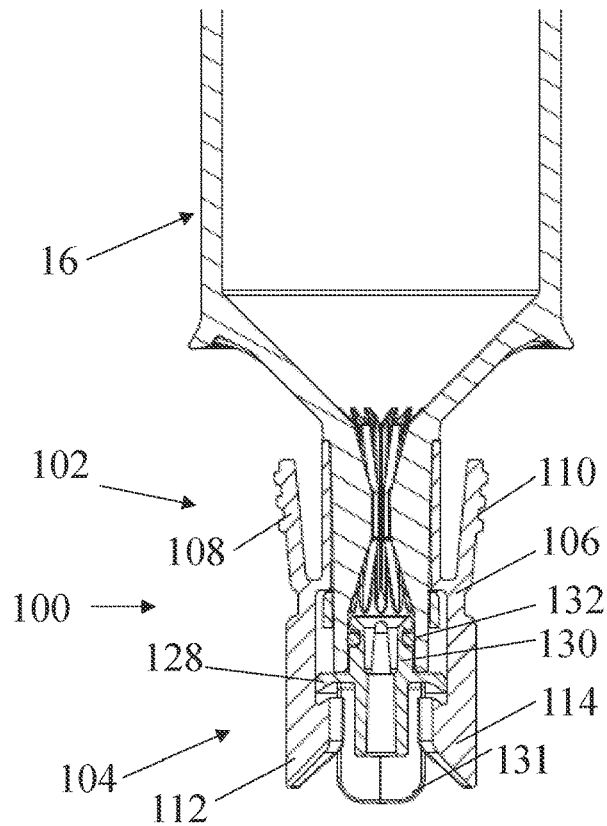
FIG. 30 is a cross-sectional view of the fluid path connector assembly of FIG. 27 shown connected to a cap.

In one example of the present disclosure, the body 106 of the first connector element 102 may define an undercut 126, and the body 116 of the second connector element 104 may define an undercut 128. The undercuts 126, 128 are provided on the first and second connector elements 102, 104 to assist in locking and operatively connecting the first and second connector elements 102, 104 with one another to create a fluid tight seal for the fluid path connector assembly 100. As shown in FIG. 30, in one example of the present disclosure, the second connector element 104 may include a support base 130 that includes at least one sealing member 132 to create a fluid tight seal with the distal tip of the syringe 16, as described in a similar fashion to the second connector element 14 discussed above. The second connector element may include a removable cap 131 for retaining sterility and preventing contamination of the syringe, for example during shipping. Upon connection, the legs 112, 114 of the first connector element 102 are configured to engage with and lock into the undercut 128 of the second connector element 104, and the legs 122, 124 of the second connector element 104 are configured to engage with and lock into the undercut 126 of the first connector element 102.

Referring back to FIGS. 27-29, during connection of the first connector element 102 with the second connector element 104, the first and second connector elements 102, 104 may be moved towards one another. As the first and second connector elements 102, 104 are moved towards one another, the legs 112, 114 of the first connector element 102 come into contact with a bottom surface of the undercut 128 of the second connector element 104 causing the legs 112, 114 to spread apart. In a similar fashion, as the first and second connector elements 102, 104 are moved towards one another, the legs 122, 124 of the second connector element 104 come into contact with a bottom surface of the undercut 126 of the first connector element 102 causing the legs 122, 124 to spread apart. As the first and second connector elements 102, 104 are pushed further towards one another, the legs 112, 114 of the first connector element 102 move past the undercut 128 of the second connector element 104 and snap into engagement with the undercut 128. Likewise, as the first and second connector elements 102, 104 are pushed further towards one another, the legs 122, 124 of the second connector element 104 move past the undercut 126 of the first connector element 102 and snap into engagement with the undercut 126. For disconnection of the fluid path connector assembly 100, the actuating arms 108, 110 of the first connector element 102 and the actuating arms 118, 120 of the second connector element 104 are pressed inwardly towards one another, respectively, to allow the legs 112, 114, 122, 124 to move outwardly so the first and second connector elements 102, 104 can be pulled apart.

Figure 31:
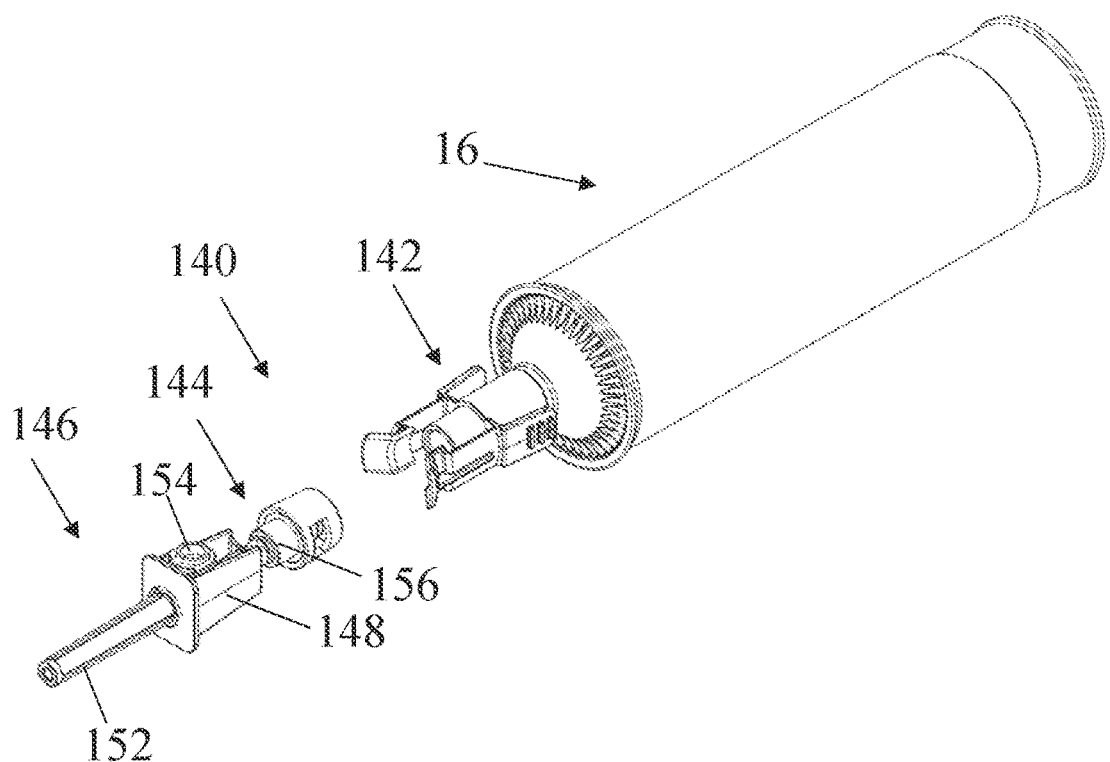
FIG. 31 is a perspective view of a fluid path connector assembly associated with a syringe and fill spike according to another example of the present disclosure shown in a disconnected position.
Figure 32:
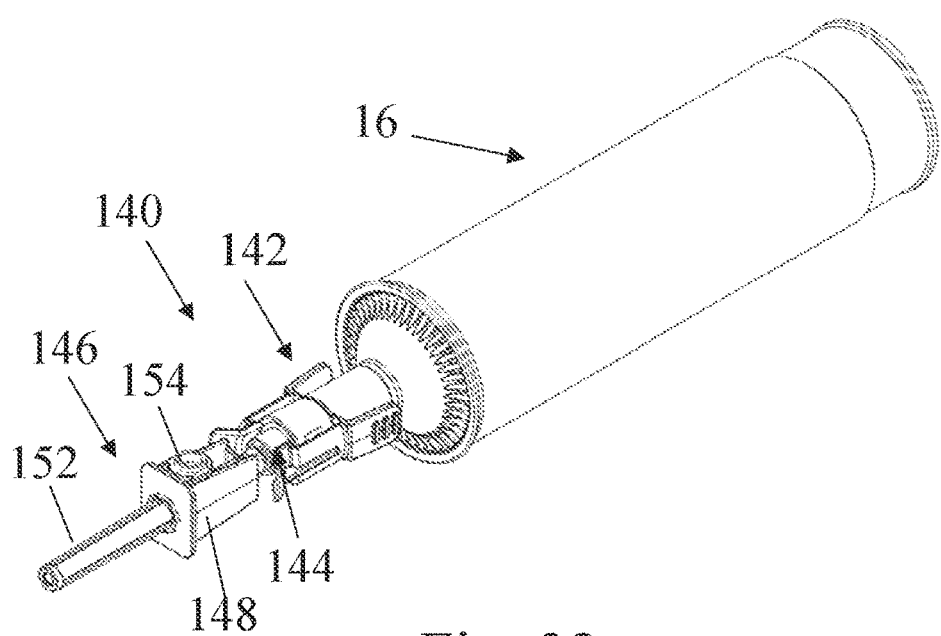
FIG. 32 is a perspective view of the fluid path connector assembly shown in FIG. 31 shown in a connected position.
Figure 33A:
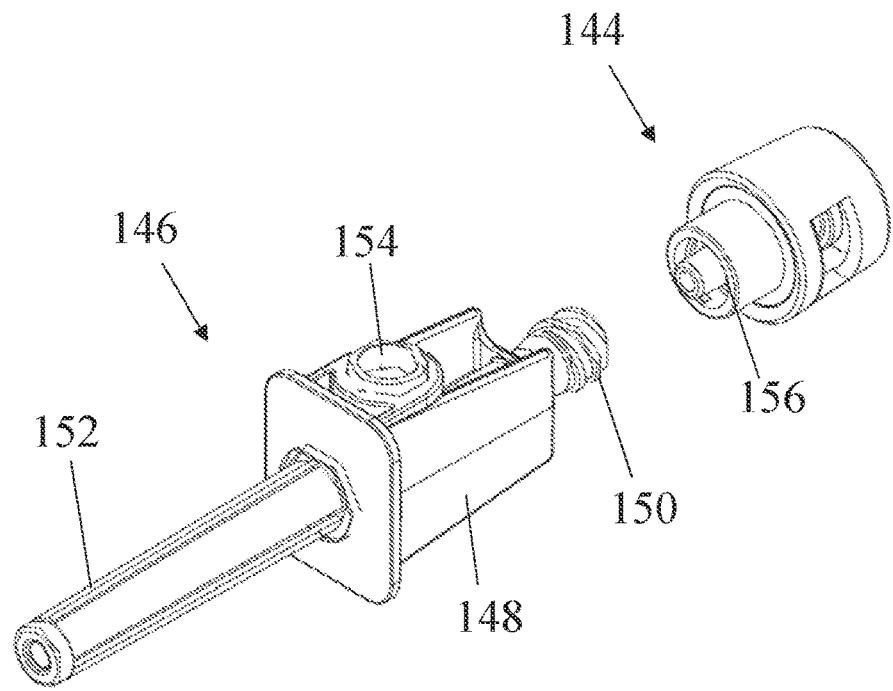
FIG. 33A is a perspective view of the fluid path connector assembly of FIG. 31.
Figure 33B:
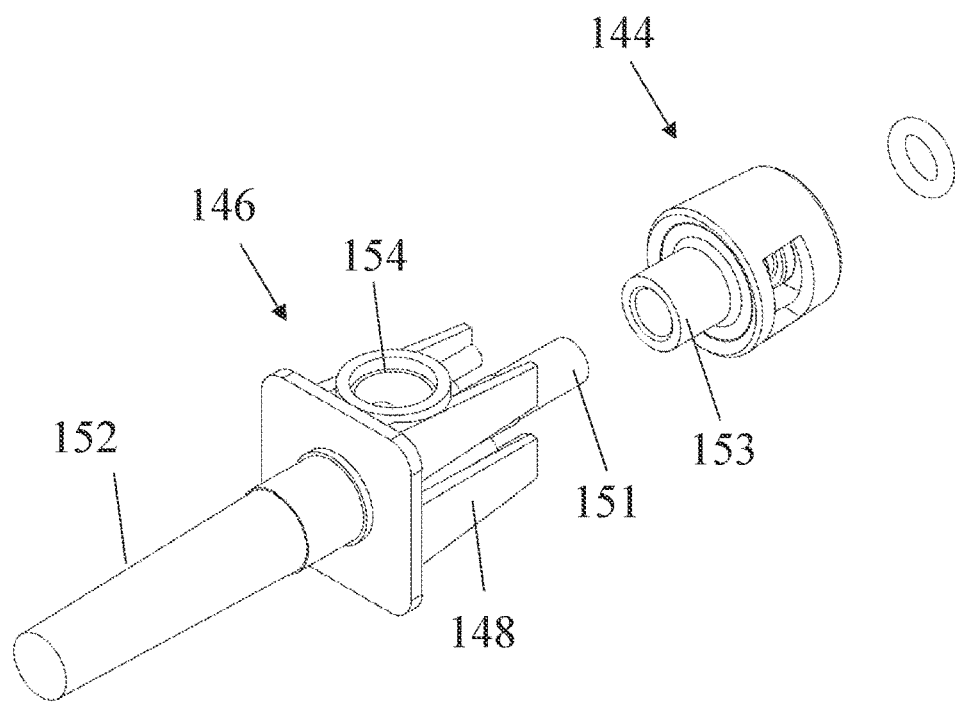
FIG. 33B is a perspective view of an example of a fluid path connector assembly according to another example of the present disclosure.
Figure 33C:
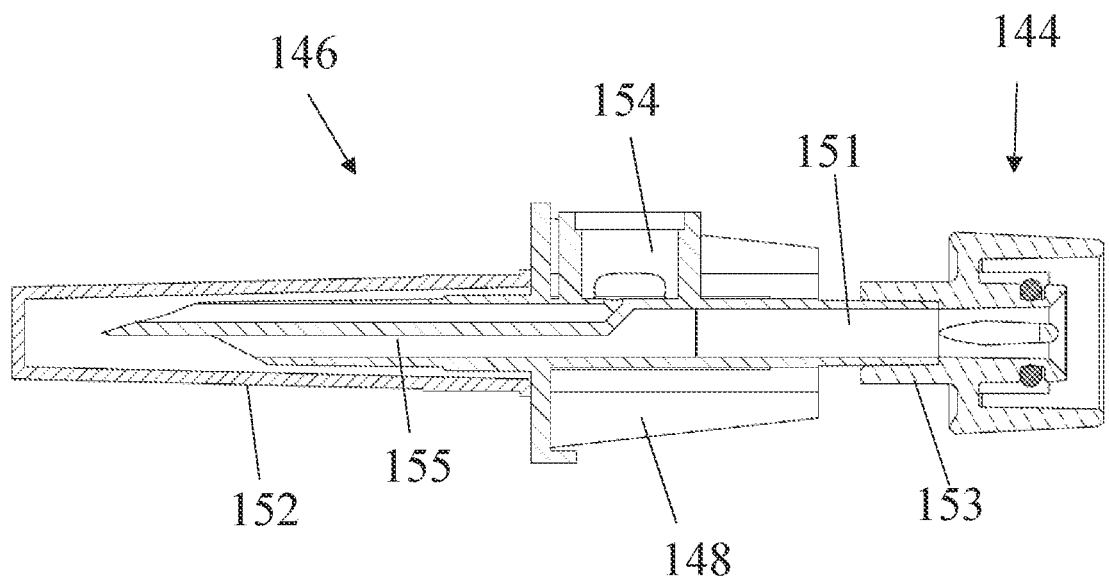
FIG. 33C is a cross-sectional view of the fluid path connector assembly of FIG. 33B.

With reference to FIGS. 31-33, according to various examples of the present disclosure, fluid path connector assemblies 140 configured to attach a spike adapter member 146 for spiking bulk fluid bottles of contrast or saline bags, to a syringe 16 are shown and described. The fluid path connector assembly 140 is substantially similar to and operates in a similar fashion to the fluid path connector assembly 10 described above with some modifications. The fluid path connector assembly 140 may include a first connector element 142 and a second connector element 144, which may be connected to a spike adapter member 146, for example by a threaded attachment or by welding (laser welding) or other adhesive means. The first connector element 142 may be substantially similar to the first connector element 12, 102 described herein. The second connector element 144 may be substantially similar to the second connector element 14 described herein but with a few modifications to connect to spike adapter member 146.

In one example of the present disclosure, the second connector element 144 may include a spike adaptor member 146 configured to permit a bulk fluid container to be connected to the second connector element 144, for example, for filling the syringe with a contrast agent or saline. The spike adaptor member 146 may include a body 148, a support base 150, a cap 152 that covers a spike member 155 (see FIG. 33C), and an air vent 154 to allow pressure equalization is defined in the body 148. In one example of the present disclosure, the connection member 150 may be a threaded member that is threadedly connected to a connection member 156 on the second connector element 144. In one example of the present disclosure illustrated in FIG. 33A, the connection members 150, 156 may be a threaded or friction fit luer lock connection system. In another example of the present disclosure illustrated in FIGS. 33B and 33C, the connection member 150 may be a male connector member 151 that may be laser welded or otherwise adhesively connected to a female connection member 153 on the second connector element 144. In another example of the present disclosure, the spike adaptor member 146 may be welded to the second connector element 144. The spike adaptor member 146 may be operatively connected to the second connector element 144 so that, instead of the second connector element 144 being connected to a tubing set similar to the second connector element 14 described herein, the second connector element 144 may be fluidly connected to a fluid bag or bulk fluid or container using the spike member 155. The spike member 155 may be used to tap the fluid bag or container to permit fluid transfer to/from a syringe 16 to/from the fluid bag or container. In one example of the present disclosure, the air vent 154 may be provided to permit air pressure to be equalized as the fluid is transferred from the container or bag through the spike adaptor member 146. In various embodiments, the second connector element 144 may include a flow diverter XX as described herein, to allow the fluid to flow into the syringe under the Coanda effect to accelerate syringe filling and reduce air bubbles as described.

Figure 34:
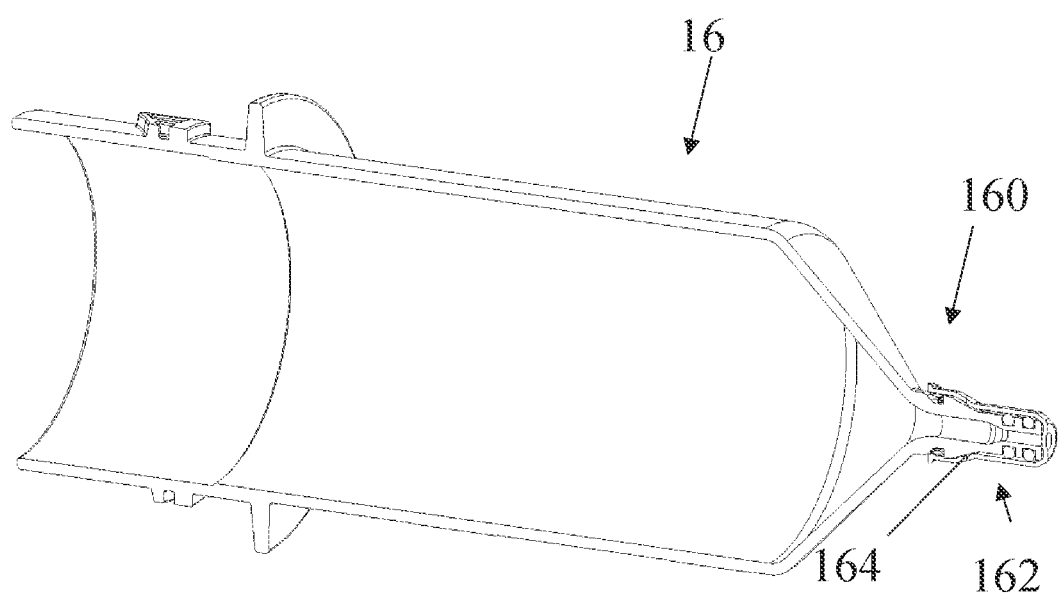
FIG. 34 is a cross-sectional view of a fluid path connector assembly and cap according to another example of the present disclosure.
Figure 35:
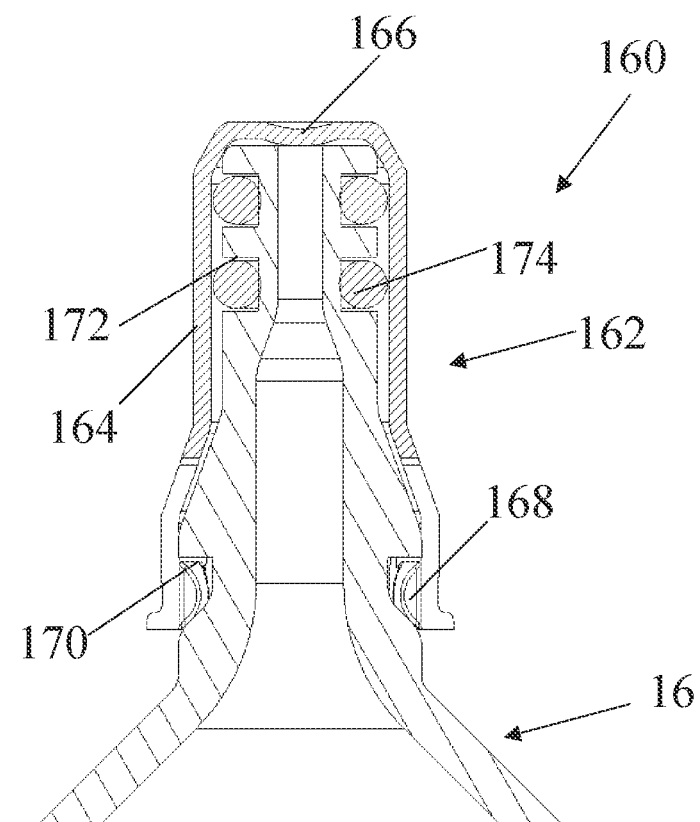
FIG. 35 is a cross-sectional view of the fluid path connector assembly of FIG. 34.

With reference to FIGS. 34 and 35, in another example of the present disclosure, a fluid path connector assembly 160 and syringe is shown and described in detail. The fluid path connector assembly 160 may include a cover element 162 configured to provide protection against contamination at a distal tip of a syringe 16. In one example of the present disclosure, the cover element 162 is configured to prevent dust and associated microorganisms from contacting and contaminating the distal tip of the syringe 16, for example during packaging, shipping, and set-up. The cover element 162 may include a body 164 that defines a channel to receive the distal tip of the syringe 16. A distal end of the cover element 162 may include a depression 166 that is configured to extend into an opening of the distal tip of the syringe 16 when the cover element 162 is positioned on the syringe 16. In one example of the present disclosure, the depression 166 may be configured to prevent dust or contaminating fluids or objects from entering the distal tip of the syringe 16. In one example of the present disclosure, the cover element 162 may include a circumferential locking protrusion 168 provided on an inner surface of the proximal end of the cover element 162. The locking protrusion 168, for example as part of a flexible locking arm 186 on the cap, which may be configured to removably lock with an undercut 170 defined in the distal tip of the syringe 16. In one example of the present disclosure, the proximal end of the cover element 162 may be separated into multiple locking arms that each include a locking protrusion 168 on an end thereof. In one example of the present disclosure, a circumferential channel 172 may be defined in the distal tip of the syringe 16. The circumferential channel 172 may be configured to receive at least one sealing member 174 that may be configured to create a fluid-tight seal with an inner surface of the cover element 162 when the cover element 162 is positioned on the distal tip of the syringe 16. In one example of the present disclosure, the sealing member 174 may be an elastomeric O-ring, an overmolded sealing surface, a quad ring, or any other dynamic seal.

Figure 36:
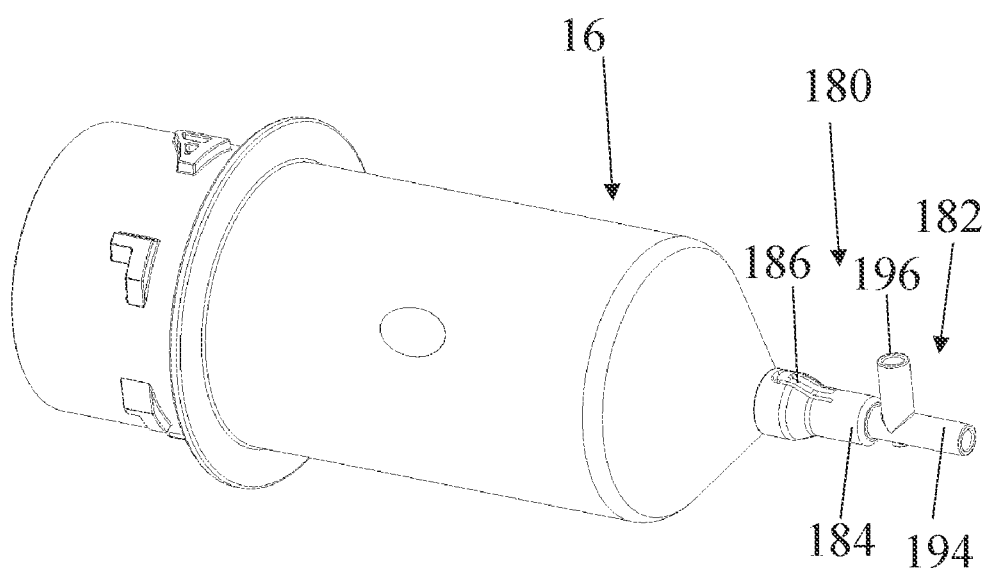
FIG. 36 is a perspective view of a fluid path connector assembly associated with a syringe and tubing set according to another example of the present disclosure.
Figure 37:
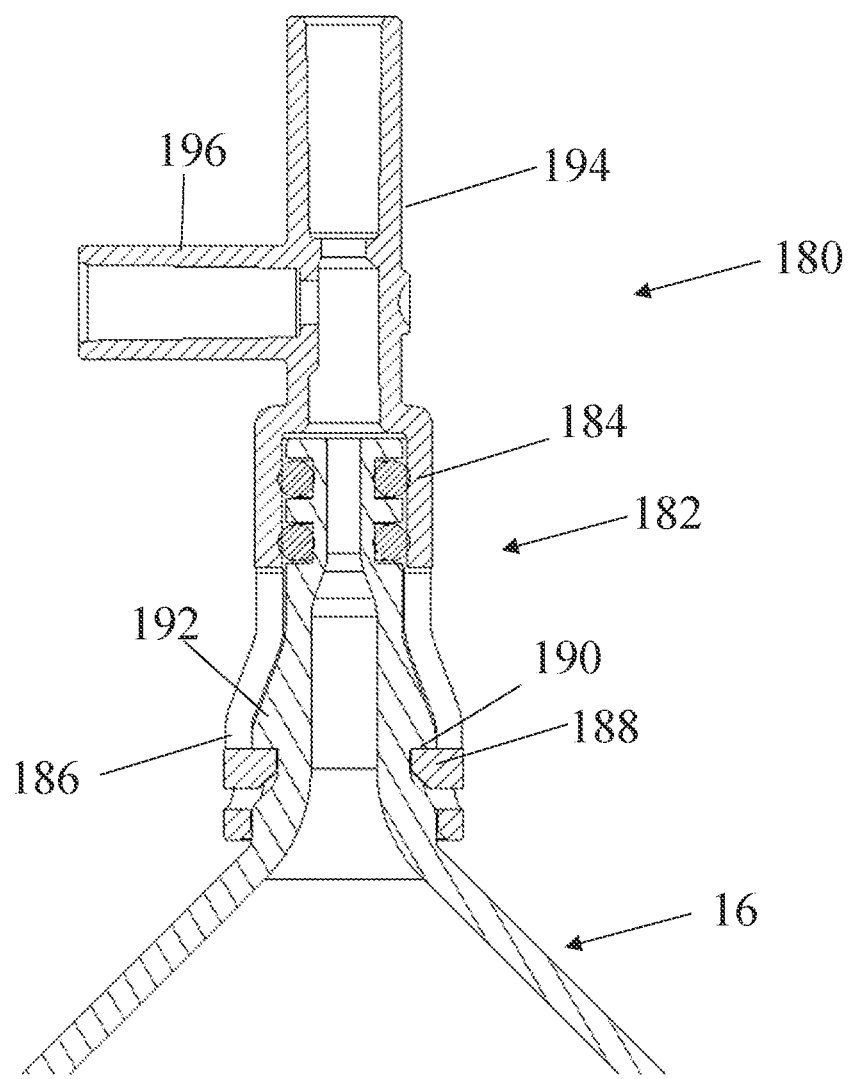
FIG. 37 is a cross-sectional view of the fluid path connector assembly of FIG. 36.

With reference to FIGS. 36 and 37, in one example of the present disclosure, a fluid path connector assembly 180 is shown and described in detail. In one example of the present disclosure, the fluid path connector assembly 180 may include a cover element 182 configured to provide for fluid communication between a tubing set and a distal tip of a syringe 16. The cover element 182 may include a body 184 that defines a channel to receive the distal tip of the syringe 16 and one or more fluid paths for filling and delivering a medical fluid. In one example of the present disclosure, the body 184 may include at least one locking arm 186 that is configured to positively engage with the distal tip of the syringe 16 to lock the cover element 182 to the syringe 16. In one example of the present disclosure, the body 184 may include two locking arms 186. The locking arms 186 may be flexible so the locking arms 186 may move outwardly relative to one another when the cover element 182 is slid on the distal tip of the syringe 16. The locking arms 186 may include a locking protrusion 188 provided on an inner surface thereof to positively engage with an undercut 190 defined in the distal tip of the syringe 16. In one example of the present disclosure, as the cover element 182 is slid in a proximal direction along the distal tip of the syringe 16, the locking arms 186 are forced to move radially outwardly by a flange 192 defined on the distal tip of the syringe 16. After the locking arms 186 have passed the flange 192 of the syringe 16, the locking arms 186 are biased to moved back towards one another to positively lock the locking protrusion 188 with the undercut 190 of the syringe 16. According to various embodiments, the cover element 182 may be non-removably locked to the syringe after engagement of the locking protrusion 188 with the undercut 190. According to this embodiment, the cover element 182 may be readily attached to syringe by a technician without the need for the threaded fit of conventional luer assemblies or with a stronger connective engagement compared to a friction fit assembly. In certain embodiments, the cover element 182 may make an audible "click" when locked to the syringe tip and/or the locking arms 186 lie flush with an outer surface of the cover element 182 when locked to the syringe tip. Thus, a user will have at least one of an audible or visual cue that the cover element 182 is securely engaged with syringe 16.

With continued reference to FIGS. 36 and 37, in one example of the present disclosure, the cover element 182 may also include a fluid transfer member 194 configured to direct fluid to/from a tubing set or fluid container to/from the syringe 16. The fluid transfer member 194 may include at least one fluid access port 196 that may be fluidly connected to a tubing set, spike assembly, or fluid container. In one example of the present disclosure, the fluid transfer member 194 may include two fluid ports, one for filling syringe 16 with a fluid and the other for delivering the fluid from the syringe 16.

Figure 38:
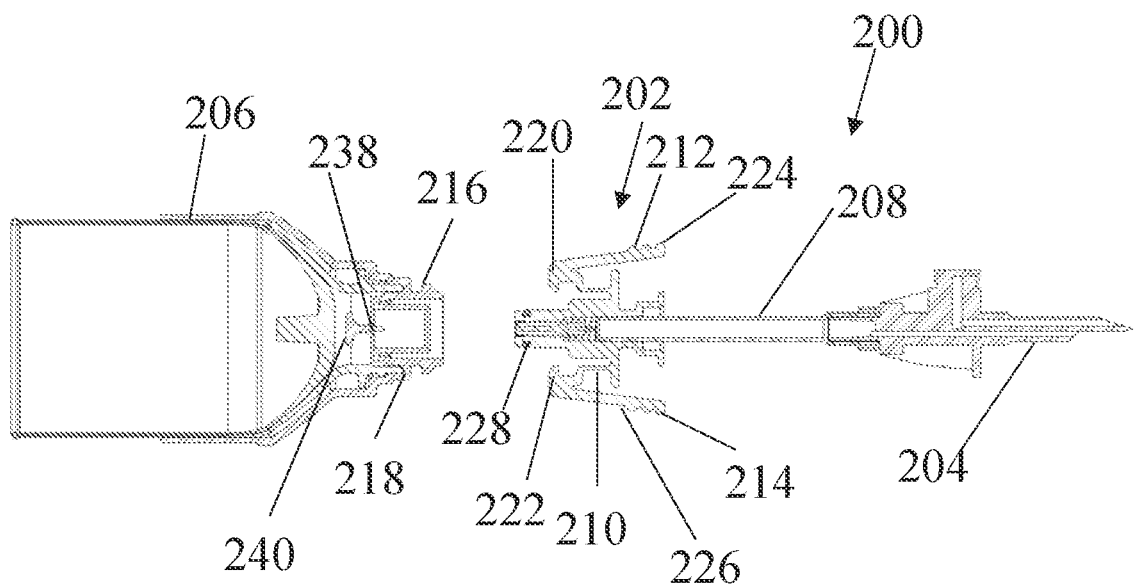
FIG. 38 is a cross-sectional view of a fluid path connector assembly associated with a syringe and spike assembly according to another example of the present disclosure shown in a disconnected position.
Figure 39:
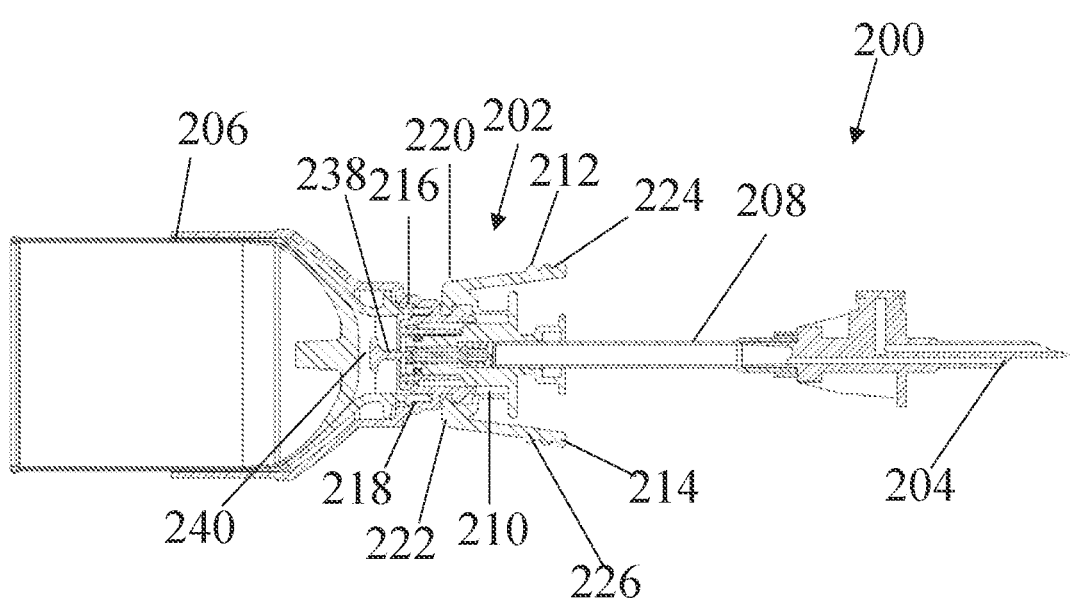
FIG. 39 is a cross-sectional view of the fluid path connector assembly of FIG. 38 shown in a connected position.
Figure 40:
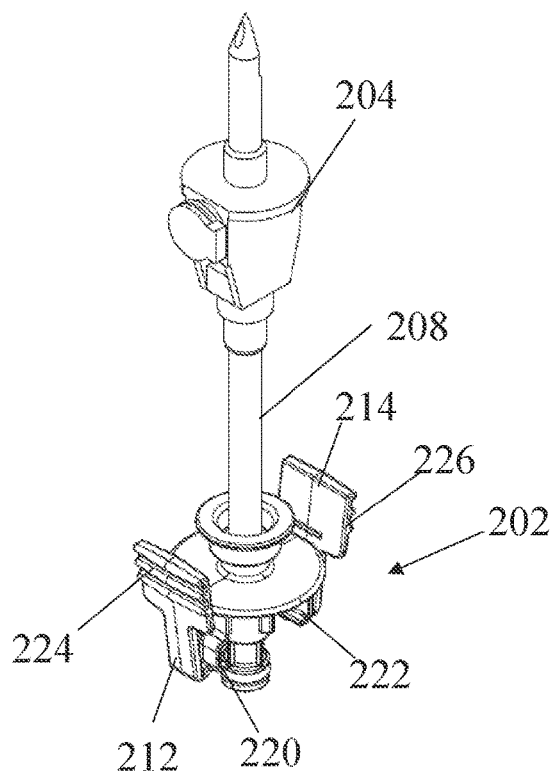
FIG. 40 is a perspective view of the fluid path connector spike assembly of FIG. 38.

With reference to FIGS. 38-42, according to another example of the present disclosure, a fluid path connector assembly 200 is shown and described in detail. While this embodiment is illustrated with a rolling diaphragm-type syringe (see e.g., International PCT Publication No. WO2016/172467, the disclosure of which is incorporated in its entirety herein), use of the fluid connector assembly 200 with other types of syringe are within the scope of the present disclosure. The fluid path connector assembly 200 may include a connector element 202 and a spike member 204 fluidly connected to the connector element 202, either directly (FIG. 43-46) or with an intervening tubing set (FIG. 38-42). The connector element 202 may be operatively connected to a fluid container 206 through spike 204, 252. In one example of the present disclosure, the connector element 202 may be fluidly connected to the spike member 204 using a transfer set 208. FIG. 38 shows the connector element 202 disconnected from the fluid container 206. In order to connect the connector element 202 to the fluid container 206, a sloped surface 210 on the connector element 202 interacts with a sloped surface 212 on the fluid container 206 as the two elements are pushed towards one another and come into contact with each other. Due to this interaction between the connector element 202 and the fluid container 206, a plurality of supports 210 on the connector element 202 are permitted to flex so that a pair of flexible legs 212, 214 are opened wide enough for the flexible legs 212, 214 to engage with a retention lip 216 on a collar 218 of the fluid container 206. It is to be understood that the fluid container 206 may be any number of containers as known in the art, for example, bottles, syringes, or a rolling diaphragm-type syringe as disclosed in WO2016/172467, WO2015/164783, WO2016/069711, and 62/730,228, the disclosures of which are incorporated by reference in their entirety.

The connector element 202 is connected to the transfer set 208 to channel fluid between the spike member 204 through the transfer set 208 and into the fluid container 206. The connector element 202 includes at least two flexible legs 212, 214 that, when pressure is applied near a top portion of each, will cause latches 220, 222 on the flexible legs 212, 214 to move laterally and outwardly relative to one another to allow for the connector element 202 to be removed from the fluid container 206, syringe, cap, or adaptor to which the connector element 202 is connected. The connector element 202 may also include ribs 224, 226 and a sealing member 228 for sealing. In one example of the present disclosure, the sealing member 228 may be an O-ring, an overmolded sealing surface, a quad ring, or any other dynamic seal.

Figure 41:
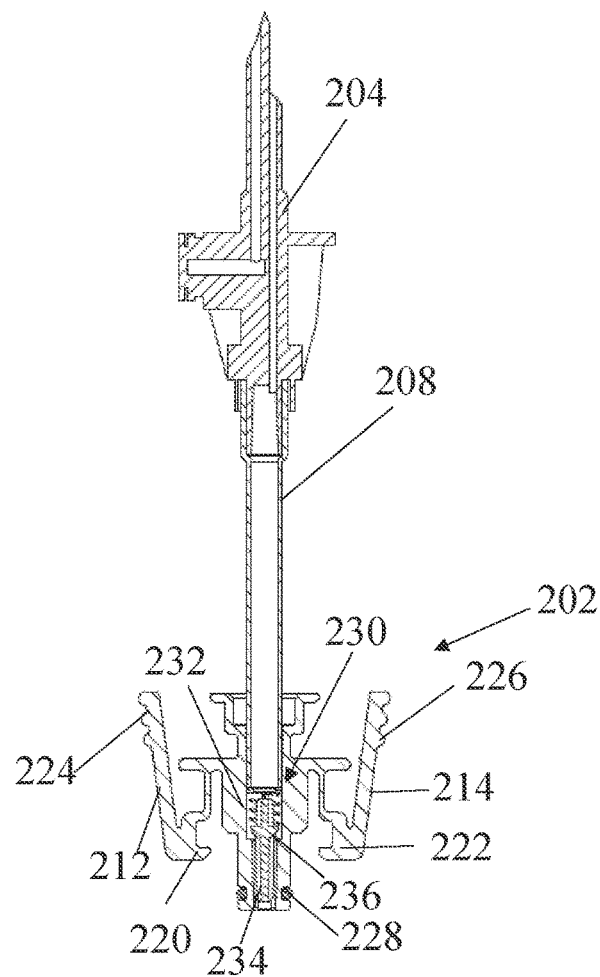
FIG. 41 is a cross-sectional view of the fluid path connector spike assembly of FIG. 38 in an open position.
Figure 42:
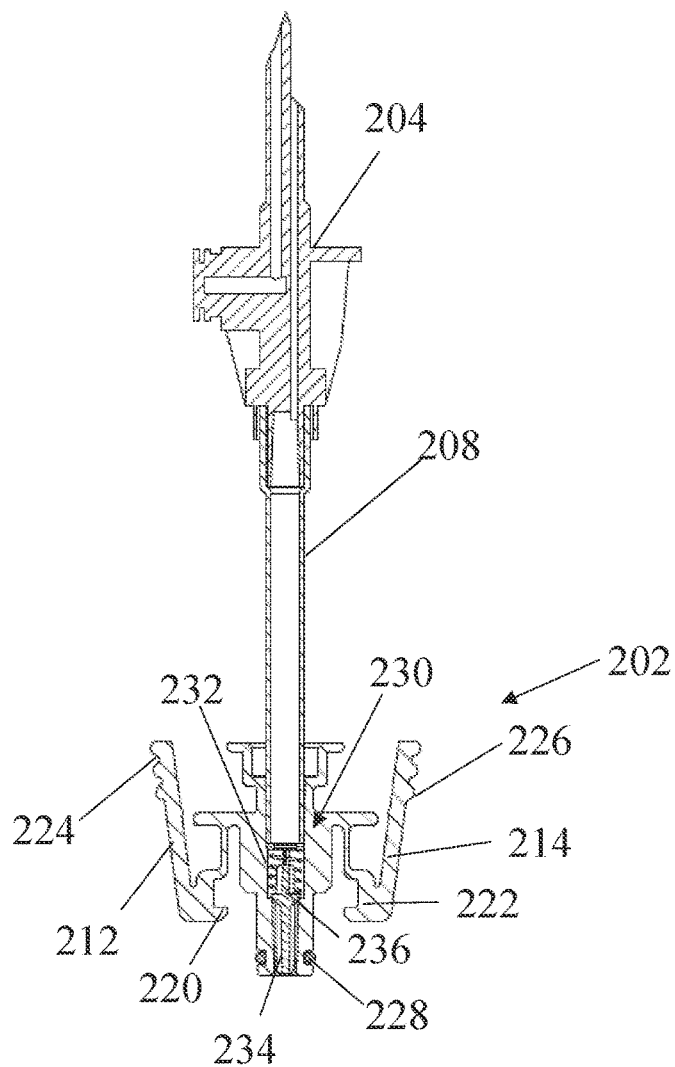
FIG. 42 is a cross-sectional view of the fluid path connector spike assembly of FIG. 38 in a closed position.
Figure 43:
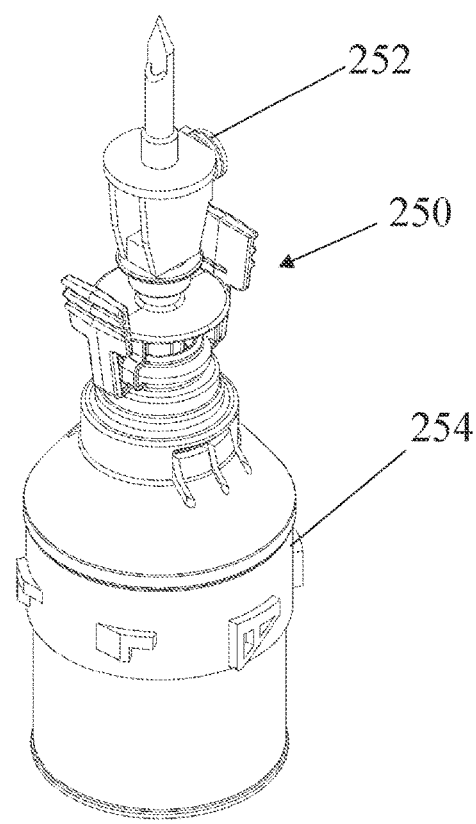
FIG. 43 is a perspective view of a fluid path connector assembly associated with a syringe and spike assembly according to another example of the present disclosure.

With reference to FIGS. 41 and 42, a valve member 230 may be provided in the connector element 202. The valve member 230 may include a spring 232 that allows a valve spool 234 to either remain open as shown in FIG. 41 or come into contact with a valve seat 236 of a stem 238 of the connector element 202 as shown in FIG. 42. When the valve spool 234 is in the open position, fluid is permitted to flow around it and into the fluid path. When the valve spool 234 is in the closed position, then fluid flow is stopped. As shown in FIGS. 41 and 42, the tip of a flow diverter 240 comes into contact with the valve spool 234 and then pushes it into the open position. While the valve spool 234 is still in contact with the valve seat 236 and the fluid channel is closed, the operator may insert the spike member 204 into a bulk fluid container without the risk of leakage until the fluid path is fully established. Once the connector element 202 has been connected to the fluid container 206, syringe, cap, or adaptor containing the flow diverter 240, the valve member 230 will open and fluid will be permitted to flow therethrough. Fluid diverters or other contact members for the valve spool 234 may be incorporated into any number of devices to disengage the valve spool 234 from the valve seat 236 and complete a fluid path. The presence of the flow diverter 240 allows the fluid to flow along the inside surface of the fluid container 206 receiving the fluid via the Coanda effect as described herein. Other such fill methods and adaptors have been described, for example, in WO2017/091643, the disclosure of which is incorporated in its entirety.

With reference to FIGS. 43-46, according to one example of the present disclosure, a connector element 250 is shown and described in detail. The connector element 250 may be directly fluidly connected to a spike member 252 and a fluid container 254. In one example of the present disclosure, the connector element 250 is substantially similar to the connector element 202 described above but does not include the valve spool 234, thus the fluid flow is not restricted whether or not the connector element 250 is attached to a device with a fluid diverter or other contact member. As can be appreciated by those of skill in the art, however, a valve including a valve spool and valve seat could be incorporated into the connector element 250 similar to the connector element 202 described above.

With reference to FIGS. 45 and 46, according to one example of the present disclosure, the connector element 250 may be connected to the spike member 252. The connection between the connector element 250 and the spike member 252 may occur via a friction fit, solvent bonding, gluing, or any other connective method as is known in the art.

Figure 47:
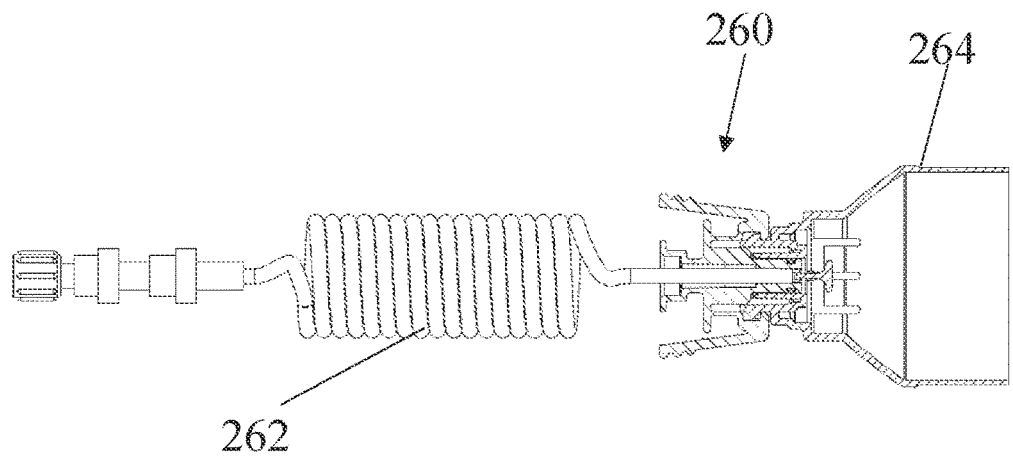
FIG. 47 is a side view of a fluid path connector assembly associated with a syringe and tubing set according to another example of the present disclosure.
Figure 48:
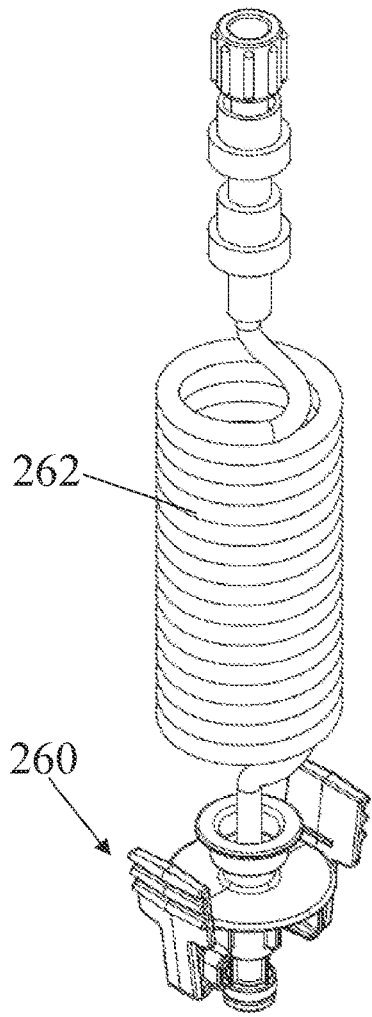
FIG. 48 is a perspective view of the fluid path connector assembly of FIG. 47.
Figure 49:
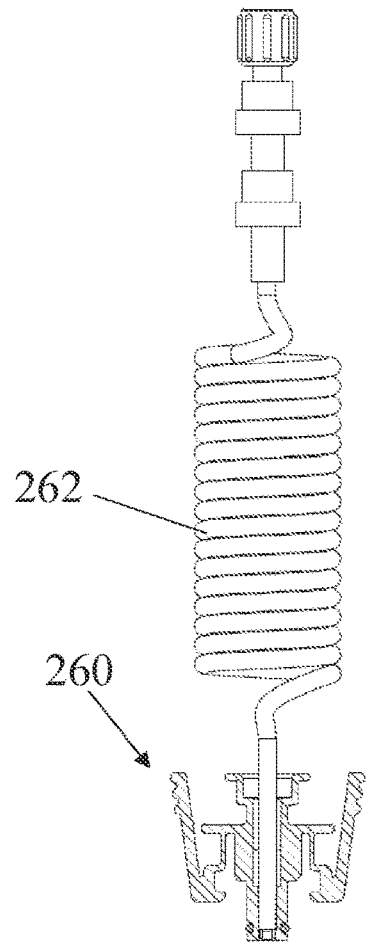
FIG. 49 is a side view of the fluid path connector assembly of FIG. 47.

With reference to FIGS. 47-49, according to one example of the present disclosure, a connector element 260 associated with a tubing set 262 is shown and described in detail. The connector element 260 may be fluidly connected to a fluid path tubing set 262 and a fluid container 264. A valve spool is not included in this example of the connector element 260, thus fluid flow is not restricted whether or not the connector element 260 is attached to a device with a fluid diverter or other contact member. However, as can be appreciated by those of skill in the art, a valve including a valve spool and valve seat could be incorporated into the connector element 260 similar to the connector element 202 described above. The connector element 260 may be connected to the fluid path tubing set 262 via a friction fit, solvent bonding, gluing, or other connective methods as is known in the art.

Figure 50:
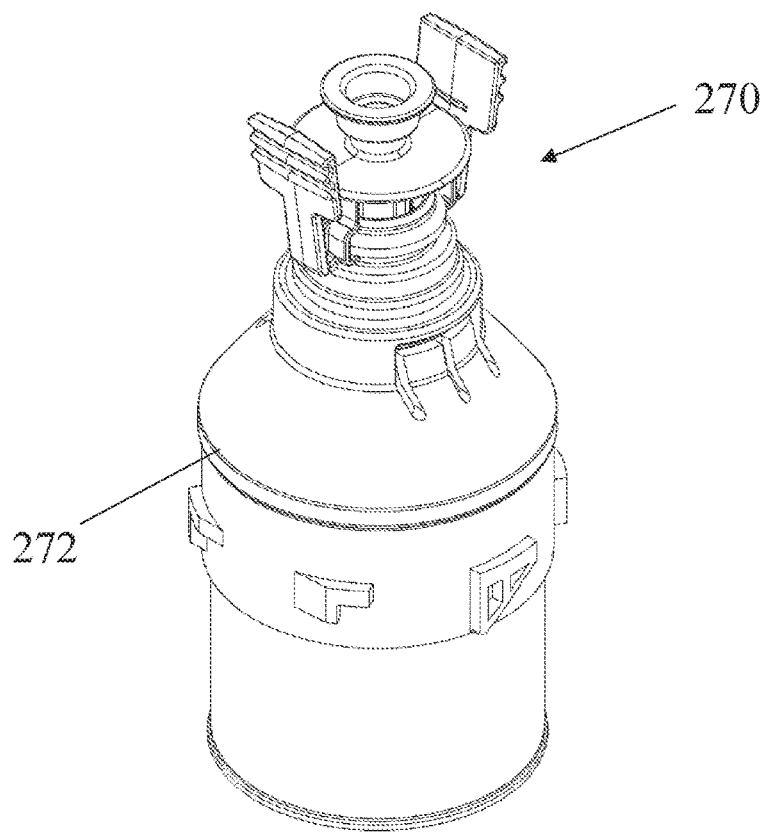
FIG. 50 is a perspective view of a fluid path connector assembly associated with a syringe according to another example of the present disclosure.
Figure 51:
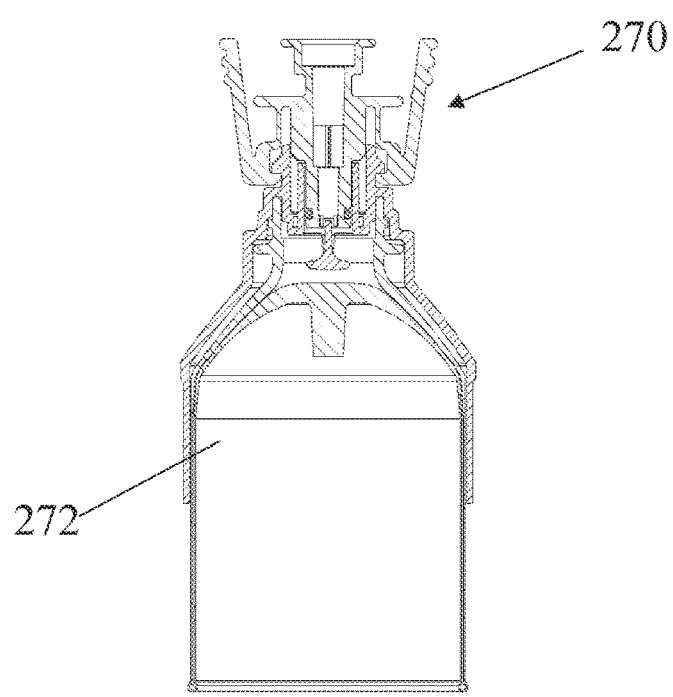
FIG. 51 is a cross-sectional view of the fluid path connector assembly of FIG. 50.
Figure 52:
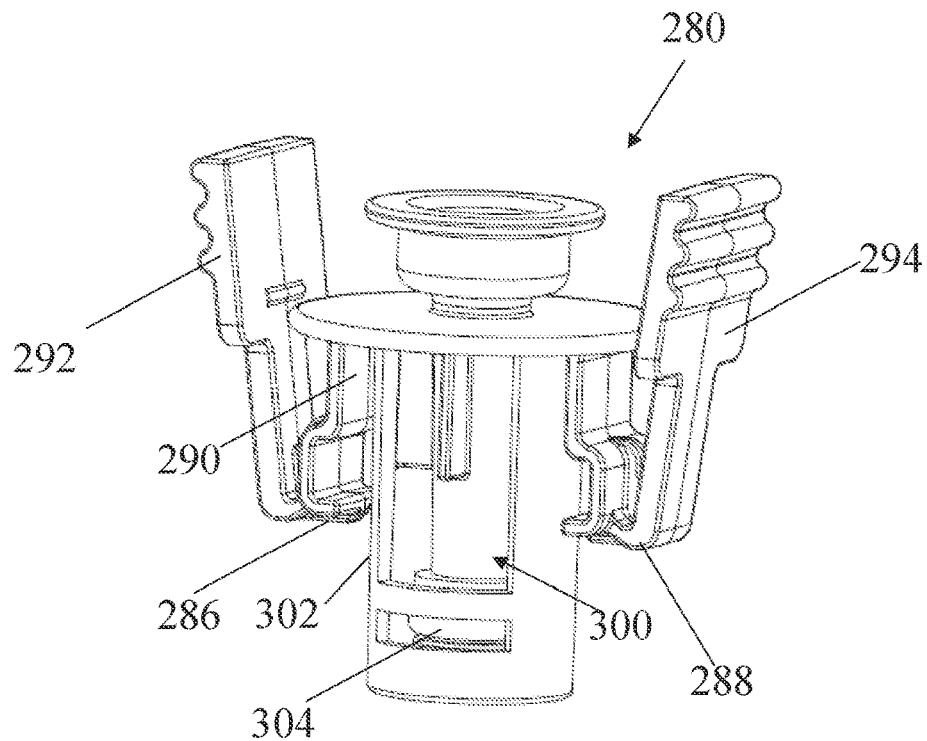
FIG. 52 is a perspective view of a connector element according to another example of the present disclosure.
Figure 53:
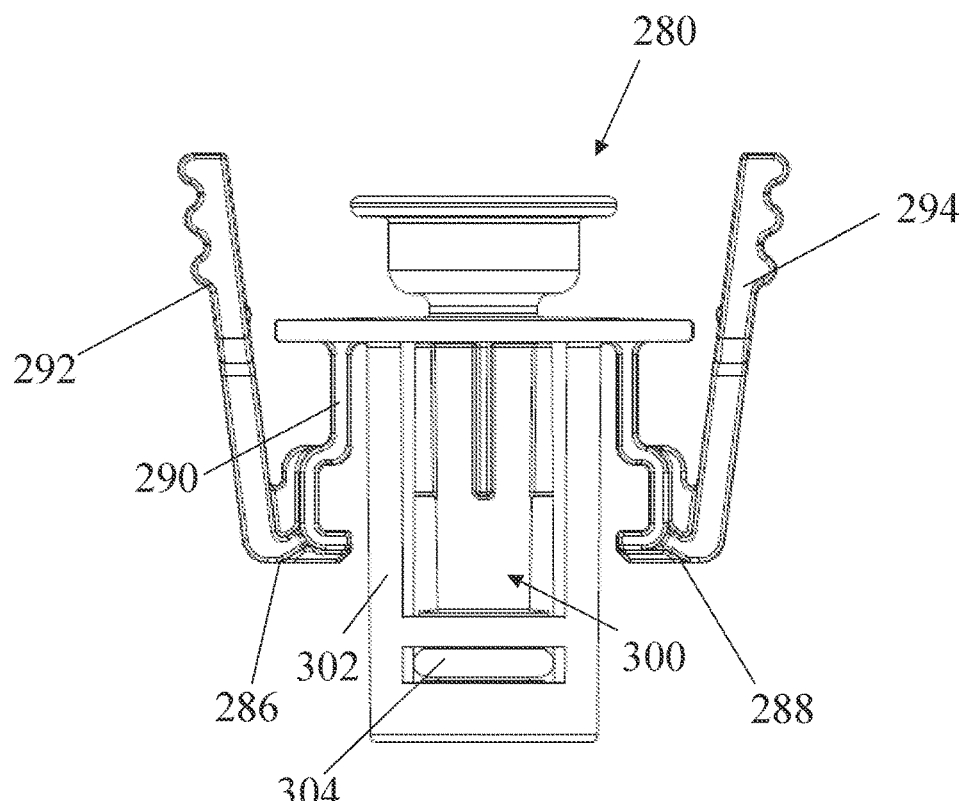
FIG. 53 is a side view of the connector element of FIG. 52.
Figure 54:
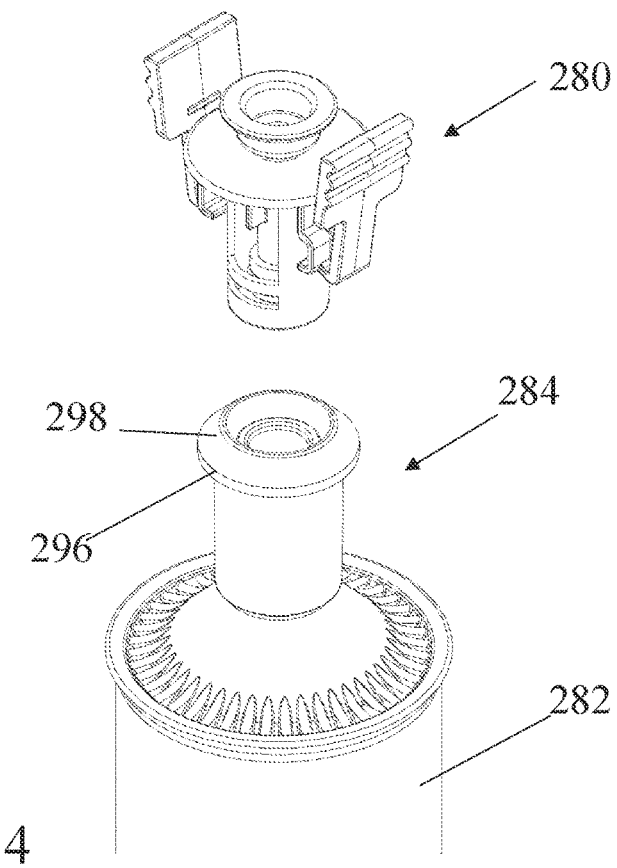
FIG. 54 is a perspective view of a fluid path connector assembly associated with a syringe according to an example of the present disclosure including the connector element of FIG. 52.
Figure 55:
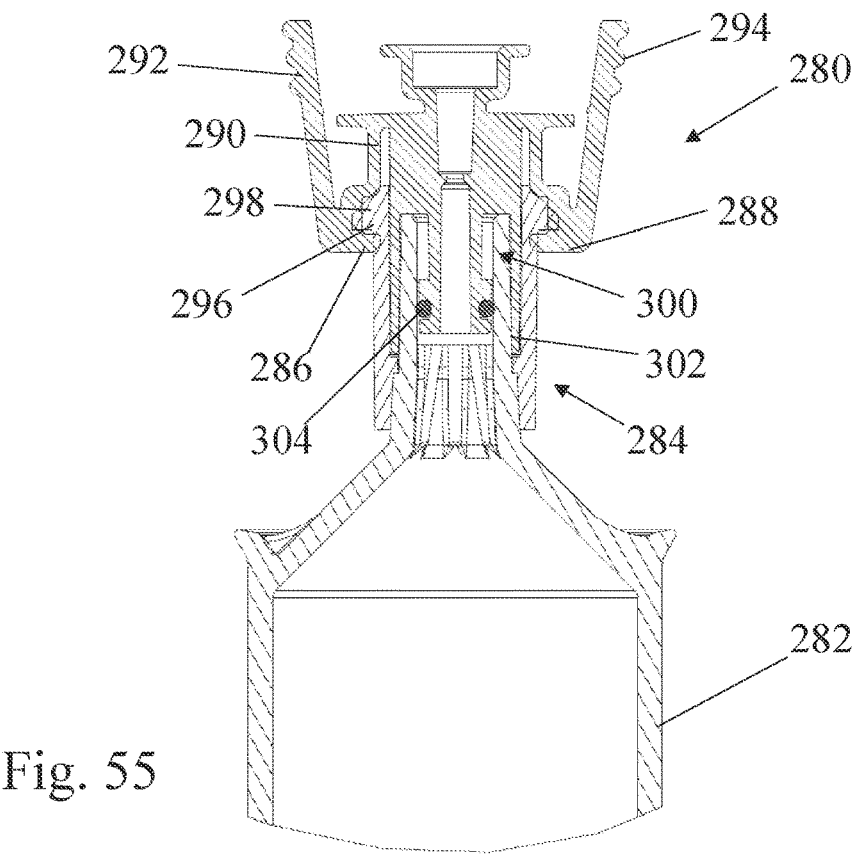
FIG. 55 is a cross-sectional view of the fluid path connector assembly of FIG. 54.

With reference to FIGS. 50 and 51, according to one example of the present disclosure, a connector element 270 is shown and described in detail. The connector element 270 may be directly connected to a fluid container 272. A valve spool is not included in this example of the connector element 270, thus fluid flow is not restricted whether or not the connector element 270 is attached to a device with a fluid diverter or other contact member. However, as can be appreciated by those of skill in the art, a valve including a valve spool and valve seat could be incorporated into the connector element 270 similar to the connector element 202 described above.

With reference to FIGS. 52-55, according to one example of the present disclosure, a connector element 280 is shown and described in detail. The connector element 280 may be fluidly connected to the connector element 282. In one example of the present disclosure, the first connector element 280 may be connected to a second connector element 284 provided on the fluid container 282. In order to connect the connector element 280 to the fluid container 282, a sloped surface 286 on the connector element 280 interacts with a sloped surface 288 on the second connector element 284 of the fluid container 282 as the two elements are pushed towards one another and come into contact with each other. Due to this interaction between the connector element 280 and the second connector element 284, a plurality of supports 290 on the connector element 280 are permitted to flex so that a pair of flexible legs 292, 294 are opened wide enough for the flexible legs 292, 294 to engage with a retention lip 296 on a collar 298 of the second connector element 284. It is to be understood that the fluid container 282 may be any number of containers as known in the art, for example, bottles, syringes, or a rolling diaphragm type syringe as disclosed in WO2016/172467, WO2015/164783, WO2016/069711, and 62/730,228.

The connector element 280 may include a male connector element 300 surround by a cylindrical skirt 302. The male connector element 300 may include a sealing member 304 and may be recessed within the skirt 302. The recess of the tip of the male connector element 300 may assist in retaining sterility of the male connector element 300, for example by preventing inadvertent touching and contamination of a surface of the male connector element 300 with a corresponding female connector element. In other embodiment, the connector element 280 may include a skirt surrounding a recessed female connector element. In one example, the male connector element 290 is received in a distal end of the fluid container 282 and a fluid-tight seal is created between the male connector element 290 and the inner surface of the fluid container 282 using the sealing member 304.

Figure 56:
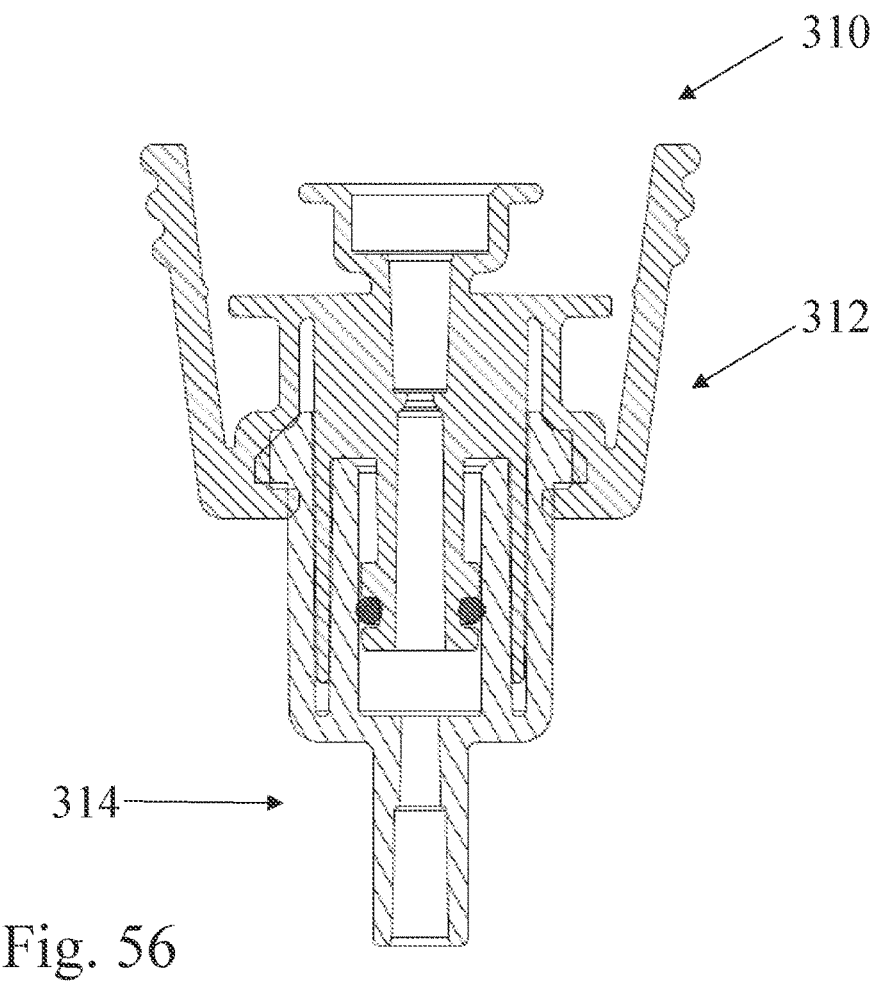
FIG. 56 is a cross-sectional view of a fluid path connector assembly according to another example of the present disclosure.

With reference to FIG. 56, according to one example of the present disclosure, a fluid path connector assembly 310 is shown and described in detail. The fluid path connector assembly 310 may include a first connector element 312 and a second connector element 314. In this example, the second connector element 314 may be integrally molded to the distal end of the fluid container, such as a syringe. The first connector element 312 may fit into a circumferential gap between the syringe tip and the inner surface of the second connector element 314. As the first connector element 312 is fitted into the distal end of the syringe, a skirt of the first connector element 312 may be fitted into the circumferential gap and may prevent leakage of the fluid during fluid injection. The circumferential gap may also collect fluid that may drip out of the distal tip of the syringe or from the fluid path connector assembly 310 during disconnection of the first connector element 312 from the syringe.

Figure 57:
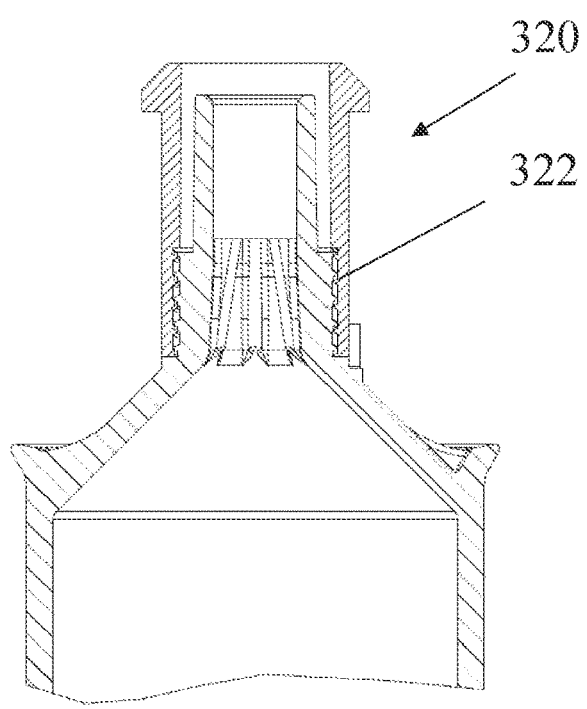
FIG. 57 is a cross-sectional view of a fluid path connector element associated with a syringe according to another example of the present disclosure.

With reference to FIG. 57, according to one example of the present disclosure, a connector element 320 is shown and described in detail. The connector element 320 may include a threaded inner surface 322 that engages with a corresponding outer threaded surface on a distal tip of a syringe. The connector element 320 may threadedly engage the syringe tip to engage lock the connector element 320 to the syringe tip. In certain examples, the connector element 320 may include a first locking member, such as a ratchet assembly at a proximal end of the connector element 320 that engages and locks with a second locking member, such as a protrusion or pawl at the proximal end of the thread on the syringe tip. In other examples, the position of the first and second locking members may be reversed. In some examples, as the connector element 320 threadably engages the threads of the syringe tip, the first ratcheted locking member may engage and lock with the second locking member once the connector element 320 is threaded onto the syringe tip. In some examples, the force of the connection may vary depending on the torque applied during the threading process and the tightness required for the particular injection process, for example the fluid injection pressures used.

Figure 58:
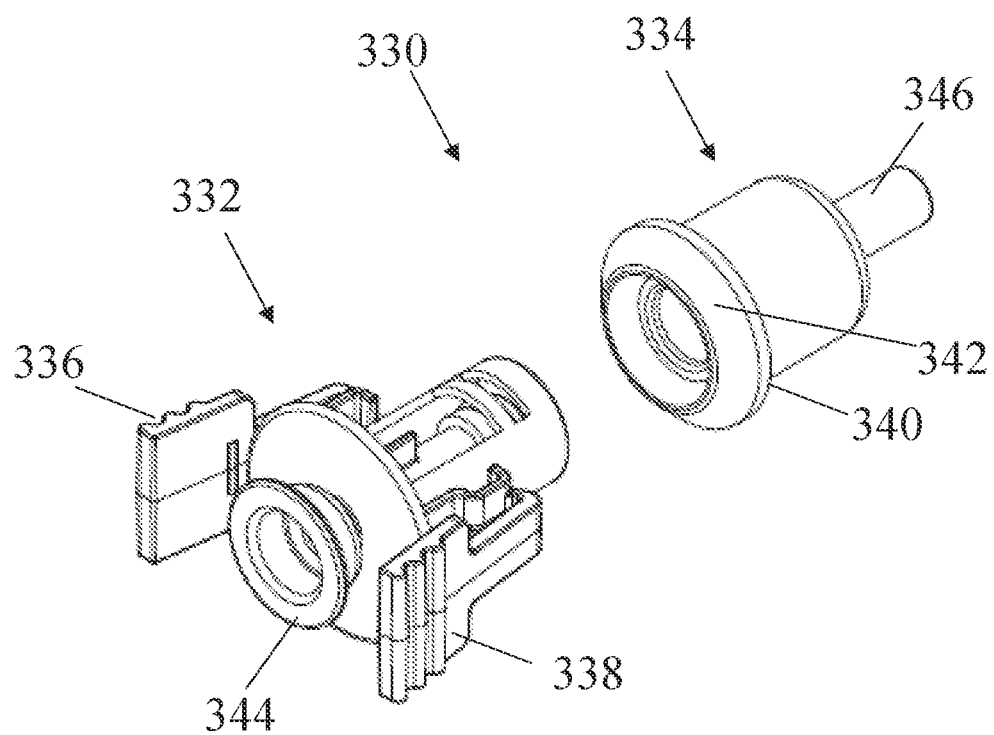
FIG. 58 is a perspective view of a fluid path connector assembly of FIG. 56 in a disconnected position.
Figure 59:
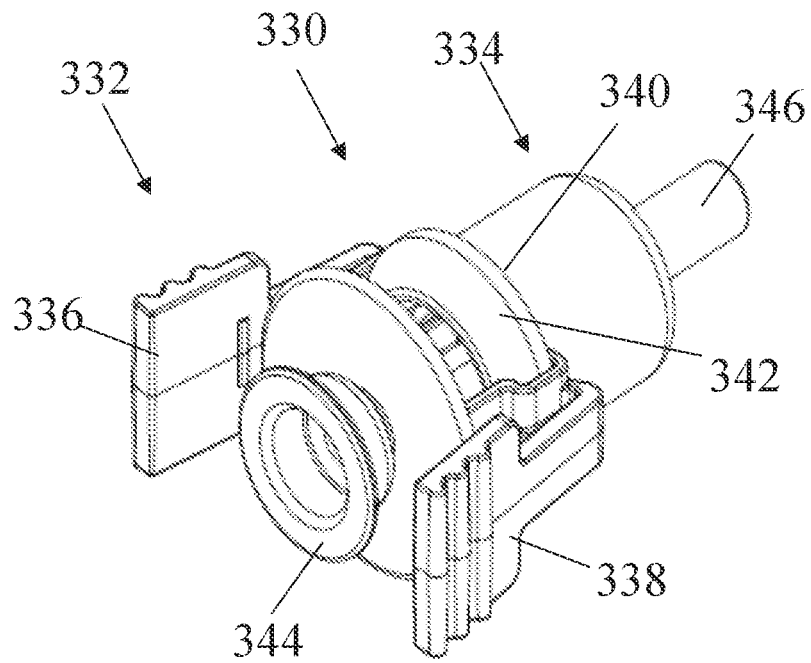
FIG. 59 is a perspective view of the fluid path connector assembly of FIG. 58 shown in a connected position.
Figure 60:
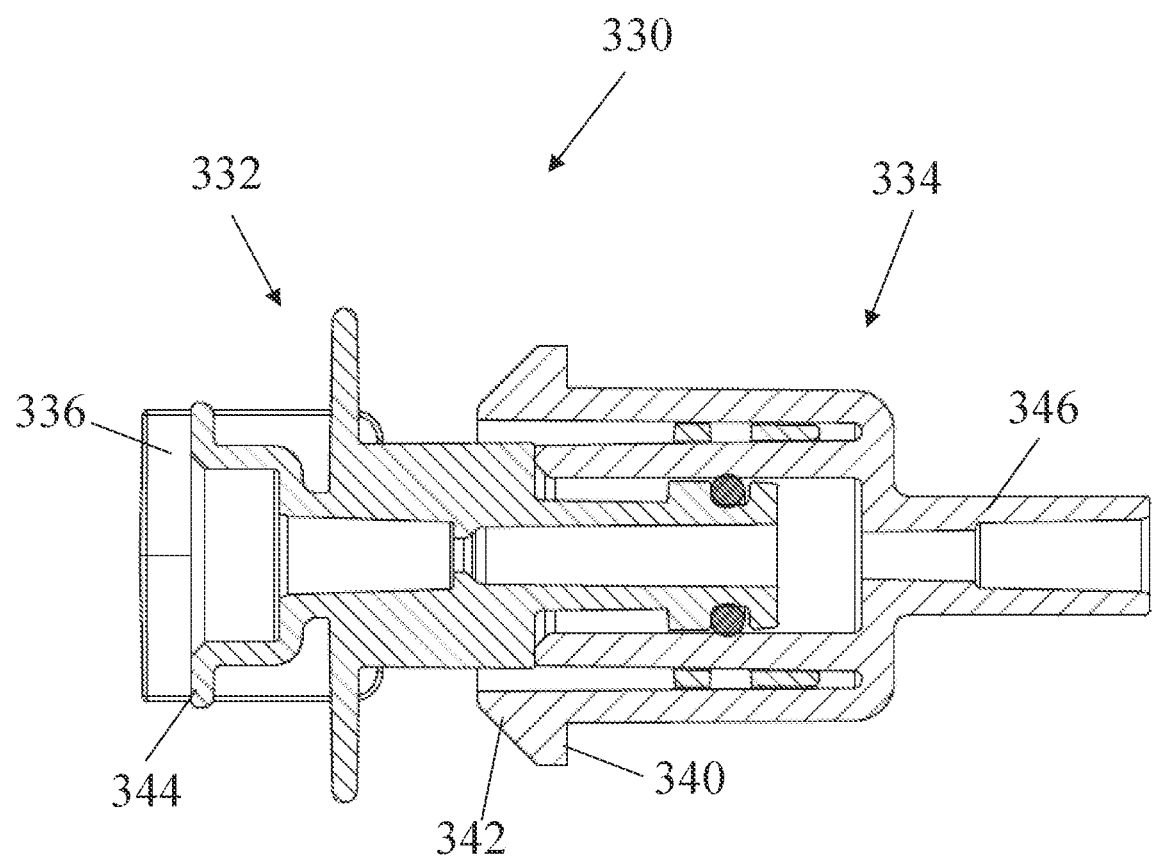
FIG. 60 is a cross-sectional view of the fluid path connector assembly of FIG. 56 rotated 90 degrees around a longitudinal axis shown in the connected position.

With reference to FIGS. 58-60, according to an example of the present disclosure, a fluid path connector assembly 330 is shown and described in detail. This fluid path connector assembly 330 may be used for connecting two portions of a tubing set (not shown) in a fluid tight connection. The fluid path connector assembly 330 may include a male connector element 332, which may be attached to an end of a first tubing set, and a female connector element 334, which may be attached to an end of a second tubing set. The male connector element 332 may include flexible legs 336, 338 for forming a positive locking engagement with a retention lip 340 on a collar 342 of the female connector element 334. Each of the male and female connector elements 332, 334 may include a tubing set connector element 344, 346 for connecting to the respective tubing set.

The fluid connector assemblies of the various examples described herein may be suited for use with a medical fluid injector, for example a powered CT fluid injector system, a powered MR fluid injector system, and a powered CV angiography injector system. The fluid connector assemblies may be suited for high pressure injection procedures and may demonstrate an increased connective force between the connector elements during a high-pressure injection procedure, such as a CV injection procedure which may involve fluid pressures of up to 1200 psi or CT or MR injection procedures which may involve fluid pressures of up to 400 psi.

Figure 61:
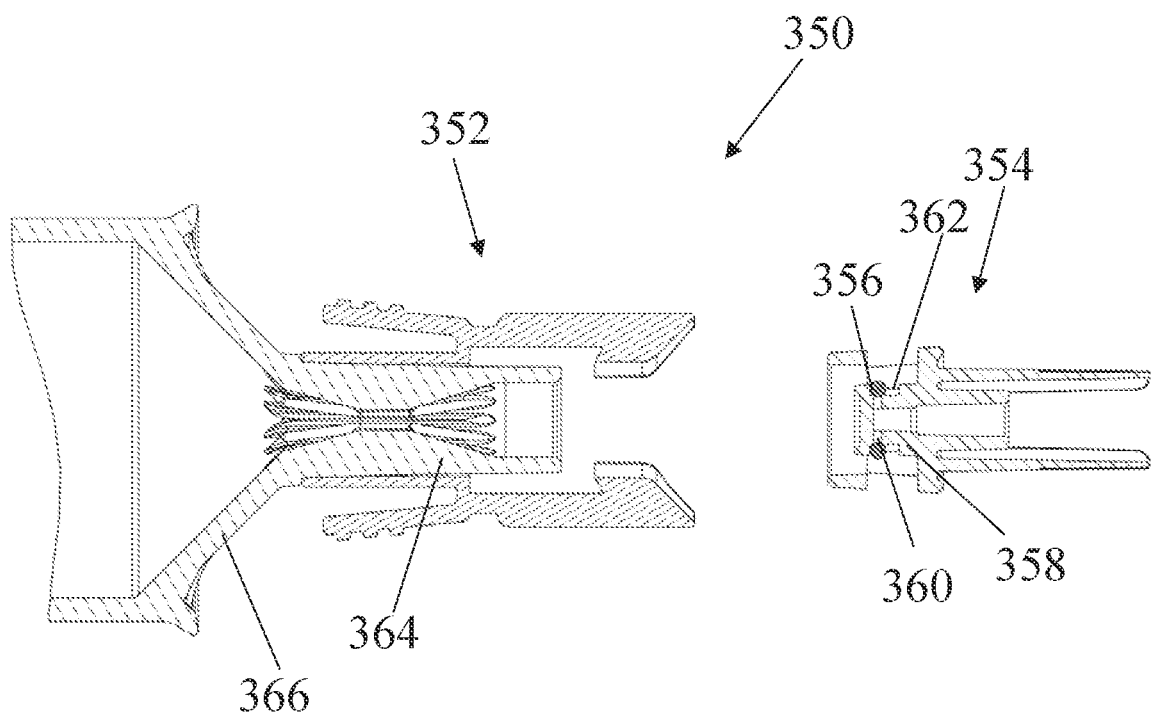
FIG. 61 is a cross-sectional view of a fluid path connector assembly according to another example of the present disclosure shown in a disconnected position.
Figure 62:
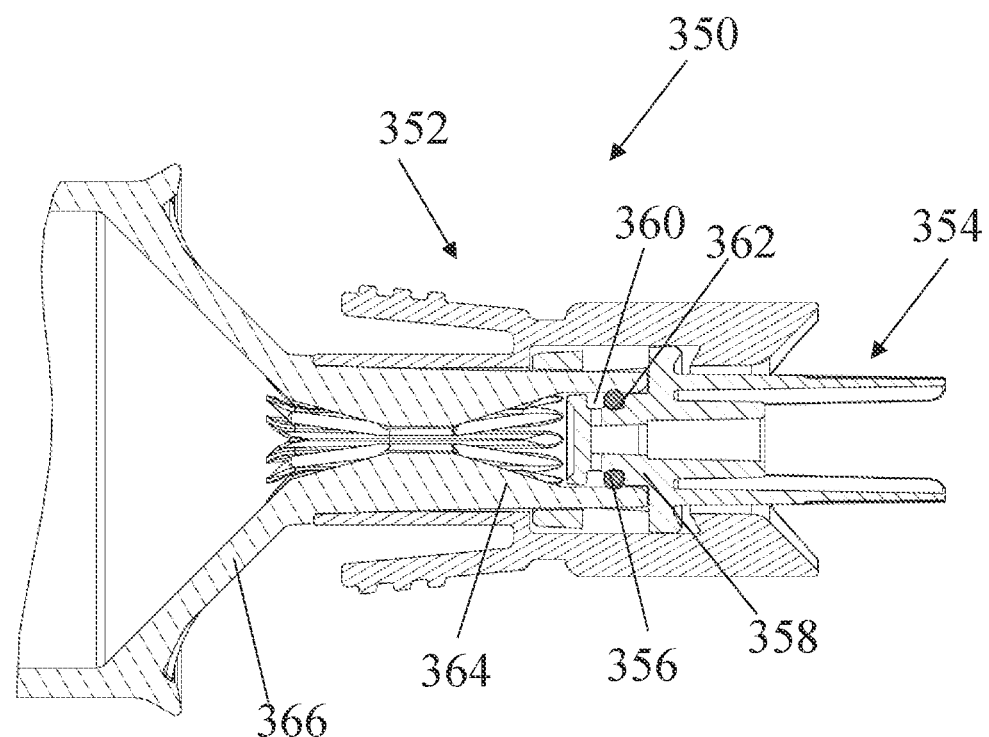
FIG. 62 is a cross-sectional view of the fluid path connector assembly of FIG. 61 shown in a connected position.

With reference to FIGS. 61 and 62, according to one example of the present disclosure, a fluid path connector assembly 350 is shown and described in detail. The fluid path connector assembly 350 may include a first connector element 352 and a second connector element 354 that may be operatively connected to one another to create a fluid-tight seal between a syringe and a tubing set or fluid container. In one example of the present disclosure, the first connector element 352 is substantially similar to the first connector element 12 described above, and the second connector element 354 is substantially similar to the second connector element 14 described above. However, in the present example of the fluid path connector assembly 350, the second connector element 354 may include an additional feature for creating a fluid-tight seal between the second connector element 354 and a fluid container, while preventing fluid flow through the second connector element 354 when disconnected. A movable sealing member 356 may be provided on a connection member 358 of the second connector element 354. In one example of the present disclosure, the sealing member 356 may be an elastomeric O-ring, or slidable sealing element. The connection member 358 may define a circumferential fluid channel 360 and a circumferential groove 362 in an outer surface of the connection member 358. The sealing member 354 may be held in either of the circumferential fluid channel 360 and the circumferential groove 362. The sealing member 354 may be provided to create a fluid-tight seal between the connection element 358 and a distal tip of a syringe. In one example of the present disclosure, the sealing member 354 may slide and/or roll between the circumferential fluid channel 360 and the circumferential groove 362 of connection member 358 upon removal and insertion, respectively of the second connector member 354 with first connector member 352.

With continued reference to FIGS. 61 and 62, an operation of the fluid path connector assembly 350 according to the present example of the disclosure is shown and described in detail. A disconnected position of the fluid path connector assembly 350 is illustrated in FIG. 61. In the disconnected position, the sealing member 356 may be held in the circumferential fluid channel 360, which seals the circumferential fluid channel 360 such that fluid cannot pass through the second connector element 354 from a bulk fluid container or tubing set to which the second connector element 354 may be connected. When the sealing member 356 is held in the circumferential fluid channel 360 when the fluid path connector assembly 350 is in the disconnected position, the sealing member 356 prevents fluid from leaking from the second connector element 354 when connected to a bulk fluid container. This prevents fluid leaks from the bulk fluid container through the second connector member 354 when a user disconnects the second connector element 354 from the first connector element 352 after filling syringe 366 with fluid.

With reference to FIG. 62, the fluid path connector assembly 350 is shown in a connected position in which the first and second connector elements 352, 354 are connected to one another. During the connection procedure, the connection member 358 is inserted into the first connector element 352. As the connection member 358 is inserted into the first connector element 352, the sealing member 356 may come into frictional engagement with an inner surface of a distal tip 364 of the syringe 366. As the connection member 358 is further inserted into the first connector element 352, the sealing member 356 continues to slide along the inner surface of the distal tip 364 of the syringe 366. The sliding motion of the sealing member 356 along the inner surface of the distal tip 364 of the syringe 366 may create a frictional force to cause the sealing member 356 to roll or slide from the circumferential fluid channel 360 to the circumferential groove 362. Once the sealing member 356 is positioned in the circumferential groove 362, the circumferential fluid channel 360 is opened, thereby permitting fluid to flow from the second connector element 354 to the first connector element 352 through the circumferential fluid channel 360 and into the syringe 366. After the syringe 366 has been filled, the fluid path connector assembly 350 may be disconnected. As the second connector element 354 is pulled away from the first connector element 352, the sealing member 356 is pulled along the inner surface of the distal tip 364 of the syringe 366. As the sealing member 356 is pulled along the inner surface of the distal tip 364 of the syringe 366, a frictional force may cause the sealing member 356 to roll or slide from the circumferential groove 362 to the circumferential fluid channel 360, thereby sealing the circumferential fluid channel 360 as the fluid path connector assembly 350 is moved into the disconnected position. In one example of the present disclosure, a spike member or a tubing set may be connected to the second connector element 354 to transfer fluid to the syringe 366 from a bulk fluid source.

While various examples of the present disclosure were provided in the foregoing description, those skilled in the art may make modifications and alterations to these examples without departing from the scope and spirit of the disclosure. Accordingly, the foregoing description is intended to be illustrative rather than restrictive. The disclosure described hereinabove is defined by the appended claims, and all changes to the disclosure that fall within the meaning and the range of equivalency of the claims are to be embraced within their scope.

The invention claimed is:

1. A fluid path connector for a medical fluid delivery system, the fluid path connector comprising:
  a first connector element comprising a body, a first lumen, a first flexible leg, a second flexible leg, a first actuating arm associated with the first flexible leg, and a second actuating arm associated with the second flexible leg; and
  a second connector element comprising a body defining an undercut having a sloped surface, a second lumen, a channel defined in the body, and at least one sealing element positioned within the channel,
  wherein the first flexible leg comprises a first flange and the second flexible leg comprises a second flange, wherein the first flange and the second flange are each angled at an angle from 45-75 degrees relative to a longitudinal axis of the first connector element,
  wherein, upon engagement of the first connector element with the second connector element, the first flange and the second flange engage with the sloped surface of the undercut of the body of the second connector element to prevent disengagement of the first connector element and the second connector element,
  wherein, upon applying an inwardly-directed pressure to the first actuating arm and the second actuating arm, the first flexible leg and the second flexible leg move in an outward direction relative to the body of the second connector element to disengage the first flange and the second flange from the undercut to allow the first connector element and the second connector element to be disengaged, and
  wherein the at least one sealing element is configured to define a fluid tight seal between the second lumen of the second connector element and the first lumen of the first connector element to form a fluid path when the first connector element and the second connector element are engaged with one another.

2. The fluid path connector of claim 1, wherein the first connector element and the second connector element are each configured to be in fluid communication with a fluid delivery element selected from the group consisting of a syringe, a spike member, a fluid tube set, and a bulk fluid container.

3. The fluid path connector of claim 2, wherein at least one of the first connector element and the second connector element further comprises a fluid path adaptor configured for connecting the at least one of the first connector element and the second connector element to the fluid delivery element.

4. The fluid path connector of claim 1, wherein the first flange and the second flange are each angled inwardly towards the longitudinal axis of the first connector element.

5. The fluid path connector of claim 1, wherein at least one of the first flexible leg and the second flexible leg includes at least one reinforcing rib.

6. The fluid path connector of claim 1, wherein, when the first connector element and the second connector element are connected to one another, the connection between the first connector element and the second connector element is configured to withstand a fluid pressure in the fluid path of at least 800 psi.

7. The fluid path connector of claim 1,
wherein the first connector element further comprises a support base that extends from the body between the first flexible leg and the second flexible leg, and
wherein the support base is configured to reduce deflection of the body due to a fluid pressure exerted by a fluid in the fluid path.

8. The fluid path connector of claim 7, wherein the support base comprises at least one support base reinforcing rib to reduce deflection of the body due to the fluid pressure exerted by the fluid in the fluid path.

9. The fluid path connector of claim 1, wherein the at least one sealing element is selected from the group consisting of an elastomeric O-ring, an overmolded sealing surface, and a quad ring.

10. The fluid path connector of claim 1, wherein at least one of the first connector element and the second connector element further comprises a skirt that surrounds the body of the first connector element and the body of the second connector element.

11. The fluid path connector of claim 10, wherein the skirt extends beyond a distal end of the body of at least one of the first connector element and the second connector element.

12. The fluid path connector of claim 10, wherein at least one aperture is defined in the skirt when the skirt is on the second connector element.

13. The fluid path connector of claim 1, wherein the first flange of the first flexible leg and the second flange of the second flexible leg each flex radially outward as they pass the undercut of the second connector during an engagement process and return to an unflexed position to contact and engage the undercut of the second connector element to engage and the first connector element with the second connector element, and
wherein the first lumen and the second lumen are in fluid communication in the engaged position.

14. The fluid path connector of claim 13, wherein the first connector and the second connector are non-reversibly engaged when the first flange and the second flange of the first connector element engage the undercut of the second connector element.

15. A medical fluid delivery system, comprising:
a syringe comprising a proximal end, a distal end, and a sidewall extending from the proximal end to the distal end;
a fluid delivery member; and
a fluid path connector, comprising:
a first connector element comprising a body, a first lumen, a first flexible leg, and a second flexible leg; and
a second connector element comprising a body defining an undercut having a sloped surface, a second lumen, a channel defined in the body, and at least one sealing element positioned within the channel,
wherein the first connector element is fluidly connected to one of the fluid delivery member and the distal end of the syringe,
wherein the second connector element is fluidly connected to the other of the fluid delivery member and the distal end of the syringe,
wherein the first flexible leg comprises a first flange and the second flexible leg comprises a second flange, wherein the first flange and the second flange are each angled at an angle from 45-75 degrees relative to a longitudinal axis of the first connector element,
wherein, upon engagement of the first connector element with the second connector element, the first flange and the second flange engage with the sloped surface of the undercut of the body of the second connector element to prevent disengagement of the first connector element and the second connector element, and
wherein the at least one sealing element is configured to define a fluid tight seal between the second lumen of the second connector element and the first lumen of the first connector element to form a fluid path when the first connector element and the second connector element are engaged with one another.

16. The medical fluid delivery system of claim 15, wherein the first connector element and the second connector element are each configured to be in fluid communication with a fluid path element selected from the group consisting of a syringe, a spike member, a fluid tube set, and a bulk fluid container.

17. A fluid path connector for a medical fluid delivery system, the fluid path connector comprising:
a first connector element comprising a body having a support base, a first lumen, a first flexible leg having a first actuating arm, and a second flexible leg having a second actuating arm, wherein at least one of the first flexible leg and the second flexible leg includes at least one reinforcing rib; and
a second connector element comprising a body defining an undercut having a sloped surface, a second lumen, a channel defined in the body, and at least one sealing element positioned within the channel,
wherein the first flexible leg comprises a first flange and the second flexible leg comprises a second flange and the first flange and the second flange are each inwardly angled at an angle from 45-75 degrees relative toward a longitudinal axis of the first connector element,
wherein, upon engagement of the first connector element with the second connector element, the first flange and the second flange engage with the sloped surface of the undercut of the body of the second connector element to prevent disengagement of the first connector element and the second connector element,
wherein, upon applying an inwardly-directed pressure to the first actuating arm and the second actuating arm, the first flexible leg and the second flexible leg move in an outward direction relative to the body of the second connector element to disengage the first flange and the second flange from the undercut to allow the first connector element and the second connector element to be disengaged, and
wherein the at least one sealing element is configured to define a fluid tight seal between the second lumen of the second connector element and the first lumen of the first connector element to form a fluid path when the first connector element and the second connector element are engaged with one another.

18. The fluid path connector of claim 17, wherein, when the first connector element and the second connector element are connected to one another, the connection between the first connector element and the second connector element is configured to withstand a fluid pressure in the fluid path of at least 800 psi.

19. A fluid path connector for a medical fluid delivery system, the fluid path connector comprising:
a first connector element comprising a body, a first lumen, a first flexible leg, and a second flexible leg; and
a second connector element comprising a body defining an undercut having a sloped surface, a second lumen, a channel defined in the body, and at least one sealing element positioned within the channel, wherein the first flexible leg comprises a first flange and the second flexible leg comprises a second flange, wherein the first flange and the second flange are each angled at an angle from 45-75 degrees relative to a longitudinal axis of the first connector element, wherein the first flange of the first flexible leg and the second flange of the second flexible leg each flex radially outward as they pass the undercut of the second connector during an engagement process and return to an unflexed position to contact and engage the sloped surface of the undercut of the second connector element to engage and the first connector element with the second connector element, wherein, upon engagement of the first connector element with the second connector element, the first flange and the second flange engage with the undercut of the body of the second connector element to prevent disengagement of the first connector element and the second connector element, wherein the at least one sealing element is configured to define a fluid tight seal between the second lumen of the second connector element and the first lumen of the first connector element to form a fluid path when the first connector element and the second connector element are engaged with one another, and wherein the first lumen and the second lumen are in fluid communication in the engaged position.

\* \* \* \* \*